United States Patent
Ochsner et al.

(10) Patent No.: US 10,808,251 B2
(45) Date of Patent: Oct. 20, 2020

(54) NUCLEIC ACID COMPOUNDS FOR BINDING GROWTH DIFFERENTIATION FACTOR 11

(71) Applicant: SOMALOGIC, INC., Boulder, CO (US)

(72) Inventors: Urs Ochsner, Boulder, CO (US); Louis Green, Boulder, CO (US); Dom Zichi, Boulder, CO (US); Nebojsa Janjic, Boulder, CO (US)

(73) Assignee: SOMALOGIC, INC., Boulder, CO (US)

(*) Notice: Subject to any disclaimer, the term of this patent is extended or adjusted under 35 U.S.C. 154(b) by 339 days.

(21) Appl. No.: 15/525,186

(22) PCT Filed: Nov. 23, 2015

(86) PCT No.: PCT/US2015/062155
§ 371 (c)(1),
(2) Date: Oct. 5, 2018

(87) PCT Pub. No.: WO2016/085860
PCT Pub. Date: Jun. 2, 2016

(65) Prior Publication Data
US 2019/0024087 A1 Jan. 24, 2019

Related U.S. Application Data

(60) Provisional application No. 62/083,592, filed on Nov. 24, 2014, provisional application No. 62/113,864, filed on Feb. 9, 2015.

(51) Int. Cl.
*C07H 21/04* (2006.01)
*C12N 15/115* (2010.01)
*G01N 33/53* (2006.01)
*C07K 14/52* (2006.01)

(52) U.S. Cl.
CPC ....... *C12N 15/115* (2013.01); *G01N 33/5308* (2013.01); *C07K 14/52* (2013.01); *C12N 2310/16* (2013.01); *G01N 2333/495* (2013.01)

(58) Field of Classification Search
None
See application file for complete search history.

(56) References Cited

U.S. PATENT DOCUMENTS

2016/0074477 A1* 3/2016 Wagers .............. A61K 38/1875
514/4.8

FOREIGN PATENT DOCUMENTS

| WO | 99006559 A1 | 2/1999 |
|----|-------------|--------|
| WO | 2008030706 A2 | 3/2008 |
| WO | 2009058346 A1 | 5/2009 |
| WO | 2011150008 A1 | 12/2011 |
| WO | 2012024242 A1 | 2/2012 |
| WO | 2013142114 A1 | 9/2013 |
| WO | 2014066486 A2 | 5/2014 |

OTHER PUBLICATIONS

Kimoto, Michiko, et al. "Generation of high-affinity DNA aptamers using an expanded genetic alphabet." Nature biotechnology 31.5 (2013): 453.*
Gold et al., "Aptamer-based multiplexed proteomic technology for biomarker discovery," PLoS One, 5(12):e15004, Dec. 7, 2010.
Rohloff et al., "Nucleic Acid Ligands with Protein-Like Side Chains: Modified Aptamers and their use as Diagnostic and Therapeutic Agents," Mol. Ther. Nucleic Acids, Oct. 7, 2014, No. 3, pp. e201.
Search Report issued in Singapore Application No. 11201703748P, dated Apr. 4, 2018, 3 pages.
Loffredo et al., "Growth Differentiation Factor 11 Is a Circulating Factor that Reverses Age-Related Cardiac Hypertrophy," Cell 153, 828-839, May 9, 2013.
Olson et al., "High Levels of Growth Differentiation Factor 11 are Associated with Lower Prevalence of Left Ventricular Hypertrophy: Data from the Heart and Soul Study," JACC 63:12; Apr. 1, 2014.
International Search Report and Written Opinion issued in PCT/US2015/062155, dated Mar. 30, 2016, 16 pages.
Search Report issued in Russian Application No. 2017121801, dated May 27, 2019, 2 pages.
Nakashima et al., "Expression of growth/differentiation factor 11, a new member of the BMP/TGFβ superfamily during mouse embryogenesis," Mechanisms of Development 80:185-189 (1999).

* cited by examiner

Primary Examiner — Kimberly Chong
(74) Attorney, Agent, or Firm — McNeill Baur PLLC

(57) ABSTRACT

Described herein are aptamers capable of binding to growth differentiation factor 11 (GDF11) protein; compositions comprising a GDF11 binding aptamer with a GDF11 protein; and methods of making and using the same.

21 Claims, 3 Drawing Sheets

Specification includes a Sequence Listing.

NUCLEIC ACID COMPOUNDS FOR BINDING GROWTH DIFFERENTIATION FACTOR 11

CROSS-REFERENCE TO RELATED APPLICATIONS

This application is a national phase entry pursuant to 35 U.S.C. § 371 of International Application No. PCT/US2015/062155, filed Nov. 23, 2015, which claims the benefit of priority of U.S. Provisional Application No. 62/083,592, filed Nov. 24, 2014, and U.S. Provisional Application No. 62/113,864, filed Feb. 9, 2015, each of which is incorporated by reference herein in its entirety for any purpose.

SEQUENCE LISTING

The present application is filed with a Sequence Listing in electronic format. The Sequence Listing is provided as a file entitled "2015-11-23_01137-0011-00PCT_ST25.txt" created on Nov. 23, 2015, which is 122,816 bytes in size. The information in the electronic format of the sequence listing is incorporated herein by reference in its entirety.

FIELD

The present disclosure relates generally to the field of nucleic acids, and more specifically, to aptamers capable of binding to growth differentiation factor 11 (GDF11) protein; compositions comprising a GDF11 binding aptamer with a GDF11 protein; and methods of making and using the same.

BACKGROUND

Growth differentiation factor 11 (GDF11) or bone morphogenetic protein 11 (BMP-11) belongs to the transforming growth factor beta superfamily that controls anterior-posterior patterning during development by regulating the expression of Hox genes. GDF11 has been shown to play a role in the regulation of cardiacmyocyte proliferation, kidney organogenesis, pancreatic development, act as a negative regulator of neurogenesis and chondrogenesis.

GDF11 is closely related to myostatin (GDF8), which is a negative regulator of muscle growth. Like GDF11, myostatin is involved in the regulation of cardiacmyocyte proliferation. The similarities between GDF11 and myostatin imply a likelihood that the same regulatory mechanisms are used to control tissue size during both muscular and neural development. Mechanistically, the actions of GDF11 are likely regulated by WFIKKN2, a large extracellular multi-domain protein consisting of follistatin, immunoglobulin, protease inhibitor, and NTR domains. WFIKKN2 has a high affinity for GDF11, and previously has been found to inhibit the biological activities of myostatin.

Both GDF11 and GDF8 (myostatin) play important roles in the course of development, and in the regulation of cell growth and differentiation in adult tissues. The ability to localize and/or measure these two proteins is important to further understand and distinguish their contributions in development and adult tissues (e.g., cardiac and skeletal muscle). However, due to their homology it is difficult to distinguish the presence and/or levels of these proteins with current protein binding reagents (e.g., antibodies). Thus, there is a need for protein binding reagents that are capable of distinguishing the proteins GDF11 and GDF8. The present disclosure meets such needs by providing aptamers having binding specificity to a GDF11 protein.

SUMMARY

The present disclosure describes aptamers capable of binding to growth differentiation factor 11 (GDF11) protein. In some embodiment, aptamers that bind GDF11 with an equilibrium binding constant ($K_d$) of less than 100 nM are provided. In another aspect, the $K_d$ is from about 0.1 nM to about 100 nM (or from about 0.1 nM to about 50 nM, or from about 0.1 nM to about 10 nM, or from about 0.5 nM to about 10 nM, or from about 0.5 nM to about 5 nM).

In some embodiments, an aptamer that binds GDF11 with an affinity of less than 10 nM is provided. In some embodiments, the aptamer binds GDF11 with an affinity of less than 10 nM, and, under the same conditions, the aptamer binds GDF8 with an affinity that is at least 10-fold weaker than the affinity for GDF11. In some embodiments, the aptamer does not bind GDF8. In some embodiments, the aptamer binds GDF8 with an affinity that is at least 20-fold weaker, or at least 30-fold weaker, or at least 50-fold weaker than the affinity for GDF11. In some embodiments, the aptamer binds GDF8 with an affinity greater than 50 nM, or greater than 100 nM, or greater than 150 nM, or greater than 200 nM, or greater than 250 nM, or greater than 300 nM. In some embodiments, the aptamer binds GDF11 with an affinity of less than 8 nM, or less than 7 nM, or less than 6 nM, or less than 5 nM, or less than 4 nM, or less than 3 nM, or less than 2 nM, or less than 1 nM. In some embodiments, affinity is determined using a binding assay comprising a polyanionic inhibitor. In some embodiments, the polyanionic inhibitor is selected from dextran sulfate, heparin, Z-block, poly-dI/dC, sonicated or sheared salmon sperm DNA, calf thymus DNA, and dNTPs. In some embodiments, the aptamer comprises the sequence 5'-RW$_n$MC$_n$CPPGM$_m$MPPPA$_n$AC$_n$MC$_m$RW$_n$-PPG$_n$PAS$_n$GC-3'(SEQ ID NO:110) or 5'-RW$_n$MC$_n$CPPGM$_m$MPPPA$_n$AC$_n$MC$_m$RW$_n$PPG$_n$PAS$_n$GS-3' (SEQ ID NO: 151), wherein:

each P is independently, and for each occurrence, a C-5 modified pyrimidine;
R is A or G;
each W is independently, and for each occurrence, A, T, or U;
each M is independently, and for each occurrence, A or C;
each S is independently, and for each occurrence, G or C;
each n is independently, and for each occurrence, 0 or 1; and
each m is independently, and for each occurrence, 0 or 1.

In some embodiments, an aptamer that binds GDF11 is provided, wherein the aptamer comprises the sequence 5'-RW$_n$MC$_n$CPPGM$_m$MPPPA$_n$AC$_n$MC$_m$RW$_n$PPG$_n$-PAS$_n$GC-3' (SEQ ID NO:110) or 5'-RW$_n$MC$_n$CPPGM$_m$MP-PPA$_n$AC$_n$MC$_m$RW$_n$PPG$_n$PAS$_n$GS-3' (SEQ ID NO: 151), wherein:

each P is independently, and for each occurrence, a C-5 modified pyrimidine;
R is A or G;
each W is independently, and for each occurrence, A, T, or U;
each M is independently, and for each occurrence, A or C;
each S is independently, and for each occurrence, G or C;
each n is independently, and for each occurrence, 0 or 1; and
each m is independently, and for each occurrence, 0 or 1.

In some embodiments, an aptamer that binds GDF11 comprises a sequence selected from:

a) 5'-RW$_n$AC$_n$CPPGM$_m$MPPPA$_n$AC$_n$MC$_m$RW$_n$PPG$_n$PAS$_n$GC-3'; (SEQ ID NO: 111)

b) 5'-RW$_n$AC$_n$CPPGM$_m$MPPPA$_n$AC$_n$MC$_m$RW$_n$PPG$_n$PAS$_n$GS-3'; (SEQ ID NO: 152)

c) 5'-RW$_n$MC$_n$CPPGM$_m$MPPPA$_n$AC$_n$MC$_m$GW$_n$PPG$_n$PAS$_n$GC-3'; (SEQ ID NO: 112)

d) 5'-RW$_n$MC$_n$CPPGM$_m$MPPPA$_n$AC$_n$MC$_m$GW$_n$PPG$_n$PAS$_n$GS-3'; (SEQ ID NO: 153)

e) 5'-RMCPPGM$_m$MPPPA$_n$AC$_n$MC$_m$RW$_n$PPPAS$_n$GC-3'; (SEQ ID NO: 113)
and f) RMCPPGM$_m$MPPPA$_n$AC$_n$MC$_m$RW$_n$PPPAS$_n$GS-3'. (SEQ ID NO: 154)

In some embodiments of the sequences above, if R is G, the first W may be A, and wherein if R is A, the first W may be C. In some embodiments, at least 1, at least 2, at least 3, at least 4, at least 5, or at least 6 n are 0. In some embodiments, each n is 0. In some embodiments, at least 1, at least 2, at least 3 n are 1. In some embodiments, at least one m is 0. In some embodiments, at least one m is 1.

In some embodiments, an aptamer that binds GDF11 comprises the sequence 5'-CPPGMPPP-3' (SEQ ID NO: 114), wherein each P is independently, and for each occurrence, a C-5 modified pyrimidine, and wherein M is C or A. In some embodiments, an aptamer that binds GDF11 comprises the sequence 5'-PPPAGC-3'(SEQ ID NO: 115) or 5'-PPPAGG-3' (SEQ ID NO: 155), wherein each P is independently, and for each occurrence, a C-5 modified pyrimidine. In some embodiments, an aptamer that binds GDF11 comprises the sequence 5'-CPPGMPPPN$_x$PPPAGC-3' (SEQ ID NO: 116) or 5'-CPPGMPPPN$_x$PPPAGG-3' (SEQ ID NO: 160), wherein each P is independently, and for each occurrence, a C-5 modified pyrimidine, wherein x is 2, 3, 4, or 5, wherein M is C or A, and wherein each N is independently, and for each occurrence, selected from A, C, G, T, and U. In some embodiments, x is 3 or 4. In some embodiments, N$_x$ comprises the sequence 5'-AAG-3' or 5'-ACG-3' or 5'-AGG-3'.

In some embodiments, an aptamer that binds GDF11 comprises the sequence 5'-NNCPPGRPPPAMGPPPAGS-3' (SEQ ID NO: 141), wherein each P is independently, and for each occurrence, a C-5 modified pyrimidine, R is A or G; each N is independently, and for each occurrence, A, G, or C; M is A or C; and S is G or C.

In some embodiments, each P is independently, and for each occurrence, selected from:
5-(N-benzylcarboxyamide)-2'-deoxyuridine (BndU),
5-(N-benzylcarboxyamide)-2'-O-methyluridine,
5-(N-benzylcarboxyamide)-2'-fluorouridine,
5-(N-phenethylcarboxyamide)-2'-deoxyuridine (PEdU),
5-(N-thiophenylmethylcarboxyamide)-2'-deoxyuridine (ThdU),
5-(N-isobutylcarboxyamide)-2'-deoxyuridine (iBudU),
5-(N-tyrosylcarboxyamide)-2'-deoxyuridine (TyrdU),
5-(N-3,4-methylenedioxybenzylcarboxyamide)-2'-deoxyuridine (MBndU),
5-(N-4-fluorobenzylcarboxyamide)-2'-deoxyuridine (FBndU),
5-(N-3-phenylpropylcarboxyamide)-2'-deoxyuridine (PPdU),
5-(N-imidizolylethylcarboxyamide)-2'-deoxyuridine (ImdU),
5-(N-isobutylcarboxyamide)-2'-O-methyluridine,
5-(N-isobutylcarboxyamide)-2'-fluorouridine,
5-(N-tryptaminocarboxyamide)-2'-deoxyuridine (TrpdU),
5-(N-R-threoninylcarboxyamide)-2'-deoxyuridine (ThrdU),
5-(N-tryptaminocarboxyamide)-2'-O-methyluridine,
5-(N-tryptaminocarboxyamide)-2'-fluorouridine,
5-(N-[1-(3-trimethylamonium) propyl]carboxyamide)-2'-deoxyuridine chloride,
5-(N-naphthylmethylcarboxyamide)-2'-deoxyuridine (NapdU),
5-(N-naphthylmethylcarboxyamide)-2'-O-methyluridine,
5-(N-naphthylmethylcarboxyamide)-2'-fluorouridine,
5-(N-[1-(2,3-dihydroxypropyl)]carboxyamide)-2'-deoxyuridine),
5-(N-2-naphthylmethylcarboxyamide)-2'-deoxyuridine (2NapdU),
5-(N-2-naphthylmethylcarboxyamide)-2'-O-methyluridine,
5-(N-2-naphthylmethylcarboxyamide)-2'-fluorouridine,
5-(N-1-naphthylethylcarboxyamide)-2'-deoxyuridine (NEdU),
5-(N-1-naphthylethylcarboxyamide)-2'-O-methyluridine,
5-(N-1-naphthylethylcarboxyamide)-2'-fluorouridine,
5-(N-2-naphthylethylcarboxyamide)-2'-deoxyuridine (2NEdU),
5-(N-2-naphthylethylcarboxyamide)-2'-O-methyluridine,
5-(N-2-naphthylethylcarboxyamide)-2'-fluorouridine,
5-(N-3-benzofuranylethylcarboxyamide)-2'-deoxyuridine (BFdU),
5-(N-3-benzofuranylethylcarboxyamide)-2'-O-methyluridine,
5-(N-3-benzofuranylethylcarboxyamide)-2'-fluorouridine,
5-(N-3-benzothiophenylethylcarboxyamide)-2'-deoxyuridine (BTdU),
5-(N-3-benzothiophenylethylcarboxyamide)-2'-O-methyluridine, and
5-(N-3-benzothiophenylethylcarboxyamide)-2'-fluorouridine.

In some embodiments, each P is independently, and for each occurrence, selected from:
5-(N-1-naphthylmethylcarboxyamide)-2'-deoxyuridine (NapdU),
5-(N-1-naphthylmethylcarboxyamide)-2'-O-methyluridine,
5-(N-1-naphthylmethylcarboxyamide)-2'-fluorouridine,
5-(N-2-naphthylmethylcarboxyamide)-2'-deoxyuridine (2NapdU),
5-(N-2-naphthylmethylcarboxyamide)-2'-O-methyluridine,
5-(N-2-naphthylmethylcarboxyamide)-2'-fluorouridine,
5-(N-1-naphthylethylcarboxyamide)-2'-deoxyuridine (NEdU),
5-(N-1-naphthylethylcarboxyamide)-2'-O-methyluridine,
5-(N-1-naphthylethylcarboxyamide)-2'-fluorouridine,
5-(N-2-naphthylethylcarboxyamide)-2'-deoxyuridine (2NEdU),
5-(N-2-naphthylethylcarboxyamide)-2'-O-methyluridine,
5-(N-2-naphthylethylcarboxyamide)-2'-fluorouridine,
5-(N-3-benzofuranylethylcarboxyamide)-2'-deoxyuridine (BFdU),
5-(N-3-benzofuranylethylcarboxyamide)-2'-O-methyluridine,
5-(N-3-benzofuranylethylcarboxyamide)-2'-fluorouridine,
5-(N-3-benzothiophenylethylcarboxyamide)-2'-deoxyuridine (BTdU),
5-(N-3-benzothiophenylethylcarboxyamide)-2'-O-methyluridine, and
5-(N-3-benzothiophenylethylcarboxyamide)-2'-fluorouridine.

In some embodiments, at least 1, at least 2, at least 3, at least 4, at least 5, or at least 6 P are each independently selected from 5-(N-naphthylmethylcarboxyamide)-2'-deoxyuridine (NapdU), 5-(N-2-naphthylmethylcarboxyamide)-2'-O-methyluridine, and 5-(N-2-naphthylmethylcarboxyamide)-2'-fluorouridine.

In some embodiments, the aptamer comprises a sequence selected from SEQ ID NOs: 12, 13, 15 to 109, and 117 to 140. In some embodiments, the aptamer comprises a sequence selected from SEQ ID NOs: 12, 15, 26, 105 to 109, and 142 to 150.

In any of the embodiments described herein, the aptamer may consist of 18 to 200 nucleotides, or 18 to 150 nucleotides, or 18 to 100 nucleotides, or 18 to 75 nucleotides, or 18 to 50 nucleotides, or 20 to 150 nucleotides, or 20 to 100 nucleotides, or 20 to 75 nucleotides, or 20 to 50 nucleotides, wherein each nucleotide may, independently, be a modified or unmodified nucleotide. In any of the embodiments described herein, the aptamer may comprise a detectable label.

In some embodiments, GDF11 is human GDF11 and GDF8 is human GDF8. In some embodiments, GDF11 is mature human GDF11 comprising the sequence of SEQ ID NO: 118 and GDF8 is mature human GDF8 comprising the sequence of SEQ ID NO: 119.

In some embodiments, a method of detecting GDF11 in a sample is provided, comprising contacting proteins from the sample with an aptamer described herein. In some embodiments, the aptamer binds GDF8 with an affinity that is at least 10-fold weaker than the affinity for GDF11. In some embodiments, the aptamer does not bind GDF8.

In some embodiments, a method of determining whether a sample comprises GDF11, comprising contacting proteins from the sample with an aptamer described herein. In some embodiments, the sample comprises GDF8. In some embodiments, the method comprises contacting the sample with the aptamer under stringent conditions. In some embodiments, the stringent conditions comprise a polyanionic inhibitor. In some embodiments, the polyanionic inhibitor is selected from dextran sulfate, heparin, Z-block, poly-dI/dC, sonicated or sheared salmon sperm DNA, calf thymus DNA, and dNTPs.

In some embodiments, the sample is a sample from a human. In some embodiments, the sample is selected from blood, serum, plasma, saliva, urine, and a tissue sample. In some embodiments, the tissue sample is selected from heart muscle tissue, skeletal muscle tissue, pancreatic tissue, cartilage tissue and neural tissue.

In some embodiments, the proteins have been separated from at least one other component of the sample. In some embodiments, the proteins have not been separated from other components of the sample.

In some embodiments, compositions are provided comprising an aptamer described herein and proteins from a sample. In some embodiments, the sample comprises GDF8. In some embodiments, the composition comprises a polyanionic inhibitor. In some embodiments, the polyanionic inhibitor is selected from dextran sulfate, heparin, Z-block, poly-dI/dC, sonicated or sheared salmon sperm DNA, calf thymus DNA, and dNTPs. In some embodiments, the sample is a sample from a human. In some embodiments, the sample is selected from blood, serum, plasma, saliva, urine, and a tissue sample. In some embodiments, the tissue sample is selected from heart muscle tissue, skeletal muscle tissue, pancreatic tissue, cartilage tissue and neural tissue. In some embodiments, the proteins have been separated from at least one other component of the sample. In some embodiments, the proteins have not been separated from other components of the sample.

In another aspect, the aptamer is at least 25 nucleotides in length. In another aspect, the aptamer is at least 30 nucleotides in length. In another aspect, the aptamer is at least 40 nucleotides in length. In another aspect, the aptamer is from about 40 to about 100 nucleotides in length (or from 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nucleotides in length).

The present disclosure further provides a composition comprising an aptamer and a GDF11 protein, wherein the aptamer and the GDF11 protein are bound by a non-covalent interaction.

The foregoing and other objects, features, and advantages of the invention will become more apparent from the following detailed description, which proceeds with reference to the accompanying figures.

BRIEF DESCRIPTION OF THE DRAWINGS

FIG. 3 shows a truncation analysis of aptamer clone 12060-28_3 (50-mer sequence) and the binding affinity of each sequence for GDF11.

DETAILED DESCRIPTION

I. Terms and Methods

Figure 1:
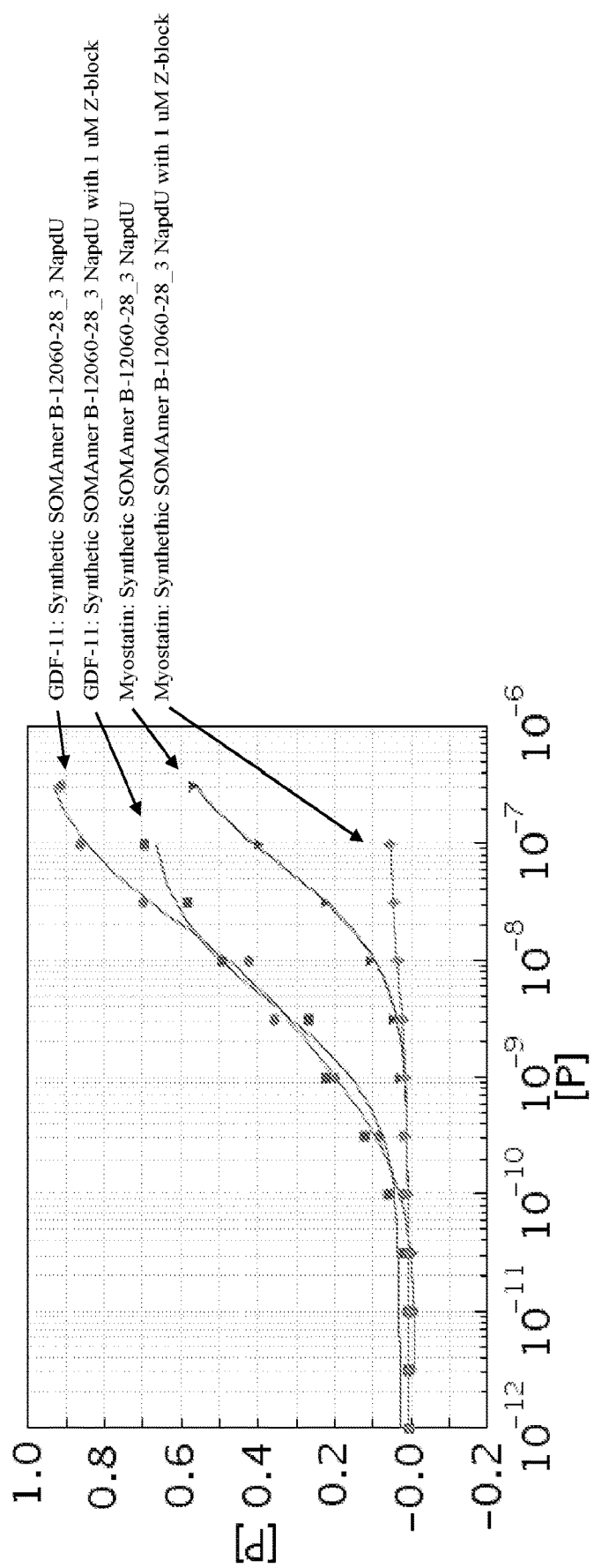
FIG. 1 shows a comparison of the binding affinities of aptamer clone 12060-28_3 for human GDF11 protein and human myostatin (GDF8) protein in the presence or absence of a polyanionic inhibitor (Z-block). The x-axis shows the concentrations for the respective proteins and the y-axis shows the percent of the aptamer bound to the protein (1.0 is 100%).

While the invention will be described in conjunction with certain representative embodiments, it will be understood that the invention is defined by the claims, and is not limited to those embodiments.

One skilled in the art will recognize many methods and materials similar or equivalent to those described herein may be used in the practice of the present invention. The present invention is in no way limited to the methods and materials described.

Unless defined otherwise, technical and scientific terms used herein have the meaning commonly understood by one of ordinary skill in the art to which this invention belongs. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). Although any methods, devices, and materials similar or equivalent to those described herein can be used in the practice of the invention, certain methods, devices, and materials are described herein.

All publications, published patent documents, and patent applications cited herein are hereby incorporated by reference to the same extent as though each individual publication, published patent document, or patent application was specifically and individually indicated as being incorporated by reference.

As used in this application, including the appended claims, the singular forms "a," "an," and "the" include the plural, unless the context clearly dictates otherwise, and may be used interchangeably with "at least one" and "one or more." Thus, reference to "an aptamer" includes mixtures of aptamers, reference to "a probe" includes mixtures of probes, and the like.

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements may include other elements not expressly listed.

It is further to be understood that all base sizes or amino acid sizes, and all molecular weight or molecular mass values, given for nucleic acids or polypeptides are approximate, and are provided for description.

In order to facilitate review of the various embodiments of the disclosure, the following explanations of specific terms are provided:

Aptamer: As used herein, an "aptamer" refers to a nucleic acid that has a specific binding affinity for a target molecule. It is recognized that affinity interactions are a matter of degree; however, in this context, the "specific binding affinity" of an aptamer for its target means that the aptamer binds to its target generally with a much higher degree of affinity than it binds to other components in a test sample. An "aptamer" is a set of copies of one type or species of nucleic acid molecule that has a particular nucleotide sequence. An aptamer can include any suitable number of nucleotides, including any number of chemically modified nucleotides. "Aptamers" refers to more than one such set of molecules. Different aptamers can have either the same or different numbers of nucleotides. Aptamers can be DNA or RNA or chemically modified nucleic acids and can be single stranded, double stranded, or contain double stranded regions, and can include higher ordered structures. An aptamer can also be a photoaptamer, where a photoreactive or chemically reactive functional group is included in the aptamer to allow it to be covalently linked to its corresponding target. Any of the aptamer methods disclosed herein can include the use of two or more aptamers that specifically bind the same target molecule. As further described below, an aptamer may include a tag. If an aptamer includes a tag, all copies of the aptamer need not have the same tag. Moreover, if different aptamers each include a tag, these different aptamers can have either the same tag or a different tag.

An aptamer can be identified using any known method, including the SELEX process. Once identified, an aptamer can be prepared or synthesized in accordance with any known method, including chemical synthetic methods and enzymatic synthetic methods.

GDF11 Aptamer: GDF11 aptamer, as used herein, refers to an aptamer that is capable of binding to a mature GDF11 protein. A nonlimiting exemplary mature human GDF11 protein is shown below (amino acids 299 to 407 of UniProtKB/Swiss-Prot: O95390.1):

```
                                         (SEQ ID NO: 118)
L GLDCDEHSSE SRCCRYPLTV DFEAFGWDWI IAPKRYKANY

CSGQCEYMFM QKYPHTHLVQ QANPRGSAGP CCTPTKMSPI

NMLYFNDKQQ IIYGKIPGMV VDRCGCS.
```

In some embodiments, a GDF11 aptamer binds GDF8 with an affinity that is at least 10-fold weaker than the affinity for GDF11. In some embodiments, a GDF11 aptamer does not bind GDF8. A nonlimiting exemplary mature human GDF8 protein is shown below (amino acids 267 to 375 of UniProtKB/Swiss-Prot: O14793.1):

```
                                         (SEQ ID NO: 119)
FGL DCDEHSTESR CCRYPLTVDF EAFGWDWIIA PKRYKANYCS

GECEFVFLQK YPHTHLVHQA NPRGSAGPCC TPTKMSPINM

LYFNGKEQII YGKIPAMVVD RCGCS.
```

Inhibit: The term inhibit, as used herein, means to prevent or reduce the expression of a peptide or a polypeptide to an extent that the peptide or polypeptide no longer has measurable activity or bioactivity; or to reduce the stability and/or reduce or prevent the activity of a peptide or a polypeptide to an extent that the peptide or polypeptide no longer has measurable activity or bioactivity. As described herein, the protein that may be inhibited is GDF11.

Nucleic acid: As used herein, "nucleic acid," "oligonucleotide," and "polynucleotide" are used interchangeably to refer to a polymer of nucleotides and include DNA, RNA, DNA/RNA hybrids and modifications of these kinds of nucleic acids, oligonucleotides and polynucleotides, wherein the attachment of various entities or moieties to the nucleotide units at any position are included. The terms "polynucleotide," "oligonucleotide," and "nucleic acid" include double- or single-stranded molecules as well as triple-helical molecules. Nucleic acid, oligonucleotide, and polynucleotide are broader terms than the term aptamer and, thus, the terms nucleic acid, oligonucleotide, and polynucleotide include polymers of nucleotides that are aptamers but the terms nucleic acid, oligonucleotide, and polynucleotide are not limited to aptamers.

Modified: As used herein, the terms "modify", "modified", "modification", and any variations thereof, when used in reference to an oligonucleotide, means that at least one of the four constituent nucleotide bases (i.e., A, G, T/U, and C) of the oligonucleotide is an analog or ester of a naturally occurring nucleotide. In some embodiments, the modified nucleotide confers nuclease resistance to the oligonucleotide. In some embodiments, the modified nucleotides lead to predominantly hydrophobic interactions of aptamers with protein targets resulting in high binding efficiency and stable co-crystal complexes. A pyrimidine with a substitution at the C-5 position is an example of a modified nucleotide. Modifications can include backbone modifications, methylations, unusual base-pairing combinations such as the isobases isocytidine and isoguanidine, and the like. Modifications can also include 3' and 5' modifications, such as capping. Other modifications can include substitution of one or more of the naturally occurring nucleotides with an analog, internucleotide modifications such as, for example, those with uncharged linkages (e.g., methyl phosphonates, phosphotriesters, phosphoamidates, carbamates, etc.) and those with charged linkages (e.g., phosphorothioates, phosphorodithioates, etc.), those with intercalators (e.g., acridine, psoralen, etc.), those containing chelators (e.g., metals, radioactive metals, boron, oxidative metals, etc.), those containing alkylators, and those with modified linkages (e.g., alpha anomeric nucleic acids, etc.). Further, any of the hydroxyl groups ordinarily present on the sugar of a nucleotide may be replaced by a phosphonate group or a phosphate group; protected by standard protecting groups; or activated to prepare additional linkages to additional nucleotides or to a solid support. The 5' and 3' terminal OH groups can be phosphorylated or substituted with amines, organic capping group moieties of from about 1 to about 20 carbon atoms, polyethylene glycol (PEG) polymers, in some embodiments, ranging from about 10 to about 80 kDa, PEG polymers, in some embodiments, ranging from about 20 to about 60 kDa, or other hydrophilic or hydrophobic biological or synthetic polymers. In one embodiment, modifications are of the C-5 position of pyrimidines. These modifications can be produced through an amide linkage directly at the C-5 position or by other types of linkages.

Polynucleotides can also contain analogous forms of ribose or deoxyribose sugars that are generally known in the art, including 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. As noted above, one or more phosphodiester linkages may be replaced by alternative linking groups. These alternative linking groups include embodiments wherein phosphate is replaced by P(O)S ("thioate"), P(S)S ("dithioate"), (O)NR2 ("amidate"), P(O)R, P(O)OR', CO or CH2 ("formacetal"), in which each R or R' is independently H or substituted or unsubstituted alkyl (1-20 C) optionally containing an ether (—O—) linkage, aryl, alkenyl, cycloalky, cycloalkenyl or araldyl. Not all linkages in a polynucleotide need be identical. Substitution of analogous forms of sugars, purines, and pyrimidines can be advantageous in designing a final product, as can alternative backbone structures like a polyamide backbone, for example.

Nuclease: As used herein, the term "nuclease" refers to an enzyme capable of cleaving the phosphodiester bond between nucleotide subunits of an oligonucleotide. As used herein, the term "endonuclease" refers to an enzyme that cleaves phosphodiester bond(s) at a site internal to the oligonucleotide. As used herein, the term "exonuclease" refers to an enzyme which cleaves phosphodiester bond(s) linking the end nucleotides of an oligonucleotide. Biological fluids typically contain a mixture of both endonucleases and exonucleases.

As used herein, the terms "nuclease resistant" and "nuclease resistance" refers to the reduced ability of an oligonucleotide to serve as a substrate for an endo- or exonuclease, such that, when contacted with such an enzyme, the oligonucleotide is either not degraded or is degraded more slowly than an oligonucleotide composed of unmodified nucleotides.

C-5 Modified Pyrimidine: As used herein, the term "C-5 modified pyrimidine" refers to a pyrimidine with a modification at the C-5 position including, but not limited to, those moieties illustrated herein. Examples of a C-5 modified pyrimidine include those described in U.S. Pat. Nos. 5,719,273 and 5,945,527. Examples of a C-5 modification include substitution of deoxyuridine at the C-5 position with a substituent independently selected from: benzylcarboxyamide (alternatively benzylaminocarbonyl) (Bn), naphthylmethylcarboxyamide (alternatively naphthylmethylaminocarbonyl) (Nap), tryptaminocarboxyamide (alternatively tryptaminocarbonyl) (Trp), phenethylcarboxyamide (alternatively phenethylamino carbonyl) (Pe), thiophenylmethylcarboxyamide (alternatively thiophenylmethylaminocarbonyl) (Th) and isobutylcarboxyamide (alternatively isobutylaminocarbonyl) (iBu) as illustrated immediately below.

Chemical modifications of a C-5 modified pyrimidine can also be combined with, singly or in any combination, 2'-position sugar modifications, modifications at exocyclic amines, and substitution of 4-thiouridine and the like.

Representative C-5 modified pyrimidines include: 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-isobutylcarboxyamide)-2'-deoxyuridine (iBudU), 5-(N-isobutylcarboxyamide)-2'-O-methyluridine, 5-(N-phenethylcarboxyamide)-2'-deoxyuridine (PedU), 5-(N-thiophenylmethylcarboxyamide)-2'-deoxyuridine (ThdU), 5-(N-isobutylcarboxyamide)-2'-fluorouridine, 5-(N-tryptaminocarboxyamide)-2'-deoxyuridine (TrpdU), 5-(N-tryptaminocarboxyamide)-2'-O-methyluridine, 5-(N-tryptaminocarboxyamide)-2'-fluorouridine, 5-(N-[1-(3-trimethylamonium) propyl]carboxyamide)-2'-deoxyuridine chloride, 5-(N-naphthylmethylcarboxyamide)-2'-deoxyuridine (NapdU), 5-(N-naphthylmethylcarboxyamide)-2'-O-methyluridine, 5-(N-naphthylmethylcarboxyamide)-2'-fluorouridine or 5-(N-[1-(2,3-dihydroxypropyl]carboxyamide)-2'-deoxyuridine).

Nucleotides can be modified either before or after synthesis of an oligonucleotide. A sequence of nucleotides in an oligonucleotide may be interrupted by one or more non-nucleotide components. A modified oligonucleotide may be further modified after polymerization, such as, for example, by conjugation with any suitable labeling component.

As used herein, the term "at least one pyrimidine," when referring to modifications of a nucleic acid, refers to one, several, or all pyrimidines in the nucleic acid, indicating that any or all occurrences of any or all of C, T, or U in a nucleic acid may be modified or not.

Modulate: The term modulate, as used herein, means to alter the expression level of a peptide, protein or polypeptide by increasing or decreasing its expression level relative to a reference expression level, and/or alter the stability and/or activity of a peptide, protein or polypeptide by increasing or decreasing its stability and/or activity level relative to a reference stability and/or activity level.

Pharmaceutically Acceptable: Pharmaceutically acceptable, as used herein, means approved by a regulatory agency of a federal or a state government or listed in the U.S. Pharmacopoeia or other generally recognized pharmacopoeia for use in animals and, more particularly, in humans.

Pharmaceutically Acceptable Salt: Pharmaceutically acceptable salt or salt of a compound (e.g., aptamer), as used herein, refers to a product that contains an ionic bond and is typically produced by reacting the compound with either an acid or a base, suitable for administering to an individual. A pharmaceutically acceptable salt can include, but is not limited to, acid addition salts including hydrochlorides, hydrobromides, phosphates, sulphates, hydrogen sulphates, alkylsulphonates, arylsulphonates, arylalkylsulfonates, acetates, benzoates, citrates, maleates, fumarates, succinates, lactates, and tartrates; alkali metal cations such as Li, Na, K, alkali earth metal salts such as Mg or Ca, or organic amine salts.

Pharmaceutical Composition: Pharmaceutical composition, as used herein, refers to formulation comprising a GDF11 aptamer in a form suitable for administration to an individual. A pharmaceutical composition is typically formulated to be compatible with its intended route of administration. Examples of routes of administration include, but are not limited to, oral and parenteral, e.g., intravenous, intradermal, subcutaneous, inhalation, topical, transdermal, transmucosal, and rectal administration.

SELEX: The terms "SELEX" and "SELEX process" are used interchangeably herein to refer generally to a combination of (1) the selection of aptamers that interact with a target molecule in a desirable manner, for example binding with high affinity to a protein, with (2) the amplification of those selected nucleic acids. The SELEX process can be used to identify aptamers with high affinity to a specific target or biomarker.

Sequence Identity: Sequence identity, as used herein, in the context of two or more nucleic acid sequences is a function of the number of identical nucleotide positions shared by the sequences (i.e., % identity=number of identical positions/total number of positions ×100), taking into account the number of gaps, and the length of each gap that needs to be introduced to optimize alignment of two or more sequences. The comparison of sequences and determination of percent identity between two or more sequences can be accomplished using a mathematical algorithm, such as BLAST and Gapped BLAST programs at their default parameters (e.g., Altschul et al., *J. Mol. Biol.* 215:403, 1990; see also BLASTN at www.ncbi.nlm.nih.gov/BLAST). For sequence comparisons, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith and Waterman, Adv. Appl. Math., 2:482, 1981, by the homology alignment algorithm of Needleman and Wunsch, J. Mol. Biol., 48:443, 1970, by the search for similarity method of Pearson and Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel, F. M. et al., Current Protocols in Molecular Biology, pub. by Greene Publishing Assoc. and Wiley-Interscience (1987)). As used herein, when describing the percent identity of a nucleic acid, such as a GDF11 aptamer, the sequence of which is at least, for example, about 95% identical to a reference nucleotide sequence, it is intended that the nucleic acid sequence is identical to the reference sequence except that the nucleic acid sequence may include up to five point mutations per each 100 nucleotides of the reference nucleic acid sequence. In other words, to obtain a desired nucleic acid sequence, the sequence of which is at least about 95% identical to a reference nucleic acid sequence, up to 5% of the nucleotides in the reference sequence may be deleted or substituted with another nucleotide, or some number of nucleotides up to 5% of the total number of nucleotides in the reference sequence may be inserted into the reference sequence (referred to herein as an insertion). These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

SOMAmer: The term SOMAmer, as used herein, refers to an aptamer having improved off-rate characteristics. SOMAmers are alternatively referred to as Slow Off-Rate Modified Aptamers, and may be selected via the improved SELEX methods described in U.S. Publication No. 20090004667, entitled "Method for Generating Aptamers with Improved Off-Rates", which is incorporated by reference in its entirety. In some embodiments, a slow off-rate aptamer (including an aptamers comprising at least one nucleotide with a hydrophobic modification) has an off-rate (t½) of ≥2 minutes, ≥4 minutes, ≥5 minutes, ≥8 minutes, ≥10 minutes, ≥15 minutes≥30 minutes, ≥60 minutes, ≥90 minutes, ≥120 minutes, ≥150 minutes, ≥180 minutes, ≥210 minutes, or ≥240 minutes.

Target Molecule: "Target", "target molecule", and "analyte" are used interchangeably herein to refer to any molecule of interest that may be present in a sample. The term includes any minor variation of a particular molecule, such as, in the case of a protein, for example, minor variations in amino acid sequence, disulfide bond formation, glycosylation, lipidation, acetylation, phosphorylation, or any other manipulation or modification, such as conjugation with a labeling component, which does not substantially alter the identity of the molecule. A "target molecule", "target", or "analyte" refers to a set of copies of one type or species of molecule or multi-molecular structure. "Target molecules", "targets", and "analytes" refer to more than one type or species of molecule or multi-molecular structure. Exemplary target molecules include proteins, polypeptides, nucleic acids, carbohydrates, lipids, polysaccharides, glycoproteins, hormones, receptors, antigens, antibodies, affybodies, antibody mimics, viruses, pathogens, toxic substances, substrates, metabolites, transition state analogs, cofactors, inhibitors, drugs, dyes, nutrients, growth factors, cells, tissues, and any fragment or portion of any of the foregoing. In some embodiments, a target molecule is a protein, in which case the target molecule may be referred to as a "target protein."

Polyanionic inhibitor: A polyanionic inhibitor is an inhibitor molecule that comprises or mimics the poyanionic phosphate backbone of a nucleic acid molecule. In some embodiments, a polyanionic inhibitor is included in a binding reaction with an aptamer to increase the stringency of the binding conditions. Nonlimiting exemplary polyanionic inhibitors include dextran sulfate, heparin, Z-block, poly-dI/dC, sonicated or sheared salmon sperm DNA, calf thymus DNA, dNTPs, and the like.

Z-Block: Z-block as used herein is a single-stranded oligonucleotide of sequence 5'-(AC-BndU-BndU)$_7$-AC-3', where BndU indicates a benzyl-substituted deoxyuridine residue. Z-block may be synthesized using conventional phosphoramidite chemistry Ranges provided herein are understood to be shorthand for all of the values within the range. For example, a range of 1 to 50 is understood to include any number, combination of numbers, or sub-range from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise). Any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, "about" or "consisting essentially of mean±20% of the indicated range, value, or structure, unless otherwise indicated. As used herein, the terms "include" and "comprise" are open ended and are used synonymously. It should be understood that the terms "a" and "an" as used herein refer to "one or more" of the enumerated components. The use of the alternative (e.g., "or") should be understood to mean either one, both, or any combination thereof of the alternatives.

II. Overview

A. Growth Differentiation Factor 11 (GDF11) and Myostatin (GDF8) Proteins

The native mature forms of GDF11 and myostatin are homodimers and are about 90% identical by sequence alignment, with 98 of 109 matching amino acid residues. See amino acid sequence alignment for GDF11 (Protein ID 095390; amino acids 1 to 407; SEQ ID NO: 4) and myostatin (Protein ID 014793; amino acids 1 to 375; SEQ ID NO: 5), mature form indicated by gray bar. The alignment of the amino acid sequences of GDF11 and myostatin prepropeptides are shown below. The mature protein portions are highlighted with the gray bar.

```
---MVLAAPLLLGFLLLALELRPRGEAAEGPAAAAAAAAAAAAAGVGCERSSRPAPSVAP   57   095390   GDF11_HUMAN
MQKLQLCVYIY-LFMLI--V--------AGPVDL---------------NENSEQKENVE   34   014793   GDF8_HUMAN
   :*...  :   *:*:           **.                ...    . .

EPDGCPVCVWRQHSRELRLESIKSQILSKLRLKEAPNISREVVKQLLPKAPPLQQILDLM  117   095390   GDF11_HUMAN
KEGLCNACTWRQNTKSSRIEAIKIQILSKLRLETAPNISKDVIRQLLPKAPPLRELIDQY   94   014793   GDF8_HUMAN
:    * .*.***.::. *:*:** ********: *****::*:;**********::::* :

DFQGDALQPEDFLEEDEYHATTETVISMAQETDPAVQTDGSPLCCHFHFSPKVMFTKVLK  177   095390   GDF11_HUMAN
DVQRDDS-SDGSLEDDDYHATTETIITMPTESDFLMQVDGKPKCCFFKFSSKIQYNKVVK  153   014793   GDF8_HUMAN
*.* *     : **.*:*******.*:.*   *:*   :*.**.* **.*:** *: :.**:*

AQLWVYLRPVPRPATVYLQILRLKPLTGEGTAGGGGGGRRHIRIRSLKIELHSRSGHWQS  237   095390   GDF11_HUMAN
AQLWIYLRPVETPTTVFVQILRLIKPMKD--------GTRYTGIRSLKLDMNPGTGIWQS  205   014793   GDF8_HUMAN
****:*****  *:**::*****    :           * *:   *****:::.   :* ***

IDFKQVLHSWFRQPQSNWGIEINAFDPSGTDLAVTSLGPGAEGLMPFMELRVLENTKRSR  297   095390   GDF11_HUMAN
IDVKTVLQNWLKQPESNLGIEIKALDENGHDLAVTFPGPGEDGLNPFLEVKVTDTPKRSR  265   014793   GDF8_HUMAN
**.* **:.*::**:** ****:*:* .* ***** ***.**.**:*::* :. ****

RNLGLDCDEHSSESRCCRYPLTVDFEAFGWDWIIAPKRYKANYCSGQCEYMFMQKYPHTH  357   095380   GDF11_HUMAN
RDFGLDCDEHSTESRCCRYPLTVDFEAFGWDWIIAPKRYKANYCSGECEFVFLQKYPHTH  325   014793   GDF8_HUMAN
*::********.****************************************.**::*:*.*******

LVQQANPRGSAGPCCTPTKMSPINMLYFNDKQQIIYGKIPGMVVDRCGCS  407   095390   GDF11_HUMAN
LVHQANPRGSAGPCCTPTKMSPINMLYFNGKEQIIYGKIPAMVVDRCGCS  375   014793   GDF8_HUMAN
**:*************************.*:******.*********
```

GDF11 and GDF8 are thought to share common ancestry and common regulatory mechanism, yet have diverged with regard to their tissue specificity (primarily heart and muscle, respectively).

Mature GDF11 is 100% identical between human and mouse, and 99% identical in rat. Amino acid sequence alignment of human, mouse and rat GDF11 protein (mature) is show below. Human GDF11 Protein ID is 095390; an exemplary human mature GDF11 is shown below; SEQ ID NO: 6). Mouse GDF11 Protein ID is Q9Z1W4; an exemplary mouse mature GDF8 is shown below; SEQ ID NO: 7). Rat GDF11 Protein ID is Q9Z217; an exemplary rat mature GDF8 is shown below; SEQ ID NO: 8).

```
  1 NLGLDCDEHSSESRCCRYPLTVDFEAFGWDWIIAPKRYKANYCSGQCEYMFMQKYPHTHL  60   095390  GDF11_HUMAN
  1 NLGLDCDEHSSESRCCRYPLTVDFEAFGWDWIIAPKRYKANYCSGQCEYMFMQKYPHTHL  60   Q9Z1W4   GDF11_MOUSE
  1 NLGLDCDEHSSESRCCRYPLTVDFEASGWDWIIAPKRYKANYCSGQCEYMFMQKYPHTHL  60   Q9Z217   GDF11_RAT
    *************************  ********************************

61 VQQANPRGSAGPCCTPTKMSPINMLYFNDKQQIIYGKIPGMVVDRCGCS  109   095390  GDF11_HUMAN
 61 VQQANPRGSAGPCCTPTKMSPINMLYFNDKQQIIYGKIPGMVVDRCGCS  109   Q9Z1WF   GDF11_MOUSE
 61 VQQANPRGSAGPCCTPTKMSPINMLYFNDKQQIIYGKIPGMVV------  103   Q9Z217   GDF11_RAT
    ******************************************
```

Myostatin (GDF8) is 100% identical between human, mouse, and rat. Amino acid sequence alignment of human, mouse and rat myostatin protein (mature) is show below. Human myostatin (GDF8) Protein ID is 014793; an exemplary human mature GDF8 is shown below; SEQ ID NO: 9). Mouse GDF8 Protein ID is 008689; an exemplary mouse mature GDF8 is shown below; SEQ ID NO: 10). Rat GDF11 Protein ID is 035312; an exemplary rat mature GDF8 is shown below; SEQ ID NO: 11).

molecule, allowing the formation of nucleic acid-target complexes to occur, and performing a slow off-rate enrichment process wherein nucleic acid-target complexes with fast dissociation rates will dissociate and not reform, while complexes with slow dissociation rates will remain intact. Additionally, the methods include the use of modified nucleotides in the production of candidate nucleic acid mixtures to generate aptamers or SOMAmers with improved off-rate performance.

```
  1 DFGLDCDEHSTESRCCRYPLTVDFEAFGWDWIIAPKRYKANYCSGECEFVFLQKYPHTHL  60 014793 GDF8_HUMAN
  1 DFGLDCDEHSTESRCCRYPLTVDFEAFGWDWIIAPKRYKANYCSGECEFVFLQKYPHTHL  60 008689 GDF8_MOUSE
  1 DFGLDCDEHSTESRCCRYPLTVDFEAFGWDWIIAPKRYKANYCSGECEFVFLQKYPHTHL  60 035312 GDF8_RAT
    ***********************************************************

61 VHQANPRGSAGPCCTPTKMSPINMLYFNGKEQIIYGKIPAMVVDRCGCS 109 014793 GDF8_HUMAN
 61 VHQANPRGSAGPCCTPTKMSPINMLYFNGKEQIIYGKIPAMVVDRCGCS 109 008689 GDF8_MOUSE
 61 VHQANPRGSAGPCCTPTKMSPINMLYFNGKEQIIYGKIPAMVVDRCGCS 109 035312 GDF8_RAT
    ************************************************
```

B. SELEX

SELEX generally includes preparing a candidate mixture of nucleic acids, binding of the candidate mixture to the desired target molecule to form an affinity complex, separating the affinity complexes from the unbound candidate nucleic acids, separating and isolating the nucleic acid from the affinity complex, purifying the nucleic acid, and identifying a specific aptamer sequence. The process may include multiple rounds to further refine the affinity of the selected aptamer. The process can include amplification steps at one or more points in the process. See, e.g., U.S. Pat. No. 5,475,096, entitled "Nucleic Acid Ligands". The SELEX process can be used to generate an aptamer that covalently binds its target as well as an aptamer that non-covalently binds its target. See, e.g., U.S. Pat. No. 5,705,337 entitled "Systematic Evolution of Nucleic Acid Ligands by Exponential Enrichment: Chemi-SELEX."

The SELEX process can be used to identify high-affinity aptamers containing modified nucleotides that confer improved characteristics on the aptamer, such as, for example, improved in vivo stability or improved delivery characteristics. Examples of such modifications include chemical substitutions at the ribose and/or phosphate and/or base positions. SELEX process-identified aptamers containing modified nucleotides are described in U.S. Pat. No. 5,660,985, entitled "High Affinity Nucleic Acid Ligands Containing Modified Nucleotides", which describes oligonucleotides containing nucleotide derivatives chemically modified at the 5'- and 2'-positions of pyrimidines. U.S. Pat. No. 5,580,737, see supra, describes highly specific aptamers containing one or more nucleotides modified with 2'-amino (2'NH2), 2'-fluoro (2'-F), and/or 2'-O-methyl (2'-OMe). See also, U.S. Patent Application Publication 20090098549, entitled "SELEX and PHOTOSELEX", which describes nucleic acid libraries having expanded physical and chemical properties and their use in SELEX and photoSELEX.

SELEX can also be used to identify aptamers that have desirable off-rate characteristics. See U.S. Patent Application Publication 20090004667, entitled "Method for Generating Aptamers with Improved Off-Rates", which describes improved SELEX methods for generating aptamers that can bind to target molecules. As mentioned above, these slow off-rate aptamers are known as "SOMAmers." Methods for producing aptamers or SOMAmers and photoaptamers or SOMAmers having slower rates of dissociation from their respective target molecules are described. The methods involve contacting the candidate mixture with the target A variation of this assay employs aptamers that include photoreactive functional groups that enable the aptamers to covalently bind or "photocrosslink" their target molecules. See, e.g., U.S. Pat. No. 6,544,776 entitled "Nucleic Acid Ligand Diagnostic Biochip". These photoreactive aptamers are also referred to as photoaptamers. See, e.g., U.S. Pat. Nos. 5,763,177, 6,001,577, and 6,291,184, each of which is entitled "Systematic Evolution of Nucleic Acid Ligands by Exponential Enrichment: Photoselection of Nucleic Acid Ligands and Solution SELEX"; see also, e.g., U.S. Pat. No. 6,458,539, entitled "Photoselection of Nucleic Acid Ligands". After the microarray is contacted with the sample and the photoaptamers have had an opportunity to bind to their target molecules, the photoaptamers are photoactivated, and the solid support is washed to remove any non-specifically bound molecules. Harsh wash conditions may be used, since target molecules that are bound to the photoaptamers are generally not removed, due to the covalent bonds created by the photoactivated functional group(s) on the photoaptamers.

In both of these assay formats, the aptamers or SOMAmers are immobilized on the solid support prior to being contacted with the sample. Under certain circumstances, however, immobilization of the aptamers or SOMAmers prior to contact with the sample may not provide an optimal assay. For example, pre-immobilization of the aptamers or SOMAmers may result in inefficient mixing of the aptamers or SOMAmers with the target molecules on the surface of the solid support, perhaps leading to lengthy reaction times and, therefore, extended incubation periods to permit efficient binding of the aptamers or SOMAmers to their target molecules. Further, when photoaptamers or photoSOMAmers are employed in the assay and depending upon the material utilized as a solid support, the solid support may tend to scatter or absorb the light used to effect the formation of covalent bonds between the photoaptamers or photoSOMAmers and their target molecules. Moreover, depending upon the method employed, detection of target molecules bound to their aptamers or photoSOMAmers can be subject to imprecision, since the surface of the solid support may also be exposed to and affected by any labeling agents that are used. Finally, immobilization of the aptamers or SOMAmers on the solid support generally involves an aptamer or SOMAmer-preparation step (i.e., the immobilization) prior to exposure of the aptamers or SOMAmers to the sample, and this preparation step may affect the activity or functionality of the aptamers or SOMAmers.

SOMAmer assays that permit a SOMAmer to capture its target in solution and then employ separation steps that are designed to remove specific components of the SOMAmer-target mixture prior to detection have also been described (see U.S. Patent Application Publication 20090042206, entitled "Multiplexed Analyses of Test Samples"). The described SOMAmer assay methods enable the detection and quantification of a non-nucleic acid target (e.g., a protein target) in a test sample by detecting and quantifying a nucleic acid (i.e., a SOMAmer). The described methods create a nucleic acid surrogate (i.e., the SOMAmer) for detecting and quantifying a non-nucleic acid target, thus allowing the wide variety of nucleic acid technologies, including amplification, to be applied to a broader range of desired targets, including protein targets.

Embodiments of the SELEX process in which the target is a peptide are described in U.S. Pat. No. 6,376,190, entitled "Modified SELEX Processes Without Purified Protein." In the instant case, the target is the GDF11 protein.

C. Chemically Modified Aptamers

Aptamers may contain modified nucleotides that improve it properties and characteristics. Non-limiting examples of such improvements include, in vivo stability, stability against degradation, binding affinity for its target, and/or improved delivery characteristics.

Examples of such modifications include chemical substitutions at the ribose and/or phosphate and/or base positions of a nucleotide. SELEX process-identified aptamers containing modified nucleotides are described in U.S. Pat. No. 5,660,985, entitled "High Affinity Nucleic Acid Ligands Containing Modified Nucleotides," which describes oligonucleotides containing nucleotide derivatives chemically modified at the 5'- and 2'-positions of pyrimidines. U.S. Pat. No. 5,580,737, see supra, describes highly specific aptamers containing one or more nucleotides modified with 2'-amino (2'NH2), 2'-fluoro (2'-F), and/or 2'-O-methyl (2'-OMe). See also, U.S. Patent Application Publication No. 20090098549, entitled "SELEX and PHOTOSELEX," which describes nucleic acid libraries having expanded physical and chemical properties and their use in SELEX and photoSELEX.

Specific examples of a C-5 modification include substitution of deoxyuridine at the C-5 position with a substituent independently selected from: benzylcarboxyamide (alternatively benzylaminocarbonyl) (Bn), naphthylmethylcarboxyamide (alternatively naphthylmethylaminocarbonyl) (Nap), tryptaminocarboxyamide (alternatively tryptaminocarbonyl) (Trp), and isobutylcarboxyamide (alternatively isobutylaminocarbonyl) (iBu) as illustrated immediately below.

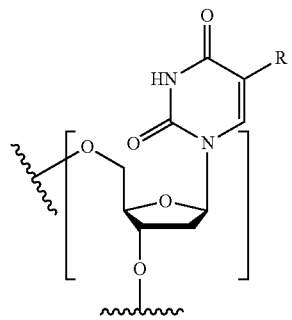

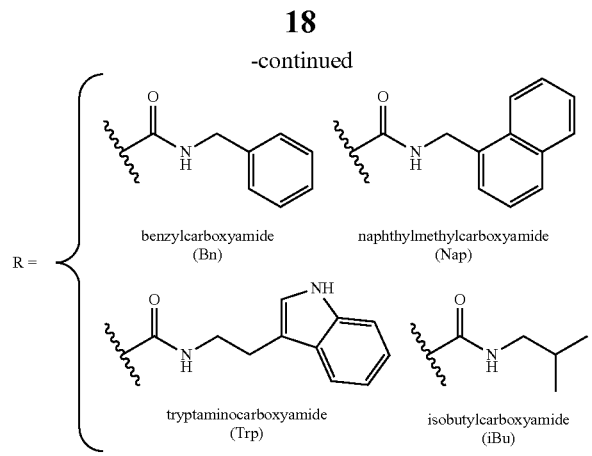

Chemical modifications of a C-5 modified pyrimidine can also be combined with, singly or in any combination, 2'-position sugar modifications, modifications at exocyclic amines, and substitution of 4-thiouridine and the like.

Representative C-5 modified pyrimidines include: 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-isobutylcarboxyamide)-2'-deoxyuridine (iBudU), 5-(N-isobutylcarboxyamide)-2'-O-methyluridine, 5-(N-isobutylcarboxyamide)-2'-fluorouridine, 5-(N-tryptaminocarboxyamide)-2'-deoxyuridine (TrpdU), 5-(N-tryptaminocarboxyamide)-2'-O-methyluridine, 5-(N-tryptaminocarboxyamide)-2'-fluorouridine, 5-(N-[1-(3-trimethylamonium) propyl]carboxyamide)-2'-deoxyuridine chloride, 5-(N-naphthylmethylcarboxyamide)-2'-deoxyuridine (NapdU), 5-(N-naphthylmethylcarboxyamide)-2'-0-methyluridine, 5-(N-naphthylmethylcarboxyamide)-2'-fluorouridine or 5-(N-[1-(2,3-dihydroxypropyl)]carboxyamide)-2'-deoxyuridine).

If present, a modification to the nucleotide structure can be imparted before or after assembly of the polynucleotide. A sequence of nucleotides can be interrupted by non-nucleotide components. A polynucleotide can be further modified after polymerization, such as by conjugation with a labeling component.

Additional non-limiting examples of modified nucleotides (e.g., C-5 modified pyrimidine) that may be incorporated into the nucleic acid sequences of the present disclosure include the following:

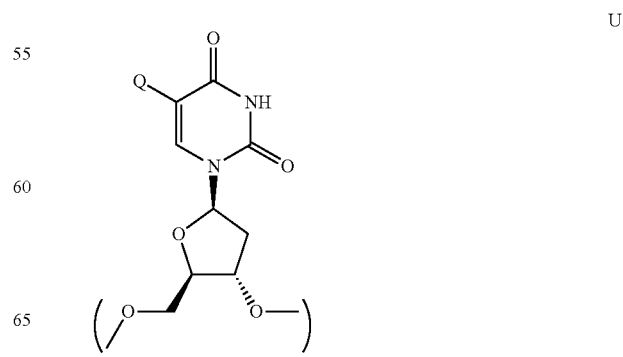

19
-continued
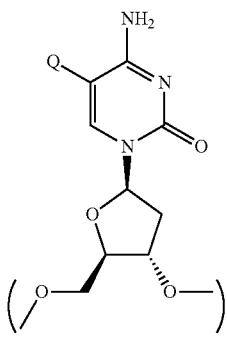
20
-continued
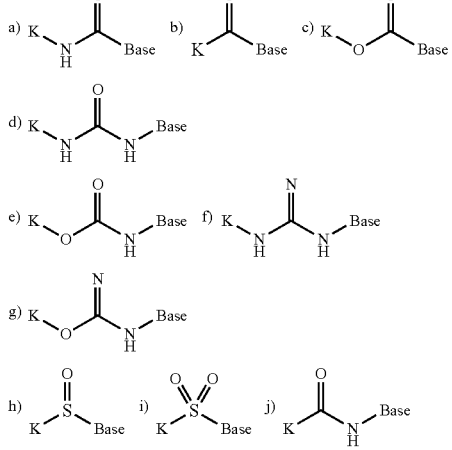
Base = Uridine (U) or Cytidine(C) (attachment is to the 5-position)
K = R' group plus $(CH_2)_n$ connecting group, where n = 0-3
R' is defined as follows:
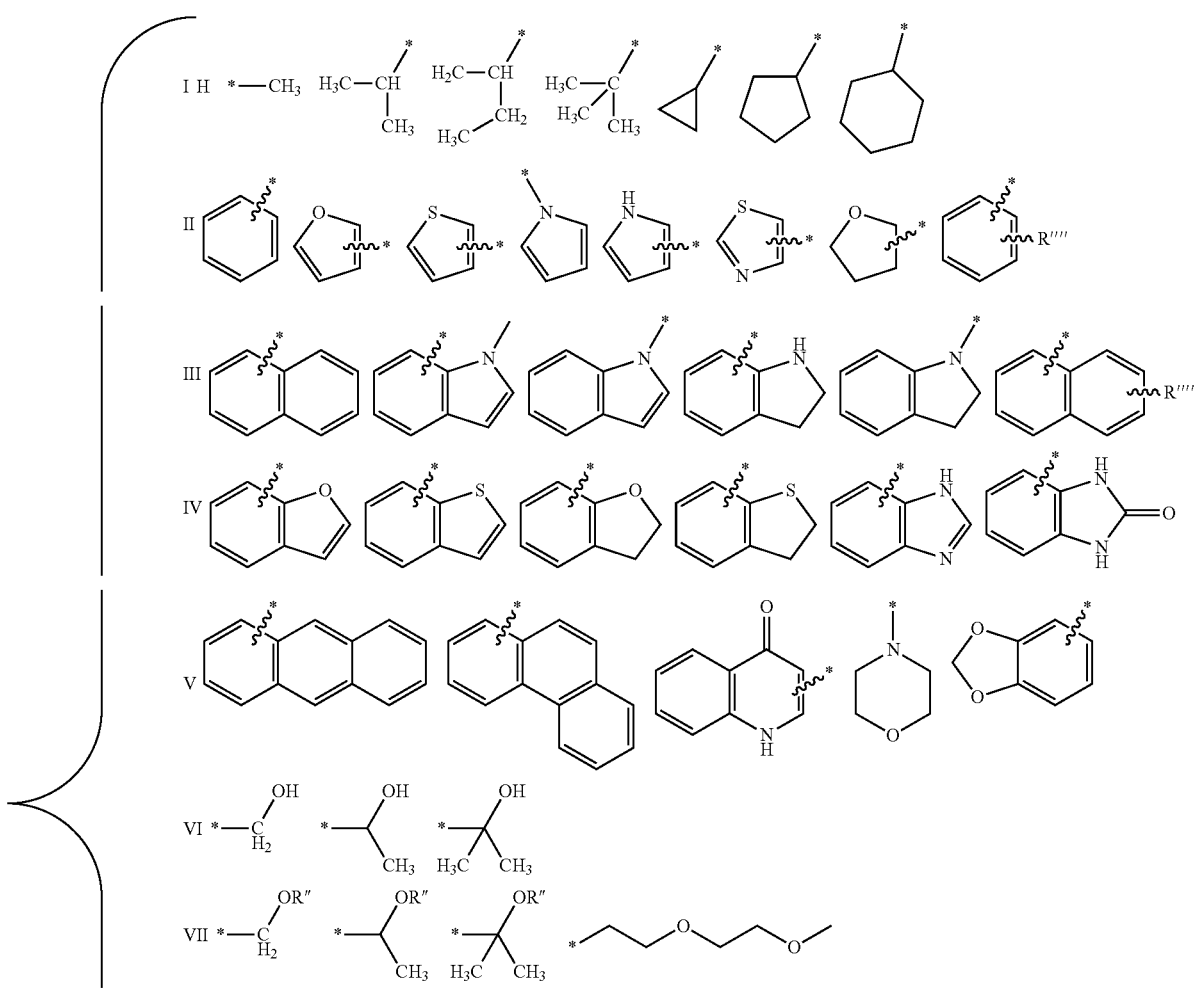

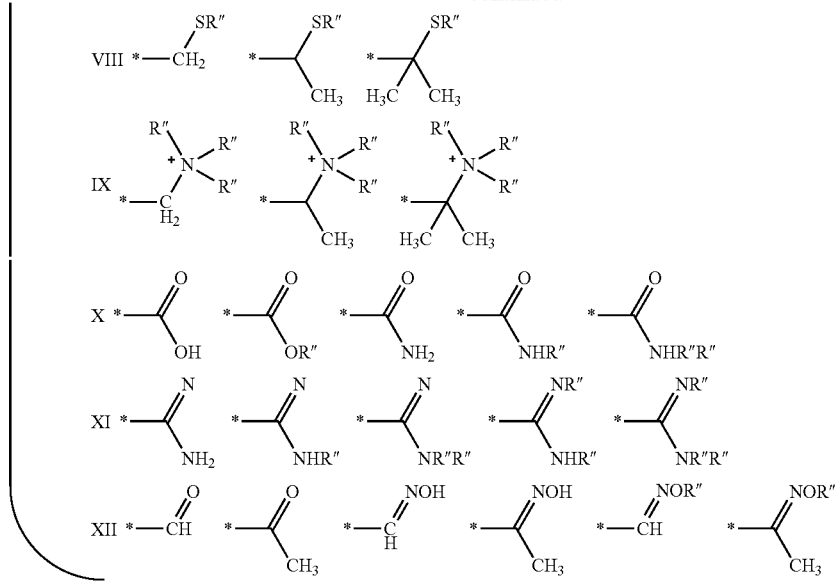

And, R", R'" and R"" are defined as follows:
wherein
R'" is selected from the group consisting of a branched or linear lower alkyl (C1-C20); halogen (F, Cl, Br, I); nitrite (CN); boronic acid (BO₂H₂); carboxylic acid (COOH); carboxylic Acid ester (COOR"); primary amide (CONH₂); Secondary amide (CONHR"); tertiary amide (CONR"R"): sulfonamide (SO₂N alkylsulfonamido (SONHR").

when
R", R'" are independently selected from a group consisting of a branched or linear lower alkyl (C1-C2)); phenyl (C₆H₅); an R"" substituted phenyl ring (R""C₆H₄); wherein R"" is defined above; a carboxylic acid (COOH); a carboxylic acid ester (COOR""); wherein R"" is a branched or linear lower alkyl (C1-C20); and cycloalkyl; wherein R"=R"=(CH₂)$_n$;
Wherein n=2-10, Further C-5 modified pyrimidine nucleotides include the following:

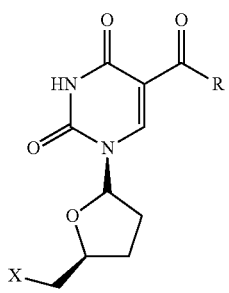

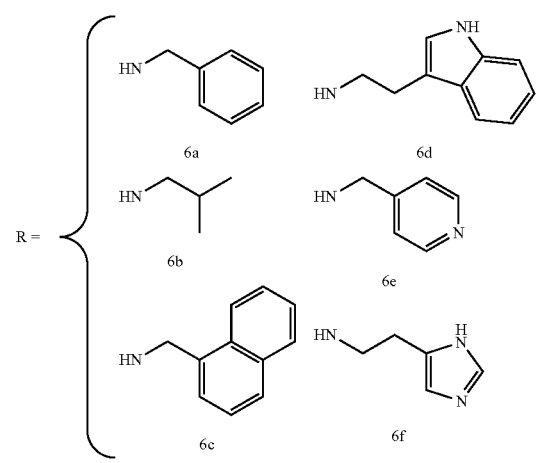

In some embodiments, the modified nucleotide confers nuclease resistance to the aptamer. A pyrimidine with a substitution at the C-5 position is an example of a modified nucleotide. Modifications can include backbone modifications, methylations, unusual base-pairing combinations such as the isobases isocytidine and isoguanidine, and the like. Modifications can also include 3' and 5' modifications, such as capping. Other modifications can include substitution of one or more of the naturally occurring nucleotides with an analog, internucleotide modifications such as, for example, those with uncharged linkages (e.g., methyl phosphonates, phosphotriesters, phosphoamidates, carbamates, etc.) and those with charged linkages (e.g., phosphorothioates, phosphorodithioates, etc.), those with intercalators (e.g., acridine, psoralen, etc.), those containing chelators (e.g., metals, radioactive metals, boron, oxidative metals, etc.), those containing alkylators, and those with modified linkages (e.g., alpha anomeric nucleic acids, etc.). Further, any of the hydroxyl groups ordinarily present on the sugar of a nucleotide may be replaced by a phosphonate group or a phosphate group; protected by standard protecting groups; or activated to prepare additional linkages to additional nucleotides or to a solid support. The 5' and 3' terminal OH groups can be phosphorylated or substituted with amines, organic capping group moieties of from about 1 to about 20 carbon atoms, polyethylene glycol (PEG) polymers in one embodiment ranging from about 10 to about 80 kDa, PEG polymers in another embodiment ranging from about 20 to about 60 kDa, or other hydrophilic or hydrophobic biological or synthetic polymers. In one embodiment, modifications are of the C-5 position of pyrimidines. These modifications can be produced through an amide linkage directly at the C-5 position or by other types of linkages.

Aptamers can also contain analogous forms of ribose or deoxyribose sugars that are generally known in the art, including 2"-0-methyl-, 2'-0-allyl, 2'-fluoro- or 2'-azido-ribose, carbocyclic sugar analogs, a-anomeric sugars, epimeric sugars such as arabinose, xyloses or lyxoses, pyranose sugars, furanose sugars, sedoheptuloses, acyclic analogs and abasic nucleoside analogs such as methyl riboside. As noted above, one or more phosphodiester linkages may be replaced by alternative linking groups. These alternative linking groups include embodiments wherein phosphate is replaced by P(0)S ("thioate"), P(S)S ("dithioate"), (0)NR$_2$ ("amidate"), P(O)R, P(0)OR', CO or CH$_2$ ("formacetal"), in which each R or R' is independently H or substituted or unsubstituted alkyl (1-20 C) optionally containing an ether (-0-) linkage, aryl, alkenyl, cycloalky, cycloalkenyl or araldyl. Not all linkages in an aptamer need be identical. Substitution of analogous forms of sugars, purines, and pyrimidines can be advantageous in designing a final product, as can alternative backbone structures like a polyamide backbone, for example.

Specific examples of C-5 modified pyrimidines that may be included or incorporated into an aptamer include, but are not limited to the structures herein. While the naming convention used for the structure assumes X is —H (i.e., DNA), they also encompass structures where X may be —OH (RNA), or other substituents described herein (e.g., —OCH$_3$; —O-allyl; —F, —OEt; —OPr, —NH$_2$; -azido or —OCH$_2$CH$_2$OCH$_3$), R' may —H; —OAc; —OBz; —OCH$_2$CH$_2$OCH$_3$ and —OSiMe$_2$tBu and R" may be —H; DMT and triphosphate (—P(O)(OH)—O—P(O)(OH)—O—P(O)(OH)$_2$), and salts thereof.

Exemplary NapdU Structure (5-[N-(1-naphthylmethyl) carboxamide]-2'-deoxyuridine):

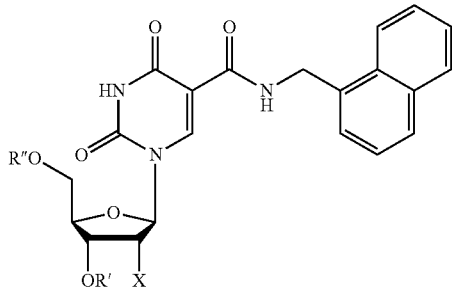

Exemplary 2NapdU structure (5-[N-(2-naphthylmethyl) carboxamide]-2'-deoxyuridine):

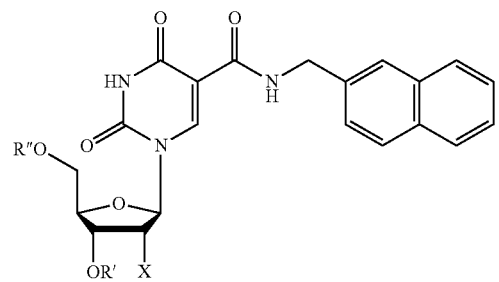

Exemplary PPdU structure (5-[N-(phenyl-3-propyl)carboxamide]-2'-deoxyuridine):

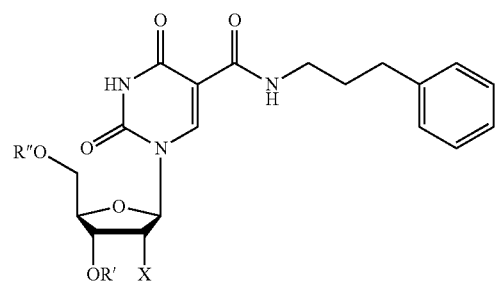

Exemplary TrpdU structure (5-[N-(3-indole-2-ethyl)carboxamide]-2'-deoxyuridine):

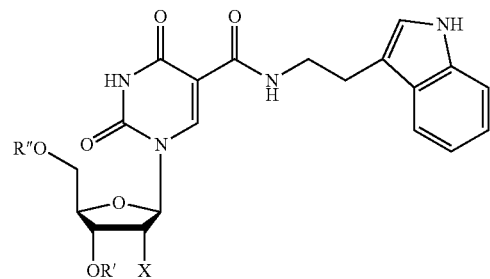

Exemplary 2NEdU structure 5-[N-(2-naphthyl-2-ethyl) carboxamide]-2'-deoxyuridine):

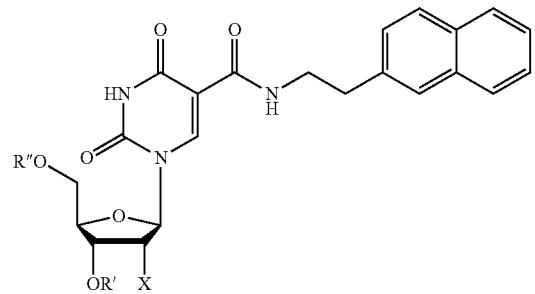

The following examples are provided to illustrate certain particular features and/or embodiments. These examples should not be construed to limit the disclosure to the particular features or embodiments described.

D. Exemplary GDF11 Aptamers

Provided herein are aptamers that bind GDF11. In some embodiments, an aptamer binds GDF11 with an affinity of less than 10 nM. In some such embodiments, the aptamer binds GDF8 with an affinity that is at least 10-fold weaker than the affinity for GDF11, when both affinities are measured under the same binding conditions. In some embodiments, the aptamer binds GDF11 with an affinity of between 0.5 nM and 10 nM and binds GDF8 with an affinity of greater than 50 nM, or greater than 100 nM, or greater than 150 nM, or greater than 200 nM, or greater than 300 nM. In some embodiments, the aptamer does not bind GDF8 under the same conditions under which the aptamer binds GDF11 with an affinity of less than 10 nM. In some embodiments, the aptamer binds GDF11 with an affinity of less than 8 nM, or less than 7 nM, or less than 6 nM, or less than 5 nM, or less than 4 nM, or less than 3 nM, or less than 2 nM, or less than 1 nM; or between 0.1 nM and 10 nM, between 0.1 nM and 8 nM, or between 0.1 nM and 5 nM.

In some embodiments, affinity determined using an assay described herein. In some embodiments, affinity is determined in the presence of a polyanionic inhibitor. Nonlimiting exemplary polyanionic inhibitors are described herein. In some embodiments, affinity is determined in the presence of Z block.

In some embodiments, an aptamer that binds GDF11 comprises the sequence:

(SEQ ID NO: 110)
5'-RW$_n$MC$_n$CPPGM$_m$MPPPA$_n$AC$_n$MC$_m$RW$_n$PPG$_n$PAS$_n$GC-3', wherein:

each P is independently, and for each occurrence, a C-5 modified pyrimidine;

R is A or G;

each W is independently, and for each occurrence, A, T, or U;

each M is independently, and for each occurrence, A or C;

S is G or C;

each n is independently, and for each occurrence, 0 or 1; and each m is independently, and for each occurrence, 0 or 1.

In some embodiments, an aptamer that binds GDF11 comprises a sequence selected from:

(SEQ ID NO: 111)
a) 5'-RW$_n$AC$_n$CPPGM$_m$MPPPA$_n$AC$_n$MC$_m$RW$_n$PPG$_n$PAS$_n$GC-3';

(SEQ ID NO: 112)
b) 5'-RW$_n$MC$_n$CPPGM$_m$MPPPA$_n$AC$_n$MC$_m$GW$_n$PPG$_n$PAS$_n$GC-3'; and (SEQ ID NO: 113)
c) 5'-RMCPPGM$_m$MPPPA$_n$AC$_n$MC$_m$RW$_n$PPPAS$_n$GC-3';

wherein R, W, P, M, S, n, and m are defined as above.

In some embodiments, if R is G, the first W is A; or if R is A, the first W is C. In some embodiments, at least 1, at least 2, at least 3, at least 4, at least 5, or at least 6 n are 0. In some embodiments, each n is 0. In some embodiments, at least 1, at least 2, at least 3 n are 1. In some embodiments, at least 1 m is 1. In some embodiments, at least 1 m is 0.

In some embodiments, a GDF11 aptamer is provided, wherein the aptamer comprises the sequence 5'-CPPGMPPP-3' (SEQ ID NO: 114), wherein each P is independently, and for each occurrence, a C-5 modified pyrimidine, and wherein M is C or A. In some embodiments, a GDF11 aptamer is provided, wherein the aptamer comprises the sequence 5'-PPPAGC-3' (SEQ ID NO: 115), wherein each P is independently, and for each occurrence, a C-5 modified pyrimidine. In some embodiments, the aptamer comprises the sequence 5'-CPPGMPPPN$_x$PPPAGC-3' (SEQ ID NO: 116), wherein each P is independently, and for each occurrence, a C-5 modified pyrimidine, wherein x is 2, 3, 4, or 5, wherein M is C or A, and wherein each N is independently, and for each occurrence, selected from A, C, G, T, and U. In some such embodiments, x is 3 or 4. In some embodiments, N$_x$ comprises the sequence 5'-AAG-3' or 5'-ACG-3' or 5'-AGG-3'.

In some embodiments, an aptamer that binds GDF11 comprises the sequence 5'-NNCPPGRPPPAMGPPPAGS-3' (SEQ ID NO: 141), wherein each P is independently, and for each occurrence, a C-5 modified pyrimidine, R is A or G; each N is independently, and for each occurrence, A, G, or C; M is A or C; and S is G or C.

In any of the embodiments described herein, each P is independently selected from the C-5 modified pyrimidines described herein. In some embodiments, each P is selected from 5-(N-1-naphthylmethylcarboxyamide)-2'-deoxyuridine (NapdU),
5-(N-1-naphthylmethylcarboxyamide)-2'-O-methyluridine,
5-(N-1-naphthylmethylcarboxyamide)-2'-fluorouridine,
5-(N-2-naphthylmethylcarboxyamide)-2'-deoxyuridine (2NapdU),
5-(N-2-naphthylmethylcarboxyamide)-2'-O-methyluridine,
5-(N-2-naphthylmethylcarboxyamide)-2'-fluorouridine,
5-(N-1-naphthylethylcarboxyamide)-2'-deoxyuridine (NEdU),
5-(N-1-naphthylethylcarboxyamide)-2'-O-methyluridine,
5-(N-1-naphthylethylcarboxyamide)-2'-fluorouridine,
5-(N-2-naphthylethylcarboxyamide)-2'-deoxyuridine (2NEdU),
5-(N-2-naphthylethylcarboxyamide)-2'-O-methyluridine,
5-(N-2-naphthylethylcarboxyamide)-2'-fluorouridine,
5-(N-3-benzofuranylethylcarboxyamide)-2'-deoxyuridine (BFdU),
5-(N-3-benzofuranylethylcarboxyamide)-2'-O-methyluridine,
5-(N-3-benzofuranylethylcarboxyamide)-2'-fluorouridine,
5-(N-3-benzothiophenylethylcarboxyamide)-2'-deoxyuridine (BTdU),
5-(N-3-benzothiophenylethylcarboxyamide)-2'-O-methyluridine, and
5-(N-3-benzothiophenylethylcarboxyamide)-2'-fluorouridine.

In some embodiments, at least 1, at least 2, at least 3, at least 4, at least 5, or at least 6 P are each independently selected from 5-(N-naphthylmethylcarboxyamide)-2'-deoxyuridine (NapdU), 5-(N-2-naphthylmethylcarboxyamide)-2'-O-methyluridine, and 5-(N-2-naphthylmethylcarboxyamide)-2'-fluorouridine.

In some embodiments, a GDF11 aptamer comprises a sequence selected from SEQ ID NOs: 12, 13, 15 to 109, and 117 to 140. In some embodiments, a GDF11 aptamer comprises a sequence selected from SEQ ID NOs: 12, 15, 26, 105 to 109, and 142 to 150.

In some embodiments, a GDF11 aptamer may include up to about 100 nucleotides, up to about 95 nucleotides, up to about 90 nucleotides, up to about 85 nucleotides, up to about 80 nucleotides, up to about 75 nucleotides, up to about 70 nucleotides, up to about 65 nucleotides, up to about 60 nucleotides, up to about 55 nucleotides, up to about 50 nucleotides, up to about 45 nucleotides, up to about 40 nucleotides, up to about 35 nucleotides, up to about 30 nucleotides, up to about 25 nucleotides, and up to about 20 nucleotides.

In another aspect this disclosure, the GDF11 aptamer may be at least about 95% identical, at least about 90% identical, at least about 85% identical, at least about 80% identical, or at least about 75% identical to any of SEQ ID NO:1 or 2. In another embodiment, the GDF11 aptamer includes a sequence from any of SEQ ID NOs:1 or 2, and fragments thereof. In a related aspect, the fragments thereof are from about 25 to 49 nucleotides in length (or from about 25, 26, 27, 28, 29, 30, 31, 32, 33, 34, 35, 36, 37, 38, 39, 40, 41, 42, 43, 44, 45, 46, 47, 48 or 49 nucleotides in length).

In another aspect this disclosure, the GDF11 aptamer may a dissociation constant ($K_d$) for GDF11 of about 10 nM or less. In another exemplary embodiment, the GDF11 aptamer has a dissociation constant ($K_d$) for the GDF11 protein of about 15 nM or less. In yet another exemplary embodiment, the GDF11 aptamer has a dissociation constant ($K_d$) for the GDF11 protein of about 20 nM or less. In yet another exemplary embodiment, the GDF11 aptamer has a dissociation constant ($K_d$) for the GDF11 protein of about 25 nM or less. In yet another exemplary embodiment, the GDF11 aptamer has a dissociation constant ($K_d$) for the GDF11 protein of about 30 nM or less. In yet another exemplary embodiment, the GDF11 aptamer has a dissociation constant ($K_d$) for the GDF11 protein of about 35 nM or less. In yet another exemplary embodiment, the GDF11 aptamer has a dissociation constant ($K_d$) for the GDF11 protein of about 40 nM or less. In yet another exemplary embodiment, the GDF11 aptamer has a dissociation constant ($K_d$) for the GDF11 protein of about 45 nM or less. In yet another exemplary embodiment, the GDF11 aptamer has a dissociation constant ($K_d$) for the GDF11 protein of about 50 nM or less. In yet another exemplary embodiment, the GDF11 aptamer has a dissociation constant ($K_d$) for the GDF11 protein in a range of about 3-10 nM (or 3, 4, 5, 6, 7, 8, 9 or 10 nM. A suitable dissociation constant can be determined with a binding assay using a multi-point titration and fitting the equation y=(max−min)(Protein)/($K_d$+Protein)+min as described herein. In other embodiments, the GDF11 aptamer is an aptamer with a $K_d$ that is less than or equal to the $K_d$ of an aptamer comprising the sequence of SEQ ID NO: 12.

In some embodiments, an aptamer comprises a detectable label.

Methods of Detecting GDF11

In some embodiments, methods of detecting GDF11 in a sample are provided, comprising contacting the sample with an aptamer described herein. In some embodiments, methods of detecting or quantifying GDF11 in the presence of GDF8 are provided, comprising contacting the sample suspected of containing both GDF11 and GDF8 with an aptamer described herein. In some embodiments, methods of distinguishing GDF11 from GDF8 in a sample are provided, comprising contacting the sample with an aptamer described herein. In some embodiments, the method comprises contacting the sample with a GDF11 aptamer described herein in the presence of a polyanionic inhibitor.

Detecting and/or quantifying GDF11 bound by the GDF11 aptamer can be accomplished using methods in the art and/or methods described herein. In some embodiments, the GDF11 aptamer comprises a detectable label. In some embodiments, the GDF11 aptamer is bound to a solid support, or comprises a member of a binding pair that may be captured on a solid support (for example, a biotinylated aptamer may be bound to a solid support comprising streptavidin).

Kits Comprising GDF11 Aptamer Compositions

The present disclosure provides kits comprising any of the GDF11 aptamers described herein. Such kits can comprise, for example, (1) at least one GDF11 aptamer; and (2) at least one pharmaceutically acceptable carrier, such as a solvent or solution. Additional kit components can optionally include, for example: (1) any of the pharmaceutically acceptable excipients identified herein, such as stabilizers, buffers, etc., (2) at least one container, vial or similar apparatus for holding and/or mixing the kit components; and (3) delivery apparatus.

EXAMPLES

Example 1: Selection and Identification of Aptamers Having GDF11 Binding Specificity This example provides the representative method for the selection and production of aptamers that bind the mature GDF11 protein.

Previous attempts to select aptamers having specificity to GDF11 have been challenging. A comparison of protein binding affinity for GDF11 and myostatin (GDF8) of several aptamers selected using the SELEX process are shown in Table 1 below.

TABLE 1

| Aptamer Identifier | Affinity $K_d$ (nM) | | $K_d$ Ratio |
| --- | --- | --- | --- |
| | GDF11 | GDF-8 | GDF11/GDF-8 |
| 1 | 1.3 | 8.9 | 0.14 |
| 12 | 0.8 | 0.8 | 0.92 |
| 19 | 1.6 | 3.3 | 0.49 |
| 47 | 343 | 54.5 | 6.29 |
| 8 | 253 | 41.2 | 6.14 |
| 9 | 78.2 | 20.7 | 3.78 |
| 4 | 0.9 | 0.5 | 1.65 |

As shown in Table 1, the aptamers selected to bind GDF11 generally also had affinity for myostatin. The ratio of binding affinity for GDF11 to myostatin for each aptamer is also shown in Table 1. The ratios vary from below one (1) (i.e., the aptamer had greater affinity for myostatin compared to GDF11), to ratios of from about 1.6 to about 6.3 (i.e., the aptamer had a greater affinity for GDF11 compared to myostatin). However, these affinities differences are not sufficient to discriminate between GDF11 and myostatin in a protein binding assay. As a result, the presence and/or levels of GDF11 and GDF8 cannot be distinguished. In light of the challenges of identifying a GDF11 aptamer that can discriminate GDF11 from myostatin, a counter-selection strategy was introduced into the SELEX process.

Aptamer Selection with Slow Off-Rate Enrichment Process

SELEX with GDF11 was performed using the SELEX methods described herein. In addition, protocol modifications involving two different types of counter-selections were applied to select GDF11 aptamers that do not bind myostatin or have a greater affinity for GDF11 than myostatin: passive counter-selection and active count-selection.

Passive counter-selection was done with the unwanted target (myostatin) in untagged form by adding it to PCB (protein competitor buffer containing prothrombin, casein and albumin) during selection, removing sequences that lack preference for GDF11 over myostatin. The ratio of myostatin to GDF11 was 1:1 in the first round (100 pmol each), 2:1 in the second round (20 pmol myostatin and 10 pmol GDF11), and increased in subsequent rounds of SELEX as the GDF11 target concentration was reduced (20 pmol myostatin and 0.3 pmol GDF11 or about 67:1).

Active counter-selection was done with biotinylated myostatin immobilized on streptavadin (SA) beads. Prior to each round of SELEX, the library was incubated with the counter-selection beads for 10 min with shaking at 37° C. Then the supernatant was recovered and moved into selection with GDF11, leaving sequences that bind myostatin behind on the beads. The first round used 100 pmol myostatin to counter-select 1000 pmol library, each subsequent round used 20 pmol myostatin to counter-select approximately 20-50 pmol library.

Preparation of Candidate Mixture

A candidate mixture of partially randomized ssDNA oligonucleotides was prepared by polymerase extension of a DNA primer annealed to a biotinylated ssDNA template (shown in Table 2 below). The candidate mixture contained a 40 nucleotide randomized cassette containing dATP, dGTP, dCTP and 5-(N-naphthylmethylcarboxyamide)-2'-deoxyuridine triphosphate (NapdUTP).

TABLE 2

Sequences of Template and Primers

| Oligo Designation | Sequence (5' → 3') | SEQ ID NO: |
|---|---|---|
| Template 1 | AB'AB'TTTTTTTTGTCTCTTGTTCTTGTCT TGTG-(N)$_{40}$-CAGGGCATCAGAGCGTTTCG | 1 |
| Primer 1 | ATATATATCGAAACGCTCTGATGCCCTG | 2 |
| Primer 2 | AB'AB'TTTTTTTTGTCTCTTGTTCTTG TCTTGTG | 3 |

B' = biotin

Five milliliters of a 50% slurry of Streptavidin Plus UltraLink Resin (PIERCE) was washed once with 2.5 mL of 20 mM NaOH, twice with 2.5 mL of SB18T0.05 (40 mM HEPES (4-(2-Hydroxyethyl)piperazine-1-ethanesulfonic acid) buffer adjusted to pH 7.5 with NaOH, 102 mM NaCl, 5 mM KCl, 5 mM MgCl2 and 0.05% TWEEN 20) and twice with 2.5 mL of 16 mM NaCl. Eighty nanomoles of template 1 (SEQ ID NO: 1) possessing two biotin residues (designated as B' in the sequence) and 40 randomized positions (designated as $N_{40}$ in the sequence) were added to the washed UltraLink SA beads and rotated at 37° C. for 2.5 hours. The beads were then washed three times with 16 mM NaCl. Between each wash, the beads were recovered by centrifugation. The beads, now containing the captured template, were suspended in 3.75 mL of extension reaction buffer [containing 80 nmol of primer (SEQ ID NO: 2), 1×SQ20 buffer (120 mM Tris-HCl, pH7.8, 10 mM KCl, 7 mM MgSO$_4$, 6 mM (NH$_4$)$_2$SO$_4$, 0.001% BSA and 0.1% Triton X-100), 470 units of KOD XL DNA Polymerase (EMD MILLIPORE), and 1 mM each of dATP, dCTP, dGTP and NapdUTP. The beads were allowed to incubate with rotation at 68° C. for 2 hours. The beads were then washed once with SB18T0.01 (SB18 as above, but with 0.01% TWEEN-20) and twice with 16 mM NaCl. The aptamer library was eluted from the beads with 2.5 mL of 40 mM NaOH. The eluted library and immediately neutralized with 50 μL of neutralizer (700 mM HCl, 180 mM HEPES, 0.45% TWEEN-20). Elution was repeated twice more, and the eluates were pooled. The library was concentrated with an AMICON Ultracel YM-10 filter to approximately 0.4 mL and the concentration of library determined by ultraviolet absorbance spectroscopy.

Biotin Labeling of Human GDF11

Untagged recombinant human GDF11-Protein purified in homodimeric form after over-expression in E. coli (Peprotech, catalog number 120-11) was biotinylated by covalent coupling of NHS-PEO4-biotin (PIERCE, EZ-Link NHS-PEG4-Biotin) to residues containing primary amines. Protein (1600 pmol in 80 μL) was mixed with a 4-fold molar excess of NHS-PEG4-biotin and the reaction was allowed to incubate at 20° C. for 1 hour. After the reaction was completed, unreacted NHS-PEG4-biotin was removed using a Zeba™ spin desalting column (PIERCE) where the buffer had been exchanged to SB18T0.05.

Biotin Labeling of Human Myostatin

Untagged recombinant human myostatin-Protein purified in homodimeric form after over-expression in E. coli (Peprotech, catalog number 120-00) was biotinylated as described above.

Immobilization of Myostatin

MYONE-SA paramagnetic beads (MYONE SA, INVITROGEN, or hereinafter referred to as SA beads) were prepared by washing the beads once with 14 mL of 20 mM NaOH and twice with 14 mL of SB18T0.05. Finally, the SA beads were suspended at 10 mg/mL in SB18T0.05 and stored at 4° C. until use. Biotin labeled myostatin-protein (500 pmol) was immobilized on for all rounds of SELEX. This was accomplished by mixing SA beads (5 mgs) with biotin labeled myostatin (500 pmol) for 30 min with shaking, followed by washing three times with SB18T0.05. The SA-myostatin beads were resuspended in 0.5 mL SB18T0.05 (10 mgs/mL beads with 1 μM myostatin attached) and stored at 4° C. until use.

Aptamer Selection with Slow Off-Rate Enrichment Process

A total of 11 rounds of the SELEX process were completed with selection for affinity and slow off-rate. Prior to each round a counter selection was performed to reduce background and to reduce the likelihood of obtaining aptamers with nonspecific binding to protein. In addition, separate types of counter-selections were applied to force selection of GDF11 aptamers that do not bind the closely related, 90% identical protein myostatin. Counter selections were performed as follows.

For round 1, 100 μL of the DNA candidate mixture containing approximately 1 nmole of DNA in SB18T0.05 was heated at 95° C. for 5 minutes and then cooled to 70° C. for 5 minutes, then to 48° C. for 5 minutes and then transferred to a 37° C. block for 5 minutes. The sample was then combined with 10 μL of protein competitor mixture and 1 mg (100 μL) of counter-selection beads and incubated at 37° C. for 10 minutes with mixing. Beads were removed by magnetic separation. The protein competitor mixture and the counter-selection beads were composed as follows. Standard SELEX used 10 μL of standard protein competitor mixture (0.1% HSA, 10 μM casein, and 10 μM prothrombin in SB18T0.05), and 1 mg (100 μL) of SA beads. SELEX with passive counter-selection used 10 μL of a modified protein competitor mixture (0.1% HSA, 10 μM casein, 10 μM prothrombin, and 10 μM unlabeled myostatin in SB18T0.05) and 1 mg (100 μL) of SA beads. SELEX with active counter-selection used 10 μL of standard protein competitor mixture (0.1% HSA, 10 μM casein, and 10 μM prothrombin in SB18T0.05), and 1 mg (1004) of SA-myostatin beads (SA beads with 1 μM myostatin attached).

For Rounds 2-11, a 68 μL aliquot of the DNA candidate mixture obtained from the previous round (68% of eDNA obtained from previous round) was mixed with 13 µL of 5×SB18T0.05. The sample was heated to 95° C. for 3 minutes and cooled to 37° C. at a rate of 0.1° C./second. The sample was then combined with 9 µL of protein competitor mixture (0.1% HSA, 10 µM casein, and 10 µM prothrombin in SB18T0.05), and 0.1 mg (10 µL) of SA beads and incubated at 37° C. for 10 minutes with mixing (standard SELEX). As in round 1, the protein competitor mixture was supplemented with 10 µM unlabeled myostatin (SELEX with passive counter-selection), and the SA-myostatin beads (SA beads with 1 µM myostatin attached) were used instead of SA beads (SELEX with active counter-selection). Beads were removed by magnetic separation.

Following the first counter selection the target protein was pre-immobilized on SA beads for the Round 1 selection process. To accomplish this, 0.5 mg of SA beads was mixed with 50 pmoles of biotin labeled target protein (GDF11 homodimer) and incubated with shaking for 30 minutes at 37° C. Unbound target was removed by washing the beads twice with SB18T0.05. The counter-selected-DNA candidate mixture (100 µL) was added to the beads and incubated at 37° C. for 60 minutes with mixing. No slow off-rate enrichment process was employed in the first round and beads were simply washed 5 times for 2 min each with 100 µL SB18T0.05. Following the washes, the bound aptamer was eluted from the beads by adding 45 µL of 8 mM NaOH, and incubating at 37° C. for 5 minutes with mixing. The aptamer-containing-eluate (404) was transferred to a new tube after magnetic separation of the beads. Elution was repeated once more with 45¼ of 8 mM NaOH, and incubating at 37° C. for 5 minutes with mixing. The eluates were combined (80 uL) and the solution neutralized by addition of 20 µL of 32 mM HCl and 2 µL Tris-HCl pH 7.5.

For Rounds 2-11, selections were performed with the DNA candidate mixture and target protein as described below while, in parallel, an identical selection was performed with the DNA candidate mixture, but without the target protein. Comparison of the Ct values obtained from PCR for the sample with target protein (signal S) and sample without target protein (background B) were used as a guide to reduce the target concentration in the next round. If the delta Ct value was greater than 4, but less than 8, the target protein was reduced three fold in the next round. If the delta Ct value was greater than 8, the target was reduced 10-fold in the next round.

Following these scheme, reductions in GDF11 concentrations after the rounds of standard SELEX were 3-fold (Rounds 5-6), 10-fold (Rounds 7-8), 30-fold (Rounds 9-10), and 100-fold (Round 11). For selections with passive counter-selection, reductions in target concentration were 3-fold (Rounds 5-6), 10-fold (Rounds 7-10), and 30-fold (Round 11). For selections with active counter-selection, reductions in target concentration were 3-fold (Rounds 5-6), 10-fold (Round 7), 30-fold (Round 8-10), and 100-fold (Round 11). The "RX", where X is a number, represents the round number for SELEX (e.g., R3 indicates Round 3 for SELEX).

| Target | Counter-selection | R3 | R4 | R5 | R6 | R7 | R8 | R9 | R10 | R11 |
|---|---|---|---|---|---|---|---|---|---|---|
| GDF-11 | standard | 1 | 1 | 3 | 3 | 10 | 10 | 30 | 30 | 100 |
| GDF-11 | passive | 1 | 1 | 3 | 3 | 10 | 10 | 10 | 10 | 30 |
| GDF-11 | active | 1 | 1 | 3 | 3 | 10 | 30 | 30 | 30 | 100 |

Reduction of Target Concentration after Round of SELEX (based on delta Ct)

For Round 2, labeled target protein (5 pmoles of GDF11 homodimer in 10 µL) was mixed with 40 µL of counter selected DNA candidate mixture and incubated at 37° C. for 15 minutes. A slow off-rate enrichment process was begun by adding 50 µL of 10 mM dextran sulfate followed by the immediate addition of 0.1 mg of SA beads. This was allowed to incubate for 15 minutes at 37° C. with mixing. Beads were then washed 5 times with 100 µL of SB18T0.05. The aptamer strand was eluted from the beads by adding 105 µL of sodium perchlorate elution buffer (1.8 M NaClO4, 40 mM PIPES pH 6.8, 1 mM EDTA, 0.05% Triton X-100), and incubating at 37° C. for 10 minutes with mixing. Beads were removed by magnetic separation and 100 µL of aptamer eluate was transferred to a new tube containing primer capture beads (25 µL of 2.5 mg/mL SA beads with 12.5 pmol primer 2 (SEQ ID NO: 2) attached) and allowed to incubate for 30 minutes at 50° C. with mixing. Beads were then washed three times with 100 µL of SB18T0.05. The aptamer strand was eluted from the beads by adding 85 µL of 40 mM NaOH, and the eluate (80 µL) was neutralized with 20 µL of 160 mM HCl and 2 µL of 500 mM Tris-HCl pH 7.5.

Rounds 3 through 11 selections were performed as described for Round 2 except dextran sulfate was added 15 minutes (rounds 3-4), 30 minutes (round 5), 45 minutes (round 6), 60 minutes (round 7), 75 min (round 8), or 90 minutes (rounds 9-11) prior to the addition of beads. Partitioning was done with 0.1 mg Neutravidin Coated Sera-Mag SpeedBeads (Fisher Scientific, Catalog No. 09-981-155, or hereinafter referred to as NA beads, rounds 3, 5, 7, 9, 11) or with 0.1 mg of SA beads (rounds 4, 6, 8, 10).

Pools obtained after 11 rounds of SELEX showed good activity to warrant Ion Torrent ePCR and sequencing (Table 3). From each pool, 384 sequences were obtained for comparative sequence analysis followed by binding assays of the lead candidates.

TABLE 3

Affinity data for GDF11 aptamer pools obtained with standard SELEX, and with passive or active counter-selection with myostatin.

| | | Counter-selection | | NapdU | | TrpdU | |
|---|---|---|---|---|---|---|---|
| Target Protein | SELEX method | Passive | Active (beads) | Pool | $K_d$ (nM) | Pool | $K_d$ (nM) |
| GDF11 | Standard | PCB | SA | 12058 | 0.66 | 12076 | 0.29 |
| GDF11 | Modified | PCB + myostatin | SA | 12060 | 0.63 | 12078 | 0.37 |
| GDF11 | Modified | PCB | SA/ myostatin | 12061 | 0.54 | 12080 | 0.58 |

Aptamer Amplification and Purification

Selected aptamer DNA from each round was amplified and quantified by QPCR. 48 µL DNA was added to 12 µL QPCR Mix (10×KOD DNA Polymerase Buffer; Novagen #71157, diluted to 5×, 25 mM MgCl₂, 10 µM forward PCR primer (Primer 1, SEQ ID NO:2), 10 µM biotinylated reverse PCR primer (Primer 2, SEQ ID NO:3), 5×SYBR Green I, 0.075 U/µL KOD XL DNA Polymerase, and 1 mM each dATP, dCTP, dGTP, and dTTP) and thermal cycled in A BIO-RAD MyIQ QPCR instrument with the following protocol: 1 cycle of 96° C. for 15 seconds, 55° C. for 10 seconds, and 68° C. for 30 minutes; followed by 30 cycles of 96° C. for 15 seconds, 68° C. for 1 minute. Quantification was done with the instrument software and the number of copies of DNA selected, with and without target protein, was compared to determine signal/background ratios.

Following amplification, the PCR product was captured on SA beads via the biotinylated antisense strand. 1.25 mL SA beads (10 mg/mL) were washed once with 14 mL 20 mM NaOH, twice with 14 mL SB18T0.05, resuspended in 1.25 mL 3 M NaCl+0.05% TWEEN, and stored at 4° C. 25 µL SA beads (10 mg/mL in 3 M NaCl) were added to 50 µL double-stranded QPCR products and incubated at 25° C. for 5 minutes with mixing. The "sense" strand was eluted from the beads by adding 100 µL of 40 mM NaOH, and incubating at 37° C. for 5 minutes with mixing. The eluted strand was discarded and the beads were washed twice with SB18T and once with 16 mM NaCl.

Aptamer sense strand containing NapdUTP was prepared by primer extension from the immobilized antisense strand. The beads were suspended in 404 primer extension reaction mixture (1× Primer Extension Buffer (120 mM Tris-HCl pH 7.8, 10 mM KCl, 7 mM $MgSO_4$, 6 mM $(NH_4)_2SO_4$, 0.1% TRITON X-100 and 0.001% bovine serum albumin), 2.5 µM forward primer (Primer 1, SEQ ID NO: 2), 0.5 mM each dATP, dCTP, dGTP, and NapdUTP, and 0.015 U/µL KOD XL DNA Polymerase) and incubated at 68° C. for 60 minutes with mixing. The beads were washed 3 times with SB18T0.05, and the aptamer strand was eluted from the beads by adding 45 µL of 40 mM NaOH, and incubating at 37° C. for 5 minutes with mixing. 40 µL aptamer eluate was transferred to a new tube after magnetic separation, and elution was repeated once more with 454 of 40 mM NaOH, and incubating at 37° C. for 5 minutes with mixing. The eluates were combined (80 uL) and the solution neutralized with 20 µL of 160 mM HCl and buffered with 10 µL of 0.1 M HEPES, pH 7.5.

Selection Stringency and Feedback

The relative target protein concentration of the selection step was lowered each round in response to the QPCR signal (Δ Ct) following the rule below:

If Δ Ct<4, $[P]_{(i+1)}=[P]_{(i)}$
If 4≤Δ Ct<8, $[P]_{(i+1)}=[P]_{(i)}/3.2$
If Δ Ct≥8, $[P]_{(i+1)}=[P]_{(i)}/10$

Where [P]=protein concentration and i=current round number.

After each selection round, the convergence state of the enriched DNA mixture was determined. 10 µL double-stranded QPCR product was diluted to 200 µL with 4 mM $MgCl_2$ containing 1×SYBR Green I. Samples were analyzed for convergence using a Cot analysis which measures the hybridization time for complex mixtures of double stranded oligonucleotides. Samples were thermal cycled with the following protocol: 3 cycles of 98° C. for 1 minute, 85° C. for 1 minute; 2 cycles of 98° C. for 1 minute, then 85° C. for 30 minutes. During the 30 minutes at 85° C., fluorescent images were measured at 5-second intervals. The fluorescence intensity was plotted as a function of the logarithm of time, and an increased rate of hybridization with each SELEX round was observed, indicating sequence convergence.

Enriched Pool Sequencing & Aptamer Identification

After 11 rounds of SELEX, the converged pool was sequenced. Sequence preparation was performed as follows. The pool was amplified by PCR using SELEX library-specific primers containing a unique barcode/index sequence (unique sequence identifier for each pool). Individual PCR products were quantified using a Quant-iT™ PicoGreen® dsDNA Reagent (LIFE TECHNOLOGIES) assay, combined at equimolar concentrations, and concentrated/buffer exchanged using an AMICON Ultra-0.5 Centrifugal Filter Device (MILLIPORE). The mixture was then purified by SDS-polyacrylamide gel electrophoresis (PAGE), and the eluate concentrated using an Amicon Ultra-0.5 Centrifugal Filter Device and visualized by PAGE to confirm the size, purity and yield of the final mix. The sample was submitted to SeqWright Genomic Services (GE HEALTHCARE, Houston, Tex.) for Ion Torrent PGM sequencing. From a sequence pool containing over 40,000 sequences, 384 were randomly selected and analyzed for convergence using custom software that determines sequence counts/copy number and identifies common convergence patterns using a local-alignment algorithm. Sequences with the greatest representation/copy number in the pool and at least one sequence from every convergence pattern were chosen for further characterization. Of note, those sequence reads from the SELEX aptamer pools that had a sequence quality score that was "low" (i.e., a Phred quality score of 20 or below) were removed from the sequence analysis and motif identification.

Aptamer Identification by Functional Assay and by Subtractive Sequence Analysis

Convergence pattern 1 was originally identified from sequences 12060-28_3 (SEQ ID NO:12) and 12060-16_3 (SEQ ID NO:13) via comparative binding assays with GDF11 and myostatin (see Example 2). The letter "P" in the sequences indicate a NapdU.

```
Aptamer ID 12060-28_3:
                                          (SEQ ID NO: 12)
5'-ccctgCGCCPPCGGACPPGCPPPAAGPPPAGCCGCPPGCPCACA
Pcacaa-3'

Aptamer ID 12060-16_3:
                                          (SEQ ID NO: 13)
5'-ccctgPGAGACPPGAPPPACGPPPAGCPGCPAACAPGGGGAACC
Acacaa-3'
```

In parallel, Convergence pattern 1 was identified in silico via comparative and subtractive sequence analysis of sequences from pools obtained with different SELEX variations. These included 768 sequences from pool 12058 (GDF11 standard SELEX), 384 sequences from pool 12060 (GDF11 SELEX with passive counter-selection), 384 sequences from pool 12061 (GDF11 SELEX with active counter-selection), and 384 sequences from pool 12059 (myostatin standard SELEX). Analysis and alignments of all sequences in these combined pools was used to de-prioritize sequences with common patterns present in all pools, indicative of non-discriminating binding of GDF11 and myostatin (see Table 4). Convergence pattern 1 was highly enriched in pool 12060 from GDF11 SELEX with passive counter-selection (15%) and had lower abundance in pool 12058 from GDF11 standard SELEX (3%) and was absent in pool 12059 from myostatin standard SELEX, indicative of GDF11 specificity.

TABLE 4

| Pattern | Pool 12058 (GDF11, standard SELEX) | | Pool 12060 (GDF11, passive counter-selection) | | Pool 12061 (GDF11, active counter-selection) | | Pool 12059 (Myostatin, standard SELEX) | |
|---|---|---|---|---|---|---|---|---|
| | # seq | % seq | # seq | % seq | # seq | % seq | # seq | % seq |
| A | 195 | 25.4 | 18 | 4.7 | 29 | 7.6 | 15 | 3.9 |
| B | 137 | 17.8 | 17 | 4.4 | 82 | 21.4 | 54 | 14.1 |
| C | 57 | 7.4 | 14 | 3.6 | 3 | 0.8 | 11 | 2.9 |
| D | 49 | 6.4 | 14 | 3.6 | 5 | 1.3 | 0 | 0.0 |
| Pattern 1 | 24 | 3.1 | 57 | 14.8 | 0 | 0.0 | 0 | 0.0 |
| E | 21 | 2.7 | 0 | 0.0 | 1 | 0.3 | 1 | 0.3 |
| F | 15 | 2.0 | 0 | 0.0 | 0 | 0.0 | 6 | 1.6 |
| G | 1 | 0.1 | 0 | 0.0 | 6 | 1.6 | 4 | 1.0 |

Example 2: Sandwich SELEX for Aptamers the Bind GDF11

A sandwich SELEX assay was used to identify additional GDF11-specific aptamers, using a 2NEdU-containing aptamer that binds GDF11. Sandwich SELEX is described in WO 2015/048084. Briefly, SELEX is performed using a target-aptamer complex (i.e., GDF11 complexed with the 2NEdU-containing aptamer). It was found that some of the aptamers identified in the NapdU pool screened using sandwich SELEX are similar to aptamer 12060-28. Those clones are discussed further below.

Example 3: Equilibrium Binding Constant ($K_d$) for Aptamers to GDF11 Protein Versus Myostatin This example provides the protein binding affinities ($K_d$) for aptamer-GDF11 and aptamer-Myostatin protein, and the identification of aptamers that preferentially bind GDF11 over myostatin.

Several aptamer clones selected via the counter-selection SELEX method and via the sandwich SELEX method described herein were further characterized and selected for preferential binding to GDF11 over myostatin (see Table 5). Binding assays were done in the absence and in the presence of 1 µM Z-block (random oligonucleotide sequence) as a nonspecific competitor. An aptamer having BndU as the C-5 modified pyrimidine (BndU GDF11 aptamer), which was previously selected via SELEX without counter-selection steps and was used as a control for binding to both GDF11 and myostatin. Previous binding experiments with the BndU GDF11 aptamer showed that it is generally non-discriminatory for GDF11 and myostatin.

TABLE 5

Aptamer Binding Affinity Comparison: GDF11 and Myostatin

| Aptamer ID | Counter-selection SELEX Method | Mod. base | GDF11 $K_d$ (nM) | Myostatin $K_d$ (nM) | $K_d$ ratio |
|---|---|---|---|---|---|
| BndU GDF11 Aptamer | Standard | BndU | 0.05 | 0.11 | 2.29 |
| 12058-6 | Standard | NapdU | 0.09 | 0.12 | 1.32 |
| 12060-15 | Passive | NapdU | 0.20 | 0.85 | 4.22 |
| 12060-41 | (myostatin | NapdU | 0.37 | 1.81 | 4.96 |
| 12060-105 | in buffer) | NapdU | 0.19 | 0.32 | 1.74 |
| 12060-28 | | NapdU | 4.17 | >320 | >100 |
| 12060-16 | Active | NapdU | 6.52 | >320 | >50 |
| 12061-46 | (myostatin | NapdU | 0.22 | 0.20 | 0.88 |
| 12061-5 | on beads) | NapdU | 0.43 | 0.30 | 0.70 |

TABLE 5-continued

Aptamer Binding Affinity Comparison: GDF11 and Myostatin

| Aptamer ID | Counter-selection SELEX Method | Mod. base | GDF11 $K_d$ (nM) | Myostatin $K_d$ (nM) | $K_d$ ratio |
|---|---|---|---|---|---|
| 12061-12 | | NapdU | 0.14 | 0.11 | 0.81 |
| 12076-80 | Standard | TrpdU | 0.90 | 0.77 | 0.85 |
| 12076-15 | | TrpdU | 0.26 | 0.36 | 1.36 |
| 12076-349 | | TrpdU | 0.78 | 1.22 | 1.57 |
| 12078-15 | Passive | TrpdU | 0.18 | 0.62 | 3.54 |
| 12078-44 | | TrpdU | 0.50 | 0.24 | 0.49 |
| 12080-1 | Active | TrpdU | 0.32 | 0.55 | 1.71 |
| 16139-122 | Sandwich | NapdU | 2.23 | >320 | >100 |
| 16139-12 | SELEX | NapdU | 1.7 | >320 | >100 |
| 16139-178 | | NapdU | 1.08 | >320 | >100 |
| 16139-198 | | NapdU | 0.62 | >320 | >100 |
| 16139-19 | | NapdU | 1.7 | >320 | >100 |
| 16139-30 | | NapdU | 0.92 | >320 | >100 |
| 16139-37 | | NapdU | 1.21 | >320 | >100 |
| 16139-3 | | NapdU | 1.58 | >320 | >100 |

Aptamer pool 12060 (NapdU aptamers), which had been obtained by SELEX with passive counter-selection, contained several nucleotide sequences with affinity, and a varying degree of selectivity, for GDF11 (see $K_d$ ratio where a larger number indicates greater specificity for GDF11 over myostatin). In particular, aptamer clones 12060-16_3 (NapdU) showed about a 50-fold differential $K_d$ for GDF11 over myostatin (i.e., $K_d$ of 6.52 nM vs. >320 nM) when tested in the presence of 1 µM Z-block, and 12060-28_3 (NapdU), which made up 9% of the 12060 aptamer pool of nucleotide sequences showed about a 100-fold differential $K_d$ for GDF11 over myostatin (i.e., $K_d$ of 1.74 nM vs. >320 nM) when tested in the presence of 1 µM Z-block (see FIG. 1). Aptamer pool 16139 (NapdU), which was obtained by sandwich SELEX, also contained several nucleotide sequences with high affinity and specificity for GDF11.

Figure 2:
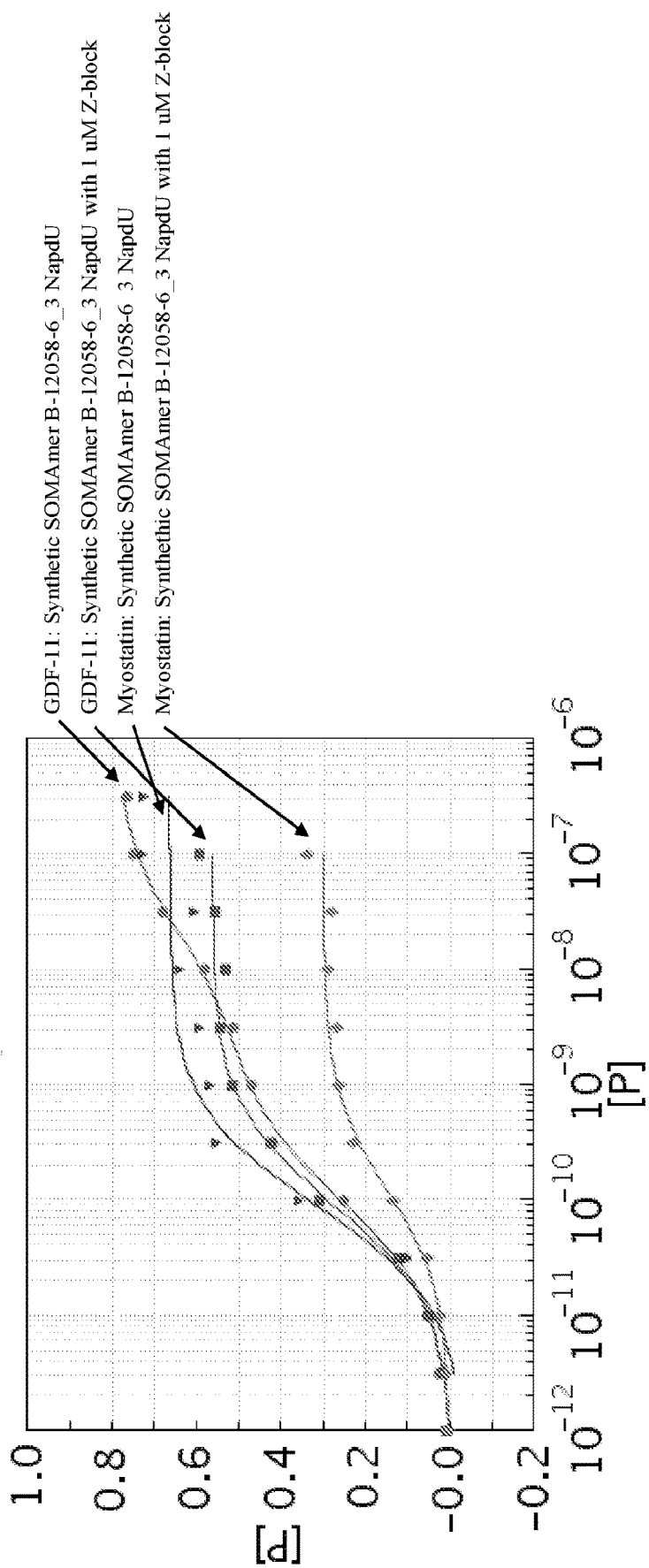
FIG. 2 shows a comparison of the binding affinities of aptamer 12058-6_3 for human GDF11 protein and human myostatin (GDF8) protein in the presence or absence of a polyanionic inhibitor (Z-block). The x-axis shows the concentrations for the respective proteins and the y-axis shows the percent of the aptamer clone bound to the protein (1.0 is 100%).

The other aptamer clones of Table 5 showed affinity for GDF11 with a range of affinity for myostatin. For example, aptamer pool 12058 (NapdU) from standard SELEX was dominated by sequence 12058-6 (17%). This aptamer clone had a $K_d$ of 0.09 nM for GDF11, but also had a $K_d$ of 0.12 nM for myostatin (FIG. 2).

Example 4: Post-SELEX Truncation and Analysis of GDF11 Aptamer 12060-28

This example provides post-SELEX the GDF11 binding affinities for truncated sequences of the 12060-28_3 aptamer and the identification of a core minimal sequence length that is capable of binding to GDF11.

Figure 3:
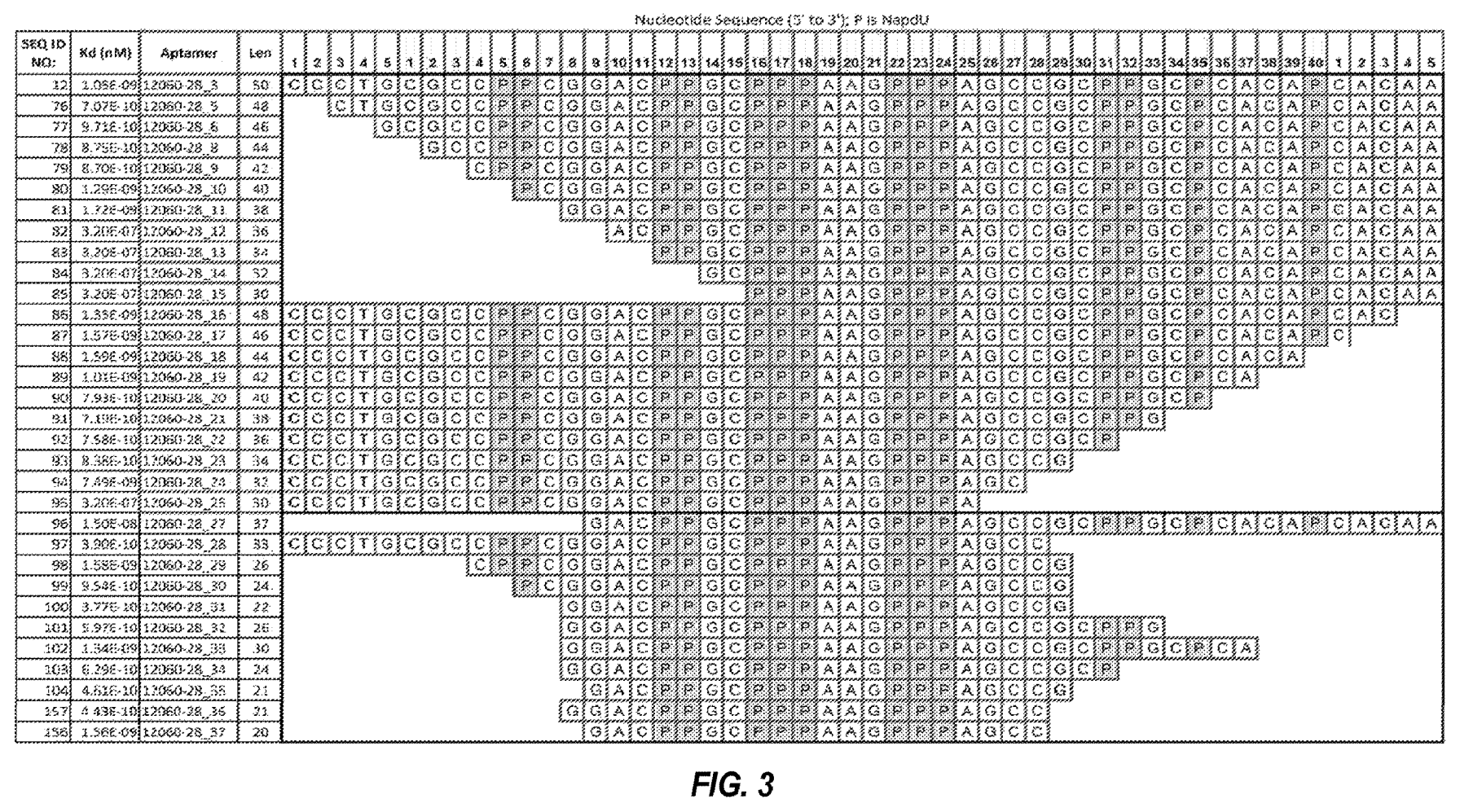

Aptamer 12060-28 (NapdU) truncations indicated that the 20-mer sequence 5'-GACPPGCPPPAAGPPPAGCC-3' (Aptamer 12060-28_37; SEQ ID NO: 156) was capable of binding GDF11. However, the activity of the 21-mer sequence 5'-GGACPPGCPPPAAGPPPAGCC-3' (Aptamer clone 12060-28_36; SEQ ID NO: 157) showed relatively better binding to GDF11 ($K_d$ of 4.43E-10) (see FIG. 3). This is consistent with the conserved motif CPPGCPPPANGPPPAGC (SEQ ID NO:105) found in a family of active clones related to 12060-28, i.e. only the NapdU residues within positions 12-24 of the 40-mer central region (motif sequence) appear to be needed for binding.

Example 5: Specific GDF11 Aptamer Sequences

This example provides a sequence alignment of a lead GDF11 selective aptamer binder (12060-28_3) with other aptamer sequences that were selected via the SELEX process. This resulted in the identification of the motif sequence in multiple sequences in the pool of sequences selected via SELEX. Affinity data is further provided for select sequences. See Table 6 for the alignment of sequences (50-mers) and binding affinity. Table 7 provides additional sequences from the aptamer pools 12060 and 12058 and their alignment. Sequences in Table 7 are shown with five (5) nucleotides removed on each of the 5' and 3' ends of the sequence (40-mers). Both Tables 6 and 7 provide the basis for a "core sequence" motif shared among the sequences. This sequence may be GACPPGAPPPACGPPPAGC (SEQ ID NO: 106); GACPPGAPPPAAGPPPAGC (SEQ ID NO: 107); GACPPGCPPPAAGPPPAGC (SEQ ID NO: 108); GACPPGCPPPACGPPPAGC (SEQ ID NO: 109); GCCPPGAPPPACGPPPAGC (SEQ ID NO: 142); CACPPGAPPPACGPPPAGG (SEQ ID NO: 143); GACPPGGPPPACGPPPAGC (SEQ ID NO: 144); GCCPPGCPPPACGPPPAGC (SEQ ID NO: 145); GCAPPGAPPPACGPPPAGC (SEQ ID NO: 146); GGCPPGCPPPACGPPPAGA (SEQ ID NO: 147); CGCPPGAPPPAAGPPPAGG (SEQ ID NO: 148); AACPPGAPPPAAGPPPAGG (SEQ ID NO: 149); or GACPPGAPPPAGGPPPAGC (SEQ ID NO: 150); where in each instance P is a NapdU. In some embodiments, the conserved motif is NNCPPGRPPPAMGPPPAGS (SEQ ID NO: 141), where in each instance P is a NapdU, R is A or G; each N is independently, and for each occurrence, A, G, or C; M is A or C; and S is G or C. It was found that sequence 12060-209_3 in Table 6, which contains a cytosine in place of one of a conserved NapdU in 12060-28, does not bind GDF11.

TABLE 6

Sequence Alignment and affinity for GDF-11 specific aptamer 12060-28 (Napd U identified by "P" in the sequences), and related clones. Affinity was determined in filter binding assays in the presence of 0.1 µM Z-block. Sequences are shown full-length (50-mers). The "x" of the motif sequence may be an A or C nucleotide.

| Aptamer ID | Nucleotide Sequence (5' to 3') (P is a NapdU) | SEQ ID NO: | GDF11 (Kd) | Myostatin (Kd) |
| --- | --- | --- | --- | --- |
| 12060-28_3 | ccctgCGCCPPCGGACPPGCPPPAAGPPPAGCCGCPPGCPCACAPcacaa | 12 | 1.7 nM | >320 nM |
| 12060-209_3 | ccctgCGCCPPCGGACPPGCPPCAAGPPPAGCCGCPPGCPCACAPcacaa | 14 | >320 nM | >320 nM |
| 12060-300_3 | ccctgCGCCPPCGGACPPGCPPPAAGPPPAGCCGCPPGCPCACAAcacaa | 15 | 0.99 nM | >320 nM |
| 12060-32_3 | ccctgPGCCPPCGGACPPGCPPPAAGPPPAGCCGCPPGCPCACAPcacaa | 16 | 1.45 nM | >320 nM |
| 12060-153_3 | ccctgPGCCPPCAGACPPGCPPPAAGPPPAGCCGCPPGCPCACAPcacaa | 17 | ND | ND |
| 12060-43_3 | ccctgGGCCPPCGGACPPGCPPPAAGPPPAGCCGCPPGCPCACAPcacaa | 18 | ND | ND |
| 12060-130_3 | ccctgCGCCPPCGGACPPGCPPPAAGPPPAGCCGCPPGCPCACGPcacaa | 19 | 0.61 nM | >320 nM |
| 12060-116_3 | ccctgCGCCPPCGGACPPGCPPPAAGPPPAGCCGCPPGCPPACAPcacaa | 20 | 1.14 nM | >320 nM |
| 12060-238_3 | ccctgCGCCPPCGGACPPGCPPPACGPPPAGCCGCPPGCPCACAPcacaa | 21 | 3.4 nM | >320 nM |
| 12060-204_3 | ccctgCGCCPPCGGACPPGCPPPAAGPPPAGCCGCPCGCPCACAPcacaa | 22 | 0.94 nM | >320 nM |
| 12060-4_3 | ccctgCGCCPPCGGACPPGCPPPAAGPPPAGCCGCPPGPPCACAPcacaa | 23 | 0.90 nM | >320 nM |
| 12060-16_3 | ccctgPGAGACPPGAPPPACGPPPAGCPGCPAACAPGGGGAACCAcacaa | 13 | 6.5 nM | >320 nM |
| 12058-386_3 | ccctgGPPGACAAGGPACPGGACPPGAPPPACGPPPAGCCPCAAGcacaa | 24 | 6.7 nM | >320 nM |
| 12058-130_3 | ccctgAPGACCPAGGACPPGCPPPACGPPPAGCACGPCGAACAGGcacaa | 25 | ND | ND |
| 16139-288_3 | ctgtgCGPACPGACPPGAPPPACGPPPAGCGPGCCGAGGCcacaa | 117 | ND | ND |
| 16139-102_3 | ctgtgGAGPCPCCCGACPPGAPPPACGPPPAGCGPGCGGAGGCcacaa | 158 | ND | ND |
| 16139-85_3 | ctgtgPCCACPCAGCCGACPPGAPPPACGPPPAGCGPGCGGAGGCcacaa | 159 | ND | ND |
| 16139-12_3 | ctgtgACPAAPGPGACCGGAGACPPGCPPPACGPPPAGCGACCPGcacaa | 120 | 1.7 nM | >320 nM |
| 16139-45_3 | ctgtgAPGCCGPGGACPPGCPPPACGPPPAGCCPCGCGGGGAGCPcacaa | 121 | ND | ND |
| 16139-258_3 | ctgtgAGAGGAAAPACGCGCCPPGAPPPACGPPPAGCPGCGAPAAcacaa | 122 | ND | ND |

TABLE 6-continued

Sequence Alignment and affinity for GDF-11 specific aptamer 12060-28 (Napd U identified by "P" in the sequences), and related clones. Affinity was determined in filter binding assays in the presence of 0.1 μM Z-block. Sequences are shown full-length (50-mers). The "x" of the motif sequence may be an A or C nucleotide.

| Aptamer ID | Nucleotide Sequence (5' to 3') (P is a NapdU) | SEQ ID NO: | GDF11 (Kd) | Myostatin (Kd) |
|---|---|---|---|---|
| 16139-227_3 | ctgtgAGCGPACCPCGCACPPGAPPPACGPPPAGCGPGCGGAGGCcacaa | 123 | ND | ND |
| 16139-178_3 | ctgtgACCPPCACCCGPGACPPGGPPPACGPPPAGCGGGPAGGPcacaa | 124 | 1.08 nM | >320 nM |
| 16139-3_3 | ctgtgGACPGAGPPGGAPGGGACPPGAPPPAAGPPPAGCCCGCAAcacaa | 125 | 1.58 nM | >320 nM |
| 16139-20_3 | ctgtgGAAPGGCGACPPGAPPPAAGPPPAGCGCPACCCCCAAPPGcacaa | 126 | ND | ND |
| 16139-21_3 | ctgtgPPAGGPGCCPPGCPPPACGPPPAGCCCPACGAAACGCCPGcacaa | 127 | ND | ND |
| 16139-126_3 | ctgtgAACPPCGAPAPCGCACPPGAPPPACGPPPAGGCGGPGPCAcacaa | 128 | ND | ND |
| 16139-365_3 | ctgtgAGAGPAAAPACGCGCAPPGAPPPACGPPPAGCGPGCGGAGGCcacaa | 129 | ND | ND |
| 16139-119_3 | ctgtgPCPAGGAGCGGCPPGCPPPACGPPPAGACGGACCCCACGAcacaa | 130 | ND | ND |
| 16139-30_3 | ctgtgAGPGPACCPCGCGCPPGAPPPACGPPPAGGCGAGGCAGGCcacaa | 131 | 0.92 nM | >320 nM |
| 16139-198_3 | ctgtgAACPPGAPPPAAGPPPAGGCACAPACACCACPCCGGACGA | 132 | 0.62 nM | >320 nM |
| 16139-19_3 | ctgtgGPPAACGACGACGACPPGAPPPACGPPPAGCGGCACCPPACACcacaa | 133 | 1.70 nM | >320 nM |
| 16139-195_3 | ctgtgPCCACPCAGCCGACPPGAPPPACGPPPAGCGGCACCPPACACcacaa | 134 | ND | ND |
| 16139-360_3 | ctgtgCGPACPGACPPGAPPPACGPPPAGCGGCACCPPACACcacaa | 135 | ND | ND |
| 16139-122_3 | ctgtgCGPACPGACPPGAPPPACGPPPPAGCGAPGCAPGCPPGAGCcacaa | 136 | 2.23 nM | >320 nM |
| 16139-37_3 | ctgtgCPAAGACPGCGGACPPGAPPPAGGPPPAGCCGCAAGAAGPcacaa | 137 | 1.21 nM | >320 nM |
| 12060-28_38 | ccctgCGCCPPCGGACPPGAPPPAAGPPPAGCCGCPPGCPCACAPcacaa | 138 | 1.1 nM | >320 nM |
| 12060-28_39 | ccctgCGCCPPCGGACPPGGPPPAAGPPPAGCCGCPPGCPCACAPcacaa | 139 | 1.2 nM | >320 nM |
| 12060-28_40 | ccctgCGCCPPCGGACPPGCPPPAGGPPPAGCCGCPPGCPCACAPcacaa | 140 | 1.4 nM | >320 nM |
| Motif | GACPPGxPPPAxGPPPAGC | 26 | | |

TABLE 7

Sequence Alignment for 12060-28 (Napd U identified by "P" in the sequences), and additional related clones. Sequences are shown truncated (40-mers). The "x" of the motif sequence may be an A or C nucleotide.

| Aptamer ID | Nucleotide Sequence (5' to 3') (P is a NapdU) | SEQ ID NO: |
|---|---|---|
| 12060-28 | -CGCCPPCGGACPPGCPPPAAGPPPAGCCGCPPGCPCACAP----- | 27 |
| 12060-209 | -CGCCPPCGGACPPGCPPCAAGPPPAGCCGCPPGCPCACAP----- | 28 |
| 12060-4 | -CGCCPPCGGACPPGCPPPAAGPPPAGCCGCPPGPPCACAP----- | 29 |
| 12060-130 | -CGCCPPCGGACPPGCPPPAAGPPPAGCCGCPPGCPCACGP----- | 30 |
| 12060-204 | -CGCCPPCGGACPPGCPPPAAGPPPAGCCGCPCGCPCACAP----- | 31 |
| 12060-116 | -CGCCPPCGGACPPGCPPPAAGPPPAGCCGCPPGCPPACAP----- | 32 |
| 12060-300 | -CGCCPPCGGACPPGCPPPAAGPPPAGCCGCPPGCPCACAA----- | 33 |
| 12060-32 | -PGCCPPCGGACPPGCPPPAAGPPPAGCCGCPPGCPCACAP----- | 34 |
| 12060-43 | -GGCCPPCGGACPPGCPPPAAGPPPAGCCGCPPGCPCACAP----- | 35 |

TABLE 7-continued

Sequence Alignment for 12060-28 (Napd U identified by "P" in the sequences), and additional related clones. Sequences are shown truncated (40-mers). The "x" of the motif sequence may be an A or C nucleotide.

| Aptamer ID | Nucleotide Sequence (5' to 3') (P is a NapdU) | SEQ ID NO: |
|---|---|---|
| 12060-153 | -PGCCPPCAGACPPGCPPPAAGPPPAGCCGCPPGCPCACAP----- | 36 |
| 12060-238 | -CGCCPPCGGACPPGCPPPACGPPPAGCCGCPPGCPCACAP----- | 37 |
| 12058-111 | PPGACCPAGGACPPGCPPPACGPPPAGCACGPCGAACAGG------ | 38 |
| 12058-130 | APGACCPAGGACPPGCPPPACGPPPAGCACGPCGAACAGG------ | 39 |
| 12058-714 | APGACCPAGGAPPPGCPPPACGPPCAGCACGPCGPACAGG------ | 40 |
| 12058-284 | APGACCPAGGACPPGCPPPACGPPPAGCACGPCGAAPCGG------ | 41 |
| 12058-215 | APGACCPGGGACPPGCPPPACGPPPAGCACGPCGAACAGG------ | 42 |
| 12058-35 | APGAPCPGGGACPPGCPPPACGPPPAGCACGPCGAACAGG------ | 43 |
| 12058-59 | PPGACCPAGGACPPGCPPPACGPPPAGCAPGPGGAACAGG------ | 44 |
| 12058-546 | APGACCPAGGACPPGCPPPACGPPPAGCAGGPCGAACAGG------ | 45 |
| 12060-313 | ------PGAGACPPGACPPACGPPPAGCPGCPAACAPGGGGAACCA | 46 |
| 12060-16 | ------PGAGACPPGAPPPACGPPPAGCPGCPAACAPGGGGAACCA | 47 |
| 12060-133 | ------PGAGACPPGAPPPACGPPPAGCPGCPAACAPGGGGPACCA | 48 |
| 12060-90 | ------PGAGACPPGAPPPACGPPPAGCPGCPA-CAPGGGGAACCA | 49 |
| 12060-259 | ------PGAGACPPGAPPPACGPPPAGCPGCPAACAPGGGPAACCA | 50 |
| 12060-9 | ------PGAGACPPGAPPPACGPPPAGCPGCPAACAPGGGAAACCA | 51 |
| 12060-273 | ------PGAGACPPGAPPPACGPPPAGCPACPAACAPGGGAACCC- | 52 |
| 12060-136 | ------PGAGACPPGAPPPACGPPPAGCPGCPAACAPGGGAACCC- | 53 |
| 12060-71 | ------PGCGACPPGAPPPACGPPPAGCPGCPAACAPGGGAACCC- | 54 |
| 12060-12 | ------PGAGACPPGAPPPACGPPPAGCPGCPAACAPGGGGAACCC | 55 |
| 12060-186 | ------PGAGACPPGAPPPACGPPPAGCPGCPAACAPGGGGAPCCC | 56 |
| 12060-114 | ------PGAGACPPGAPPPACGPPPAGCPGCPAACAPGGPGAACPA | 57 |
| 12060-382 | ------PGAGACPPGAPPPACGPPPAGCPGCPAACAPGGGGAACPC | 58 |
| 12060-330 | ------PGAGACPPGAPPPACGPPPAGPPGCPAACAPGGGGAACCA | 59 |
| Motif | GACPPGxPPPAxGPPPAGC | 26 |

Example 6: GDF11 Aptamer Sequences

This example provides the results of a BLAST analysis of the SELEX aptamer pool using a lead GDF11 selective aptamer binder sequence (12060-28_3). This analysis was less stringent than the alignment performed in Example 5, and resulted in the identification of additional aptamer sequences that also contained a common or core motif. See Table 8 for the alignment of sequences.

From the alignment of the sequences in Table 8, several motif sequences may be derived, where each motif maintains overlap with the motif (or common sequence) identified from the alignment of the 102060-28_3 aptamer sequence in Examples 3 and 4.

A first motif may be defined as follows: 5'-RW$_n$MC$_n$CPPGM$_m$MPPPA$_n$AC$_n$MC$_m$RW$_n$PPG$_n$PAS$_n$GC-3' (SEQ ID NO: 110), where each P is independently, and for each occurrence, a C-5 modified pyrimidine; R is A or G; each W is independently, and for each occurrence, A, T, or U; each M is independently, and for each occurrence, A or C; S is G or C; each n is independently, and for each occurrence, 0 or 1; and each m is independently, and for each occurrence, 0 or 1.

A second motif may be defined as follows: 5'-RW$_n$AC$_n$CPPGM$_m$MPPPA$_n$AC$_n$MC$_m$RW$_n$PPG$_n$PAS$_n$GC-3' (SEQ ID NO: 111). A third motif may be as follows: 5'-RW$_n$MC$_n$CPPGM$_m$MPPPA$_n$AC$_n$MC$_m$GW$_n$PPG$_n$PAS$_n$GC-3' (SEQ ID NO: 112). A fourth motif may be as follows: 5'-RMCPPGM$_m$MPPPA$_n$AC$_n$MC$_m$RW$_n$PPAS$_n$GC-3' (SEQ ID NO: 113). In each of the second, third and fourth motifs, each P is independently, and for each occurrence, a C-5 modified pyrimidine; R is A or G; each W is independently, and for each occurrence, A, T, or U; each M is independently, and for each occurrence, A or C; S is G or C; each n is independently, and for each occurrence, 0 or 1; and each m is independently, and for each occurrence, 0 or 1.

A first motif may be defined as follows: 5'-RW$_n$MC$_n$CP-PGM$_n$MPPPA$_n$AC$_n$MC$_m$RW$_n$PPG$_n$PAS$_n$GS-3' (SEQ ID NO: 151), where each P is independently, and for each occurrence, a C-5 modified pyrimidine; R is A or G; each W is independently, and for each occurrence, A, T, or U; each M is independently, and for each occurrence, A or C; each S is independently, and for each occurrence, G or C; each n is independently, and for each occurrence, 0 or 1; and each m is independently, and for each occurrence, 0 or 1.

A second motif may be defined as follows: 5'-RW$_n$AC$_n$CPPGM$_m$MPPPA$_n$AC$_n$MC$_m$RW$_n$PPG$_n$PAS$_n$GS-3' (SEQ ID NO: 152). A third motif may be as follows: 5'-RW$_n$MC$_n$CPPGM$_m$MPPPA$_n$AC$_n$MC$_m$GW$_n$PPG$_n$PAS$_n$GS-3' (SEQ ID NO: 153). A fourth motif may be as follows: 5'-RMCPPGM$_m$MPPPA$_n$AC$_n$MC$_m$RW$_n$PP-PAS$_n$GS-3' (SEQ ID NO: 154). In each of the second, third and fourth motifs, each P is independently, and for each occurrence, a C-5 modified pyrimidine; R is A or G; each W is independently, and for each occurrence, A, T, or U; each M is independently, and for each occurrence, A or C; each S is independently, and for each occurrence, G or C; each n is independently, and for each occurrence, 0 or 1; and each m is independently, and for each occurrence, 0 or 1.

TABLE 8

Alignment of Aptamer Nucleotide Sequences with GDF11 Binder Aptamer 12060-28 (SEQ ID NO: 27)

| SEQ ID NO: | Nucleotide Sequence (5' to 3') (P is a NapdU) | GDF11 ($K_d$) |
|---|---|---|
| 27 | GCGCCPPCG G-A-CPPG-CPPP-A-A-G-PP-PA-GCC GCPPGCPCACAP | 1.7 nM |
| 60 | GPCGCCPCG G-A-C-PG-CPPP-A-A-G--P-PA-GCC GPCCPACPACCA | >320 nM |
| 61 | GCCGCCPPPCG G-A-CPPGACPPP-A-A-G-PP-PACGCPC GACPPGACPCCAPCAP | >320 nM |

TABLE 8-continued

Alignment of Aptamer Nucleotide Sequences with GDF11 Binder Aptamer 12060-28 (SEQ ID NO: 27)

| SEQ ID NO: | Nucleotide Sequence (5' to 3') (P is a NapdU) | GDF11 ($K_d$) |
|---|---|---|
| 62 | GPGCAPAAGPPCCGGGP G-A-CPPG-APPP-A-A-G-PP-PA-GCC CCCA | ND |
| 63 | GPGCCPPCCG G-A-CPPGCCPPP-A-ACG-PP-PA-GCC PAGCPPGCPCACAP | >320 nM |
| 64 | GCCGCCPPCG GPA-CPPGACPPP-A-A-GPPPGPAGGCC AGCGPPGCPCACAP | >320 nM |
| 65 | GPGA G-A-CPPG-CPPP-A-A-G-PP-PA-GCC GCPPGCPAPAP | ND |
| 66 | GCGCCPPCG G-A-CPPG-CPPP-A-A-G-PP-PA-GCC GCPPGAPCAPCPGCA | ND |
| 67 | GPCGCPACG G-A-CPPG-APPP-A-ACGP PP-PA-GCC GCPPACAPGGGAACCA | >320 nM |
| 68 | GPGPA G-A-CPPG-APPP-A-C-G-PP-PA-GCC GPAPGCPCACAP | ND |
| 69 | GCGCCPPCG G-A-CPPG-CPPA-A-A-G-PP-PA-GCC GCPPGPP | >320 nM |
| 70 | GPCGCCPPCG GPA-CPPG-CPPP-ACC-G-PP-PA-GCC ACPPAACPCACAP | ND |
| 71 | GACGGCCPPCCG G-A-CPPGACPPP-A-C-G-PP-PA-GCC GCCPGCPCACAP | ND |
| 72 | GPGCPAG G-A-CPPGACPPP-A-ACG-PP-PA-G-C PGCPPACAPGGAACPC | >320 nM |
| 73 | GCGCCPCG GAACCPPG-CPPP-A-A-G-PP-PA-GCC GCPGCPPCACAPA | ND |
| 74 | GPCGCCPCG G-A-CPPG-CPPP-A-A-GAPP-PA-GCC PGCPGCAACACAP | ND |
| 75 | GCGCPPACG G-A-CPPGACPPPAA-A-G--P-PA-GCC GCPPGCPCACCAP | ND |

The invention claimed is:

1. An aptamer that binds human GDF11, wherein the aptamer comprises the sequence 5'-RW$_n$MC$_n$CPPGM$_m$MP-PPA$_n$AC$_n$MC$_m$RW$_n$PPG$_n$PAS$_n$GC-3' (SEQ ID NO:110), wherein:
   each P is independently, and for each occurrence, a C-5 modified pyrimidine;
   R is A or G;
   each W is independently, and for each occurrence, A, T, or U;
   each M is independently, and for each occurrence, A or C;
   each S is independently, and for each occurrence, G or C;
   each n is independently, and for each occurrence, 0 or 1; and
   each m is independently, and for each occurrence, 0 or 1.

2. The aptamer of claim 1, wherein the aptamer binds human GDF11 with an affinity of less than 10 nM, wherein, under the same conditions, the aptamer binds human GDF8 with an affinity that is at least 10-fold weaker than the affinity for human GDF11 or does not bind human GDF8.

3. The aptamer of claim 2, wherein the aptamer binds GDF8 with an affinity that is at least 20-fold weaker, or at least 30-fold weaker, or at least 50-fold weaker than the affinity for GDF11.

4. The aptamer of claim 2, wherein the aptamer binds GDF8 with an affinity greater than 100 nM and binds GDF11 with an affinity of less than 8 nM.

5. The aptamer of claim 2, wherein the aptamer does not bind GDF8.

6. The aptamer of claim 4, wherein affinity is determined using a binding assay comprising a polyanionic inhibitor selected from dextran sulfate, heparin, Z-block, poly-dI/dC, sonicated or sheared salmon sperm DNA, calf thymus DNA, and dNTPs.

7. The aptamer of claim 1, wherein the aptamer comprises a sequence selected from:

a)
   (SEQ ID NO: 111)
   5'-RW$_n$AC$_n$CPPGM$_m$MPPPA$_n$AC$_n$MC$_m$RW$_n$PPG$_n$PAS$_n$GC-3'
   and b)
   (SEQ ID NO: 112)
   5'-RW$_n$MC$_n$CPPGM$_m$MPPPA$_n$AC$_n$MC$_m$GW$_n$PPG$_n$PAS$_n$GC-3'.

8. The aptamer of claim 1, wherein if R is G, the first W is A, and wherein if R is A, the first W is C.

9. The aptamer of claim 1, wherein each n is 0.

10. The aptamer of claim 1, wherein at least 1 m is 0.

11. The aptamer of claim 1, wherein the aptamer comprises the sequence 5'-CPPGMPPP-3' (SEQ ID NO: 114), wherein each P is independently, and for each occurrence, a C-5 modified pyrimidine, and wherein M is C or A.

12. The aptamer of claim 1, wherein each P is independently, and for each occurrence, selected from:
   5-(N-benzylcarboxamide)-2'-deoxyuridine (BndU),
   5-(N-benzylcarboxamide)-2'-O-methyluridine,
   5-(N-benzylcarboxamide)-2'-fluorouridine,
   5-(N-phenethylcarboxamide)-2'-deoxyuridine (PEdU),
   5-(N-thiophenylmethylcarboxamide)-2'-deoxyuridine (ThdU),
   5-(N-isobutylcarboxamide)-2'-deoxyuridine (iBudU),
   5-(N-tyrosylcarboxamide)-2'-deoxyuridine (TyrdU),
   5-(N-3,4-methylenedioxybenzylcarboxamide)-2'-deoxyuridine (MBndU),
   5-(N-4-fluorobenzylcarboxamide)-2'-deoxyuridine (FBndU), 5-(N-3-phenylpropylcarboxyamide)-2'-deoxyuridine (PPdU),
5-(N-imidizolylethylcarboxyamide)-2'-deoxyuridine (ImdU),
5-(N-isobutylcarboxyamide)-2'-O-methyluridine,
5-(N-isobutylcarboxyamide)-2'-fluorouridine,
5-(N-tryptaminocarboxyamide)-2'-deoxyuridine (TrpdU),
5-(N-R-threoninylcarboxyamide)-2'-deoxyuridine (ThrdU),
5-(N-tryptaminocarboxyamide)-2'-O-methyluridine,
5-(N-tryptaminocarboxyamide)-2'-fluorouridine,
5-(N-[1-(3-trimethylamonium) propyl]carboxyamide)-2'-deoxyuridine chloride,
5-(N-naphthylmethylcarboxyamide)-2'-deoxyuridine (NapdU),
5-(N-naphthylmethylcarboxyamide)-2'-O-methyluridine,
5-(N-naphthylmethylcarboxyamide)-2'-fluorouridine,
5-(N-[1-(2,3-dihydroxypropyl)]carboxyamide)-2'-deoxyuridine),
5-(N-2-naphthylmethylcarboxyamide)-2'-deoxyuridine (2NapdU),
5-(N-2-naphthylmethylcarboxyamide)-2'-O-methyluridine,
5-(N-2-naphthylmethylcarboxyamide)-2'-fluorouridine,
5-(N-1-naphthylethylcarboxyamide)-2'-deoxyuridine (NEdU),
5-(N-1-naphthylethylcarboxyamide)-2'-O-methyluridine,
5-(N-1-naphthylethylcarboxyamide)-2'-fluorouridine,
5-(N-2-naphthylethylcarboxyamide)-2'-deoxyuridine (2NEdU),
5-(N-2-naphthylethylcarboxyamide)-2'-O-methyluridine,
5-(N-2-naphthylethylcarboxyamide)-2'-fluorouridine,
5-(N-3-benzofuranylethylcarboxyamide)-2'-deoxyuridine (BFdU),
5-(N-3-benzofuranylethylcarboxyamide)-2'-O-methyluridine,
5-(N-3-benzofuranylethylcarboxyamide)-2'-fluorouridine,
5-(N-3-benzothiophenylethylcarboxyamide)-2'-deoxyuridine (BTdU),
5-(N-3-benzothiophenylethylcarboxyamide)-2'-O-methyluridine, and
5-(N-3-benzothiophenylethylcarboxyamide)-2'-fluorouridine.

13. The aptamer of claim 1, wherein each P is independently selected from 5-(N-naphthylmethylcarboxyamide)-2'-deoxyuridine (NapdU), 5-(N-2-naphthylmethylcarboxyamide)-2'-O-methyluridine, and 5-(N-2-naphthylmethylcarboxyamide)-2'-fluorouridine.

14. The aptamer of claim 1, wherein the aptamer consists of 18 to 100 nucleotides, wherein each nucleotide may, independently, be a modified or unmodified nucleotide.

15. A method of detecting GDF11 in a sample or determining whether a sample comprises GDF11, comprising contacting proteins from the sample with an aptamer of claim 1.

16. A composition comprising an aptamer of claim 1 and proteins from a human sample.

17. The aptamer of claim 1, wherein each P is independently selected from 5-(N-1-naphthylmethylcarboxyamide)-2'-deoxyuridine (NapdU), 5-(N-1-naphthylmethylcarboxyamide)-2'-O-methyluridine, 5-(N-1-naphthylmethylcarboxyamide)-2'-fluorouridine, 5-(N-2-naphthylmethylcarboxyamide)-2'-deoxyuridine (2NapdU), 5-(N-2-naphthylmethylcarboxyamide)-2'-O-methyluridine, 5-(N-2-naphthylmethylcarboxyamide)-2'-fluorouridine, 5-(N-1-naphthylethylcarboxyamide)-2'-deoxyuridine (NEdU), 5-(N-1-naphthylethylcarboxyamide)-2'-O-methyluridine, 5-(N-1-naphthylethylcarboxyamide)-2'-fluorouridine, 5-(N-2-naphthylethylcarboxyamide)-2'-deoxyuridine (2NEdU), 5-(N-2-naphthylethylcarboxyamide)-2'-O-methyluridine, 5-(N-2-naphthylethylcarboxyamide)-2'-fluorouridine, 5-(N-3-benzofuranylethylcarboxyamide)-2'-deoxyuridine (BFdU), 5-(N-3-benzofuranylethylcarboxyamide)-2'-O-methyluridine, 5-(N-3-benzofuranylethylcarboxyamide)-2'-fluorouridine, 5-(N-3-benzothiophenylethylcarboxyamide)-2'-deoxyuridine (BTdU), 5-(N-3-benzothiophenylethylcarboxyamide)-2'-O-methyluridine, and 5-(N-3-benzothiophenylethylcarboxyamide)-2'-fluorouridine.

18. The aptamer of claim 7, wherein each P is independently selected from 5-(N-1-naphthylmethylcarboxyamide)-2'-deoxyuridine (NapdU), 5-(N-1-naphthylmethylcarboxyamide)-2'-O-methyluridine, 5-(N-1-naphthylmethylcarboxyamide)-2'-fluorouridine, 5-(N-2-naphthylmethylcarboxyamide)-2'-deoxyuridine (2NapdU), 5-(N-2-naphthylmethylcarboxyamide)-2'-O-methyluridine, 5-(N-2-naphthylmethylcarboxyamide)-2'-fluorouridine, 5-(N-1-naphthylethylcarboxyamide)-2'-deoxyuridine (NEdU), 5-(N-1-naphthylethylcarboxyamide)-2'-O-methyluridine, 5-(N-1-naphthylethylcarboxyamide)-2'-fluorouridine, 5-(N-2-naphthylethylcarboxyamide)-2'-deoxyuridine (2NEdU), 5-(N-2-naphthylethylcarboxyamide)-2'-O-methyluridine, 5-(N-2-naphthylethylcarboxyamide)-2'-fluorouridine, 5-(N-3-benzofuranylethylcarboxyamide)-2'-deoxyuridine (BFdU), 5-(N-3-benzofuranylethylcarboxyamide)-2'-O-methyluridine, 5-(N-3-benzofuranylethylcarboxyamide)-2'-fluorouridine, 5-(N-3-benzothiophenylethylcarboxyamide)-2'-deoxyuridine (BTdU), 5-(N-3-benzothiophenylethylcarboxyamide)-2'-O-methyluridine, and 5-(N-3-benzothiophenylethylcarboxyamide)-2'-fluorouridine.

19. The aptamer of claim 11, wherein each P is independently selected from 5-(N-1-naphthylmethylcarboxyamide)-2'-deoxyuridine (NapdU), 5-(N-1-naphthylmethylcarboxyamide)-2'-O-methyluridine, 5-(N-1-naphthylmethylcarboxyamide)-2'-fluorouridine, 5-(N-2-naphthylmethylcarboxyamide)-2'-deoxyuridine (2NapdU), 5-(N-2-naphthylmethylcarboxyamide)-2'-O-methyluridine, 5-(N-2-naphthylmethylcarboxyamide)-2'-fluorouridine, 5-(N-1-naphthylethylcarboxyamide)-2'-deoxyuridine (NEdU), 5-(N-1-naphthylethylcarboxyamide)-2'-O-methyluridine, 5-(N-1-naphthylethylcarboxyamide)-2'-fluorouridine, 5-(N-2-naphthylethylcarboxyamide)-2'-deoxyuridine (2NEdU), 5-(N-2-naphthylethylcarboxyamide)-2'-O-methyluridine, 5-(N-2-naphthylethylcarboxyamide)-2'-fluorouridine, 5-(N-3-benzofuranylethylcarboxyamide)-2'-deoxyuridine (BFdU), 5-(N-3-benzofuranylethylcarboxyamide)-2'-O-methyluridine, 5-(N-3-benzofuranylethylcarboxyamide)-2'-fluorouridine, 5-(N-3-benzothiophenylethylcarboxyamide)-2'-deoxyuridine (BTdU), 5-(N-3-benzothiophenylethylcarboxyamide)-2'-O-methyluridine, and 5-(N-3-benzothiophenylethylcarboxyamide)-2'-fluorouridine.

20. The aptamer of claim 7, wherein each P is independently selected from 5-(N-naphthylmethylcarboxyamide)-2'-deoxyuridine (NapdU), 5-(N-2-naphthylmethylcarboxyamide)-2'-O-methyluridine, and 5-(N-2-naphthylmethylcarboxyamide)-2'-fluorouridine.

21. The aptamer of claim 11, wherein each P is independently selected from 5-(N-naphthylmethylcarboxyamide)-2'-deoxyuridine (NapdU), 5-(N-2-naphthylmethylcarboxyamide)-2'-O-methyluridine, and 5-(N-2-naphthylmethylcarboxyamide)-2'-fluorouridine.

\* \* \* \* \*

SEQUENCE LISTING

<160> NUMBER OF SEQ ID NOS: 160

<210> SEQ ID NO 1
<211> LENGTH: 91
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(2)
<223> OTHER INFORMATION: Biotin
<220> FEATURE:
<221> NAME/KEY: misc_feature
<222> LOCATION: (32)..(71)
<223> OTHER INFORMATION: n is a, c, g, or t

<400> SEQUENCE: 1 aattttttt  gtctcttgtt  cttgtcttgt  gnnnnnnnnn  nnnnnnnnn  nnnnnnnnn     60 nnnnnnnnn  ncagggcatc  agagcgtttc  g                                   91

-continued

<210> SEQ ID NO 2
<211> LENGTH: 28
<212> TYPE: DNA
<213> ORGANISM: Artificial Sequence
<220> FEATURE:
<223> OTHER INFORMATION: Synthetic

<400> SEQUENCE: 2
atatatatcg aaacgctctg atgccctg                                      28

<210> SEQ ID NO 3
<211> LENGTH: 31
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(2)
<223> OTHER INFORMATION: biotin

<400> SEQUENCE: 3 aattttttt gtctcttgtt cttgtcttgt g                                   31

<210> SEQ ID NO 4
<211> LENGTH: 407
<212> TYPE: PRT
<213> ORGANISM: Homo sapiens
<220> FEATURE:
<221> NAME/KEY: misc_feature
<223> OTHER INFORMATION: GDF11 (Protein ID O95390)

<400> SEQUENCE: 4

Met Val Leu Ala Ala Pro Leu Leu Leu Gly Phe Leu Leu Leu Ala Leu
1               5                   10                  15

Glu Leu Arg Pro Arg Gly Glu Ala Ala Glu Gly Pro Ala Ala Ala Ala
            20                  25                  30

Ala Ala Ala Ala Ala Ala Ala Ala Gly Val Gly Gly Glu Arg Ser
        35                  40                  45

Ser Arg Pro Ala Pro Ser Val Ala Pro Glu Pro Asp Gly Cys Pro Val
    50                  55                  60

Cys Val Trp Arg Gln His Ser Arg Glu Leu Arg Leu Glu Ser Ile Lys
65                  70                  75                  80

Ser Gln Ile Leu Ser Lys Leu Arg Leu Lys Glu Ala Pro Asn Ile Ser
                85                  90                  95

Arg Glu Val Val Lys Gln Leu Leu Pro Lys Ala Pro Pro Leu Gln Gln
            100                 105                 110

Ile Leu Asp Leu His Asp Phe Gln Gly Asp Ala Leu Gln Pro Glu Asp
        115                 120                 125

Phe Leu Glu Glu Asp Glu Tyr His Ala Thr Thr Glu Thr Val Ile Ser
    130                 135                 140

Met Ala Gln Glu Thr Asp Pro Ala Val Gln Thr Asp Gly Ser Pro Leu
145                 150                 155                 160

Cys Cys His Phe His Phe Ser Pro Lys Val Met Phe Thr Lys Val Leu
                165                 170                 175

Lys Ala Gln Leu Trp Val Tyr Leu Arg Pro Val Pro Arg Pro Ala Thr
            180                 185                 190

Val Tyr Leu Gln Ile Leu Arg Leu Lys Pro Leu Thr Gly Glu Gly Thr
        195                 200                 205

Ala Gly Gly Gly Gly Gly Arg Arg His Ile Arg Ile Arg Ser Leu
            210                 215                 220

Lys Ile Glu Leu His Ser Arg Ser Gly His Trp Gln Ser Ile Asp Phe
225                 230                 235                 240

Lys Gln Val Leu His Ser Trp Phe Arg Gln Pro Gln Ser Asn Trp Gly
                245                 250                 255

Ile Glu Ile Asn Ala Phe Asp Pro Ser Gly Thr Asp Leu Ala Val Thr
            260                 265                 270

Ser Leu Gly Pro Gly Ala Glu Gly Leu His Pro Phe Met Glu Leu Arg
                275                 280                 285

Val Leu Glu Asn Thr Lys Arg Ser Arg Arg Asn Leu Gly Leu Asp Cys
290                 295                 300

Asp Glu His Ser Ser Glu Ser Arg Cys Cys Arg Tyr Pro Leu Thr Val
305                 310                 315                 320

Asp Phe Glu Ala Phe Gly Trp Asp Trp Ile Ile Ala Pro Lys Arg Tyr
                325                 330                 335

Lys Ala Asn Tyr Cys Ser Gly Gln Cys Glu Tyr Met Phe Met Gln Lys
            340                 345                 350

Tyr Pro His Thr His Leu Val Gln Gln Ala Asn Pro Arg Gly Ser Ala
                355                 360                 365

Gly Pro Cys Cys Thr Pro Thr Lys Met Ser Pro Ile Asn Met Leu Tyr
370                 375                 380

Phe Asn Asp Lys Gln Gln Ile Ile Tyr Gly Lys Ile Pro Gly Met Val
385                 390                 395                 400

Val Asp Arg Cys Gly Cys Ser
                405

<210> SEQ ID NO 5
<211> LENGTH: 375
<212> TYPE: PRT
<213> ORGANISM: Homo sapiens
<220> FEATURE:
<221> NAME/KEY: misc_feature
<223> OTHER INFORMATION: myostatin (Protein ID 014793)

<400> SEQUENCE: 5

Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
    50                  55                  60

Arg Leu Glu Thr Ala Pro Asn Ile Ser Lys Asp Val Ile Arg Gln Leu
65                  70                  75                  80

Leu Pro Lys Ala Pro Pro Leu Arg Glu Leu Ile Asp Gln Tyr Asp Val
                85                  90                  95

Gln Arg Asp Asp Ser Ser Asp Gly Ser Leu Glu Asp Asp Tyr His
            100                 105                 110

Ala Thr Thr Glu Thr Ile Ile Thr Met Pro Thr Glu Ser Asp Phe Leu
        115                 120                 125

Met Gln Val Asp Gly Lys Pro Lys Cys Cys Phe Phe Lys Phe Ser Ser
    130                 135                 140

Lys Ile Gln Tyr Asn Lys Val Val Lys Ala Gln Leu Trp Ile Tyr Leu
145                 150                 155                 160

-continued

```
Arg Pro Val Glu Thr Pro Thr Val Phe Val Gln Ile Leu Arg Leu
            165                 170                 175

Ile Lys Pro Met Lys Asp Gly Thr Arg Tyr Thr Gly Ile Arg Ser Leu
        180                 185                 190

Lys Leu Asp Met Asn Pro Gly Thr Gly Ile Trp Gln Ser Ile Asp Val
            195                 200                 205

Lys Thr Val Leu Gln Asn Trp Leu Lys Gln Pro Glu Ser Asn Leu Gly
    210                 215                 220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
        275                 280                 285

Asp Phe Glu Ala Phe Gly Trp Asp Trp Ile Ile Ala Pro Lys Arg Tyr
    290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
            340                 345                 350

Phe Asn Gly Lys Glu Gln Ile Ile Tyr Gly Lys Ile Pro Ala Met Val
        355                 360                 365

Val Asp Arg Cys Gly Cys Ser
    370                 375

<210> SEQ ID NO 6
<211> LENGTH: 407
<212> TYPE: PRT
<213> ORGANISM: Homo sapiens
<220> FEATURE:
<221> NAME/KEY: misc_feature
<223> OTHER INFORMATION: Human GDF11 Protein ID is O95390; exemplary
      human mature GDF11

<400> SEQUENCE: 6

Met Val Leu Ala Ala Pro Leu Leu Gly Phe Leu Leu Leu Ala Leu
1               5                   10                  15

Glu Leu Arg Pro Arg Gly Glu Ala Glu Gly Pro Ala Ala Ala
            20                  25                  30

Ala Ala Ala Ala Ala Ala Ala Ala Gly Val Gly Gly Glu Arg Ser
        35                  40                  45

Ser Arg Pro Ala Pro Ser Val Ala Pro Glu Pro Asp Gly Cys Pro Val
    50                  55                  60

Cys Val Trp Arg Gln His Ser Arg Glu Leu Arg Leu Glu Ser Ile Lys
65                  70                  75                  80

Ser Gln Ile Leu Ser Lys Leu Arg Leu Lys Glu Ala Pro Asn Ile Ser
                85                  90                  95

Arg Glu Val Val Lys Gln Leu Leu Pro Lys Ala Pro Leu Gln Gln
            100                 105                 110

Ile Leu Asp Leu His Asp Phe Gln Gly Asp Ala Leu Gln Pro Glu Asp
        115                 120                 125
```

```
Phe Leu Glu Glu Asp Glu Tyr His Ala Thr Thr Glu Thr Val Ile Ser
    130                 135                 140

Met Ala Gln Glu Thr Asp Pro Ala Val Gln Thr Asp Gly Ser Pro Leu
145                 150                 155                 160

Cys Cys His Phe His Phe Ser Pro Lys Val Met Phe Thr Lys Val Leu
                165                 170                 175

Lys Ala Gln Leu Trp Val Tyr Leu Arg Pro Val Pro Arg Pro Ala Thr
                180                 185                 190

Val Tyr Leu Gln Ile Leu Arg Leu Lys Pro Leu Thr Gly Glu Gly Thr
            195                 200                 205

Ala Gly Gly Gly Gly Gly Arg Arg His Ile Arg Ile Arg Ser Leu
210                 215                 220

Lys Ile Glu Leu His Ser Arg Ser Gly His Trp Gln Ser Ile Asp Phe
225                 230                 235                 240

Lys Gln Val Leu His Ser Trp Phe Arg Gln Pro Gln Ser Asn Trp Gly
                245                 250                 255

Ile Glu Ile Asn Ala Phe Asp Pro Ser Gly Thr Asp Leu Ala Val Thr
            260                 265                 270

Ser Leu Gly Pro Gly Ala Glu Gly Leu His Pro Phe Met Glu Leu Arg
        275                 280                 285

Val Leu Glu Asn Thr Lys Arg Ser Arg Arg Asn Leu Gly Leu Asp Cys
290                 295                 300

Asp Glu His Ser Ser Glu Ser Arg Cys Cys Arg Tyr Pro Leu Thr Val
305                 310                 315                 320

Asp Phe Glu Ala Phe Gly Trp Asp Trp Ile Ile Ala Pro Lys Arg Tyr
                325                 330                 335

Lys Ala Asn Tyr Cys Ser Gly Gln Cys Glu Tyr Met Phe Met Gln Lys
                340                 345                 350

Tyr Pro His Thr His Leu Val Gln Gln Ala Asn Pro Arg Gly Ser Ala
            355                 360                 365

Gly Pro Cys Cys Thr Pro Thr Lys Met Ser Pro Ile Asn Met Leu Tyr
        370                 375                 380

Phe Asn Asp Lys Gln Gln Ile Ile Tyr Gly Lys Ile Pro Gly Met Val
385                 390                 395                 400

Val Asp Arg Cys Gly Cys Ser
                405

<210> SEQ ID NO 7
<211> LENGTH: 405
<212> TYPE: PRT
<213> ORGANISM: Mouse sp.
<220> FEATURE:
<221> NAME/KEY: misc_feature
<223> OTHER INFORMATION: Mouse GDF11 Protein ID is Q9Z1W4; exemplary
      mouse mature GDF8

<400> SEQUENCE: 7

Met Val Leu Ala Ala Pro Leu Leu Leu Gly Phe Leu Leu Leu Ala Leu
1               5                   10                  15

Glu Leu Arg Pro Arg Gly Glu Ala Ala Glu Gly Pro Ala Ala Ala Ala
                20                  25                  30

Ala Ala Ala Ala Ala Ala Gly Val Gly Gly Glu Arg Ser Ser Arg
            35                  40                  45

Pro Ala Pro Ser Ala Pro Pro Glu Pro Asp Gly Cys Pro Val Cys Val
50                  55                  60

Trp Arg Gln His Ser Arg Glu Leu Arg Leu Glu Ser Ile Lys Ser Gln
```

65                  70                  75                  80
Ile Leu Ser Lys Leu Arg Leu Lys Glu Ala Pro Asn Ile Ser Arg Glu
                    85                  90                  95

Val Val Lys Gln Leu Pro Lys Ala Pro Leu Gln Gln Ile Leu
                100                 105                 110         Leu

Asp Leu His Asp Phe Gln Gly Asp Ala Leu Gln Pro Glu Asp Phe Leu
                115                 120                 125

Glu Glu Asp Glu Tyr His Ala Thr Thr Glu Thr Val Ile Ser Met Ala
        130                 135                 140

Gln Glu Thr Asp Pro Ala Val Gln Thr Asp Gly Ser Pro Leu Cys Cys
145                 150                 155                 160

His Phe His Phe Ser Pro Lys Val Met Phe Thr Lys Val Leu Lys Ala
                    165                 170                 175

Gln Leu Trp Val Tyr Leu Arg Pro Val Pro Arg Pro Ala Thr Val Tyr
                180                 185                 190

Leu Gln Ile Leu Arg Leu Lys Pro Leu Thr Gly Glu Gly Thr Ala Gly
                195                 200                 205

Gly Gly Gly Gly Gly Arg Arg His Ile Arg Ile Arg Ser Leu Lys Ile
        210                 215                 220

Glu Leu His Ser Arg Ser Gly His Trp Gln Ser Ile Asp Phe Lys Gln
225                 230                 235                 240

Val Leu His Ser Trp Phe Arg Gln Pro Gln Ser Asn Trp Gly Ile Glu
                    245                 250                 255

Ile Asn Ala Phe Asp Pro Ser Gly Thr Asp Leu Ala Val Thr Ser Leu
                260                 265                 270

Gly Pro Gly Ala Glu Gly Leu His Pro Phe Met Glu Leu Arg Val Leu
            275                 280                 285

Glu Asn Thr Lys Arg Ser Arg Arg Asn Leu Gly Leu Asp Cys Asp Glu
            290                 295                 300

His Ser Ser Glu Ser Arg Cys Cys Arg Tyr Pro Leu Thr Val Asp Phe
305                 310                 315                 320

Glu Ala Phe Gly Trp Asp Trp Ile Ile Ala Pro Lys Arg Tyr Lys Ala
                325                 330                 335

Asn Tyr Cys Ser Gly Gln Cys Glu Tyr Met Phe Met Gln Lys Tyr Pro
                340                 345                 350

His Thr His Leu Val Gln Gln Ala Asn Pro Arg Gly Ser Ala Gly Pro
                355                 360                 365

Cys Cys Thr Pro Thr Lys Met Ser Pro Ile Asn Met Leu Tyr Phe Asn
370                 375                 380

Asp Lys Gln Gln Ile Ile Tyr Gly Lys Ile Pro Gly Met Val Val Asp
385                 390                 395                 400

Arg Cys Gly Cys Ser
                405

<210> SEQ ID NO 8
<211> LENGTH: 345
<212> TYPE: PRT
<213> ORGANISM: Rat sp.
<220> FEATURE:
<221> NAME/KEY: misc_feature
<223> OTHER INFORMATION: Rat GDF11 Protein ID is Q9Z217; exemplary rat
      mature GDF8

<400> SEQUENCE: 8

Pro Glu Pro Asp Gly Cys Pro Val Cys Val Trp Arg Gln His Ser Arg
1               5                   10                  15

Arg Val Arg Leu Gly Ser Ile Lys Ser Gln Ile Leu Ser Lys Leu Arg
            20                  25                  30

Leu Lys Glu Ala Pro Asn Ile Ser Arg Glu Val Val Lys Gln Leu Leu
        35                  40                  45

Pro Lys Ala Pro Pro Leu Gln Gln Ile Leu Asp Leu His Asp Phe Gln
    50                  55                  60

Gly Asp Ala Leu Gln Pro Glu Asp Phe Leu Glu Glu Asp Glu Tyr His
65                  70                  75                  80

Ala Thr Thr Glu Thr Val Ile Ser Met Ala Gln Glu Thr Asp Pro Ala
                85                  90                  95

Val Gln Thr Asp Gly Ser Pro Leu Cys Cys His Phe His Phe Ser Pro
            100                 105                 110

Lys Val Met Phe Thr Lys Val Leu Lys Ala Gln Leu Trp Val Tyr Leu
        115                 120                 125

Arg Pro Val Pro Arg Pro Ala Thr Val Tyr Leu Gln Ile Leu Arg Leu
    130                 135                 140

Lys Pro Leu Thr Gly Glu Gly Thr Ala Gly Gly Gly Gly Gly Gly Arg
145                 150                 155                 160

Arg His Ile Arg Ile Arg Ser Leu Lys Ile Glu Leu His Ser Arg Ser
                165                 170                 175

Gly His Trp Gln Ser Ile Asp Phe Lys Gln Val Leu His Ser Trp Phe
            180                 185                 190

Arg Gln Pro Gln Ser Asn Trp Gly Ile Glu Ile Asn Ala Phe Asp Pro
        195                 200                 205

Ser Gly Thr Asp Leu Ala Val Thr Ser Leu Gly Pro Gly Ala Glu Gly
    210                 215                 220

Cys His Pro Phe Met Glu Leu Arg Val Leu Glu Asn Thr Lys Arg Ser
225                 230                 235                 240

Arg Arg Asn Leu Gly Leu Asp Cys Asp Glu His Ser Ser Glu Ser Arg
                245                 250                 255

Cys Cys Arg Tyr Pro Leu Thr Val Asp Phe Glu Ala Ser Gly Trp Asp
            260                 265                 270

Trp Ile Ile Ala Pro Lys Arg Tyr Lys Ala Asn Tyr Cys Ser Gly Gln
        275                 280                 285

Cys Glu Tyr Met Phe Met Gln Lys Tyr Pro His Thr His Leu Val Gln
    290                 295                 300

Gln Ala Asn Pro Arg Gly Ser Ala Gly Pro Cys Cys Thr Pro Thr Lys
305                 310                 315                 320

Met Ser Pro Ile Asn Met Leu Tyr Phe Asn Asp Lys Gln Gln Ile Ile
                325                 330                 335

Tyr Gly Lys Ile Pro Gly Met Val Val
            340                 345

<210> SEQ ID NO 9
<211> LENGTH: 375
<212> TYPE: PRT
<213> ORGANISM: Homo sapiens
<220> FEATURE:
<221> NAME/KEY: misc_feature
<223> OTHER INFORMATION: Human myostatin (GDF8) Protein ID is O14793;
      exemplary human mature GDF8

<400> SEQUENCE: 9

Met Gln Lys Leu Gln Leu Cys Val Tyr Ile Tyr Leu Phe Met Leu Ile
1               5                   10                  15

```
Val Ala Gly Pro Val Asp Leu Asn Glu Asn Ser Glu Gln Lys Glu Asn
                20                  25                  30

Val Glu Lys Glu Gly Leu Cys Asn Ala Cys Thr Trp Arg Gln Asn Thr
            35                  40                  45

Lys Ser Ser Arg Ile Glu Ala Ile Lys Ile Gln Ile Leu Ser Lys Leu
50                  55                  60

Arg Leu Glu Thr Ala Pro Asn Ile Ser Lys Asp Val Ile Arg Gln Leu
65                  70                  75                  80

Leu Pro Lys Ala Pro Pro Leu Arg Glu Leu Ile Asp Gln Tyr Asp Val
                85                  90                  95

Gln Arg Asp Asp Ser Ser Asp Gly Ser Leu Glu Asp Asp Tyr His
                100                 105                 110

Ala Thr Thr Glu Thr Ile Ile Thr Met Pro Thr Glu Ser Asp Phe Leu
            115                 120                 125

Met Gln Val Asp Gly Lys Pro Lys Cys Cys Phe Phe Lys Phe Ser Ser
130                 135                 140

Lys Ile Gln Tyr Asn Lys Val Val Lys Ala Gln Leu Trp Ile Tyr Leu
145                 150                 155                 160

Arg Pro Val Glu Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
195                 200                 205

Lys Thr Val Leu Gln Asn Trp Leu Lys Gln Pro Glu Ser Asn Leu Gly
210                 215                 220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
275                 280                 285

Asp Phe Glu Ala Phe Gly Trp Asp Trp Ile Ile Ala Pro Lys Arg Tyr
290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
            340                 345                 350

Phe Asn Gly Lys Glu Gln Ile Ile Tyr Gly Lys Ile Pro Ala Met Val
355                 360                 365

Val Asp Arg Cys Gly Cys Ser
370                 375

<210> SEQ ID NO 10
<211> LENGTH: 376
<212> TYPE: PRT
<213> ORGANISM: Mouse sp.
<220> FEATURE:
<221> NAME/KEY: misc_feature
<223> OTHER INFORMATION: Mouse GDF8 Protein ID is O08689; exemplary
      mouse mature GDF8
```

```
<400> SEQUENCE: 10

Met Met Gln Lys Leu Gln Met Tyr Val Tyr Ile Tyr Leu Phe Met Leu
1               5                   10                  15

Ile Ala Ala Gly Pro Val Asp Leu Asn Glu Gly Ser Glu Arg Glu Glu
            20                  25                  30

Asn Val Glu Lys Glu Gly Leu Cys Asn Ala Cys Ala Trp Arg Gln Asn
        35                  40                  45

Thr Arg Tyr Ser Arg Ile Glu Ala Ile Lys Ile Gln Ile Leu Ser Lys
    50                  55                  60

Leu Arg Leu Glu Thr Ala Pro Asn Ile Ser Lys Asp Ala Ile Arg Gln
65                  70                  75                  80

Leu Leu Pro Arg Ala Pro Pro Leu Arg Glu Leu Ile Asp Gln Tyr Asp
                85                  90                  95

Val Gln Arg Asp Asp Ser Ser Asp Gly Ser Leu Glu Asp Asp Tyr
            100                 105                 110

His Ala Thr Thr Glu Thr Ile Ile Thr Met Pro Thr Glu Ser Asp Phe
            115                 120                 125

Leu Met Gln Ala Asp Gly Lys Pro Lys Cys Cys Phe Phe Lys Phe Ser
130                 135                 140

Ser Lys Ile Gln Tyr Asn Lys Val Val Lys Ala Gln Leu Trp Ile Tyr
145                 150                 155                 160

Leu Arg Pro Val Lys Thr Pro Thr Thr Val Phe Val Gln Ile Leu Arg
                165                 170                 175

Leu Ile Lys Pro Met Lys Asp Gly Thr Arg Tyr Thr Gly Ile Arg Ser
            180                 185                 190

Leu Lys Leu Asp Met Ser Pro Gly Thr Gly Ile Trp Gln Ser Ile Asp
        195                 200                 205

Val Lys Thr Val Leu Gln Asn Trp Leu Lys Gln Pro Glu Ser Asn Leu
    210                 215                 220

Gly Ile Glu Ile Lys Ala Leu Asp Glu Asn Gly His Asp Leu Ala Val
225                 230                 235                 240

Thr Phe Pro Gly Pro Gly Glu Asp Gly Leu Asn Pro Phe Leu Glu Val
                245                 250                 255

Lys Val Thr Asp Thr Pro Lys Arg Ser Arg Arg Asp Phe Gly Leu Asp
            260                 265                 270

Cys Asp Glu His Ser Thr Glu Ser Arg Cys Cys Arg Tyr Pro Leu Thr
        275                 280                 285

Val Asp Phe Glu Ala Phe Gly Trp Asp Trp Ile Ile Ala Pro Lys Arg
    290                 295                 300

Tyr Lys Ala Asn Tyr Cys Ser Gly Glu Cys Glu Phe Val Phe Leu Gln
305                 310                 315                 320

Lys Tyr Pro His Thr His Leu Val His Gln Ala Asn Pro Arg Gly Ser
                325                 330                 335

Ala Gly Pro Cys Cys Thr Pro Thr Lys Met Ser Pro Ile Asn Met Leu
            340                 345                 350

Tyr Phe Asn Gly Lys Glu Gln Ile Ile Tyr Gly Lys Ile Pro Ala Met
        355                 360                 365

Val Val Asp Arg Cys Gly Cys Ser
    370                 375

<210> SEQ ID NO 11
<211> LENGTH: 376
<212> TYPE: PRT
<213> ORGANISM: Rat sp.
```

<220> FEATURE:
<221> NAME/KEY: misc_feature
<223> OTHER INFORMATION: Rat GDF11 Protein ID is O35312; exemplary rat mature GDF8

<400> SEQUENCE: 11

```
Met Ile Gln Lys Pro Gln Met Tyr Val Tyr Ile Tyr Leu Phe Val Leu
1               5                   10                  15

Ile Ala Ala Gly Pro Val Asp Leu Asn Glu Asp Ser Glu Arg Glu Ala
            20                  25                  30

Asn Val Glu Lys Glu Gly Leu Cys Asn Ala Cys Ala Trp Arg Gln Asn
        35                  40                  45

Thr Arg Tyr Ser Arg Ile Glu Ala Ile Lys Ile Gln Ile Leu Ser Lys
    50                  55                  60

Leu Arg Leu Glu Thr Ala Pro Asn Ile Ser Lys Asp Ala Ile Arg Gln
65                  70                  75                  80

Leu Leu Pro Arg Ala Pro Pro Leu Arg Glu Leu Ile Asp Gln Tyr Asp
                85                  90                  95

Val Gln Arg Asp Asp Ser Ser Asp Gly Ser Leu Glu Asp Asp Asp Tyr
            100                 105                 110

His Ala Thr Thr Glu Thr Ile Ile Thr Met Pro Thr Glu Ser Asp Phe
        115                 120                 125

Leu Met Gln Ala Asp Gly Lys Pro Lys Cys Cys Phe Phe Lys Phe Ser
    130                 135                 140

Ser Lys Ile Gln Tyr Asn Lys Val Val Lys Ala Gln Leu Trp Ile Tyr
145                 150                 155                 160

Leu Arg Ala Val Lys Thr Pro Thr Thr Val Phe Val Gln Ile Leu Arg
                165                 170                 175

Leu Ile Lys Pro Met Lys Asp Gly Thr Arg Tyr Thr Gly Ile Arg Ser
            180                 185                 190

Leu Lys Leu Asp Met Ser Pro Gly Thr Gly Ile Trp Gln Ser Ile Asp
        195                 200                 205

Val Lys Thr Val Leu Gln Asn Trp Leu Lys Gln Pro Glu Ser Asn Leu
    210                 215                 220

Gly Ile Glu Ile Lys Ala Leu Asp Glu Asn Gly His Asp Leu Ala Val
225                 230                 235                 240

Thr Phe Pro Gly Pro Gly Glu Asp Gly Leu Asn Pro Phe Leu Glu Val
                245                 250                 255

Lys Val Thr Asp Thr Pro Lys Arg Ser Arg Arg Asp Phe Gly Leu Asp
            260                 265                 270

Cys Asp Glu His Ser Thr Glu Ser Arg Cys Cys Arg Tyr Pro Leu Thr
        275                 280                 285

Val Asp Phe Glu Ala Phe Gly Trp Asp Trp Ile Ile Ala Pro Lys Arg
    290                 295                 300

Tyr Lys Ala Asn Tyr Cys Ser Gly Glu Cys Glu Phe Val Phe Leu Gln
305                 310                 315                 320

Lys Tyr Pro His Thr His Leu Val His Gln Ala Asn Pro Arg Gly Ser
                325                 330                 335

Ala Gly Pro Cys Cys Thr Pro Thr Lys Met Ser Pro Ile Asn Met Leu
            340                 345                 350

Tyr Phe Asn Gly Lys Glu Gln Ile Ile Tyr Gly Lys Ile Pro Ala Met
        355                 360                 365

Val Val Asp Arg Cys Gly Cys Ser
    370                 375
```

```
<210> SEQ ID NO 12
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(11)
<223> OTHER INFORMATION: n is NapdU
<220> FEATURE:
<221> NAME/KEY: misc_feature
<222> LOCATION: (17)..(18)
<223> OTHER INFORMATION: n is NapdU
<220> FEATURE:
<221> NAME/KEY: misc_feature
<222> LOCATION: (21)..(23)
<223> OTHER INFORMATION: n is NapdU
<220> FEATURE:
<221> NAME/KEY: misc_feature
<222> LOCATION: (27)..(29)
<223> OTHER INFORMATION: n is NapdU
<220> FEATURE:
<221> NAME/KEY: misc_feature
<222> LOCATION: (36)..(37)
<223> OTHER INFORMATION: n is NapdU
<220> FEATURE:
<221> NAME/KEY: misc_feature
<222> LOCATION: (40)..(40)
<223> OTHER INFORMATION: n is NapdU
<220> FEATURE:
<221> NAME/KEY: misc_feature
<222> LOCATION: (45)..(45)
<223> OTHER INFORMATION: n is NapdU

<400> SEQUENCE: 12
ccctgcgccn ncggacnngc nnnaagnnna gccgcnngcn cacancacaa                 50

<210> SEQ ID NO 13
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: n is NapdU
<220> FEATURE:
<221> NAME/KEY: misc_feature
<222> LOCATION: (12)..(13)
<223> OTHER INFORMATION: n is NapdU
<220> FEATURE:
<221> NAME/KEY: misc_feature
<222> LOCATION: (16)..(18)
<223> OTHER INFORMATION: n is NapdU
<220> FEATURE:
<221> NAME/KEY: misc_feature
<222> LOCATION: (22)..(24)
<223> OTHER INFORMATION: n is NapdU
<220> FEATURE:
<221> NAME/KEY: misc_feature
<222> LOCATION: (28)..(28)
<223> OTHER INFORMATION: n is NapdU
<220> FEATURE:
<221> NAME/KEY: misc_feature
<222> LOCATION: (31)..(31)
<223> OTHER INFORMATION: n is NapdU
<220> FEATURE:
<221> NAME/KEY: misc_feature
<222> LOCATION: (36)..(36)
<223> OTHER INFORMATION: n is NapdU

<400> SEQUENCE: 13
ccctgngaga cnngannnac gnnnagcngc naacangggg aaccacacaa                 50
```

<210> SEQ ID NO 14
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(11)
<223> OTHER INFORMATION: n is NapdU
<220> FEATURE:
<221> NAME/KEY: misc_feature
<222> LOCATION: (17)..(18)
<223> OTHER INFORMATION: n is NapdU
<220> FEATURE:
<221> NAME/KEY: misc_feature
<222> LOCATION: (21)..(22)
<223> OTHER INFORMATION: n is NapdU
<220> FEATURE:
<221> NAME/KEY: misc_feature
<222> LOCATION: (27)..(29)
<223> OTHER INFORMATION: n is NapdU
<220> FEATURE:
<221> NAME/KEY: misc_feature
<222> LOCATION: (36)..(37)
<223> OTHER INFORMATION: n is NapdU
<220> FEATURE:
<221> NAME/KEY: misc_feature
<222> LOCATION: (40)..(40)
<223> OTHER INFORMATION: n is NapdU
<220> FEATURE:
<221> NAME/KEY: misc_feature
<222> LOCATION: (45)..(45)
<223> OTHER INFORMATION: n is NapdU

<400> SEQUENCE: 14
ccctgcgccn ncggacnngc nncaagnnna gccgcnngcn cacancacaa            50

<210> SEQ ID NO 15
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(11)
<223> OTHER INFORMATION: n is NapdU
<220> FEATURE:
<221> NAME/KEY: misc_feature
<222> LOCATION: (17)..(18)
<223> OTHER INFORMATION: n is NapdU
<220> FEATURE:
<221> NAME/KEY: misc_feature
<222> LOCATION: (21)..(23)
<223> OTHER INFORMATION: n is NapdU
<220> FEATURE:
<221> NAME/KEY: misc_feature
<222> LOCATION: (27)..(29)
<223> OTHER INFORMATION: n is NapdU
<220> FEATURE:
<221> NAME/KEY: misc_feature
<222> LOCATION: (36)..(37)
<223> OTHER INFORMATION: n is NapdU
<220> FEATURE:
<221> NAME/KEY: misc_feature
<222> LOCATION: (40)..(40)
<223> OTHER INFORMATION: n is NapdU

<400> SEQUENCE: 15
ccctgcgccn ncggacnngc nnnaagnnna gccgcnngcn cacaacacaa            50

<210> SEQ ID NO 16

```
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: n is NapdU
<220> FEATURE:
<221> NAME/KEY: misc_feature
<222> LOCATION: (10)..(11)
<223> OTHER INFORMATION: n is NapdU
<220> FEATURE:
<221> NAME/KEY: misc_feature
<222> LOCATION: (17)..(18)
<223> OTHER INFORMATION: n is NapdU
<220> FEATURE:
<221> NAME/KEY: misc_feature
<222> LOCATION: (21)..(23)
<223> OTHER INFORMATION: n is NapdU
<220> FEATURE:
<221> NAME/KEY: misc_feature
<222> LOCATION: (27)..(29)
<223> OTHER INFORMATION: n is NapdU
<220> FEATURE:
<221> NAME/KEY: misc_feature
<222> LOCATION: (36)..(37)
<223> OTHER INFORMATION: n is NapdU
<220> FEATURE:
<221> NAME/KEY: misc_feature
<222> LOCATION: (40)..(40)
<223> OTHER INFORMATION: n is NapdU
<220> FEATURE:
<221> NAME/KEY: misc_feature
<222> LOCATION: (45)..(45)
<223> OTHER INFORMATION: n is NapdU

<400> SEQUENCE: 16
ccctgngccn ncggacnngc nnnaagnnna gccgcnngcn cacancacaa         50

<210> SEQ ID NO 17
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: n is NapdU
<220> FEATURE:
<221> NAME/KEY: misc_feature
<222> LOCATION: (10)..(11)
<223> OTHER INFORMATION: n is NapdU
<220> FEATURE:
<221> NAME/KEY: misc_feature
<222> LOCATION: (17)..(18)
<223> OTHER INFORMATION: n is NapdU
<220> FEATURE:
<221> NAME/KEY: misc_feature
<222> LOCATION: (21)..(23)
<223> OTHER INFORMATION: n is NapdU
<220> FEATURE:
<221> NAME/KEY: misc_feature
<222> LOCATION: (27)..(29)
<223> OTHER INFORMATION: n is NapdU
<220> FEATURE:
<221> NAME/KEY: misc_feature
<222> LOCATION: (36)..(37)
<223> OTHER INFORMATION: n is NapdU
<220> FEATURE:
<221> NAME/KEY: misc_feature
<222> LOCATION: (40)..(40)
<223> OTHER INFORMATION: n is NapdU
<220> FEATURE:
<221> NAME/KEY: misc_feature
```

<222> LOCATION: (45)..(45)
<223> OTHER INFORMATION: n is NapdU

<400> SEQUENCE: 17
ccctgngccn ncagacnngc nnnaagnnna gccgcnngcn cacancacaa         50

<210> SEQ ID NO 18
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(11)
<223> OTHER INFORMATION: n is NapdU
<220> FEATURE:
<221> NAME/KEY: misc_feature
<222> LOCATION: (17)..(18)
<223> OTHER INFORMATION: n is NapdU
<220> FEATURE:
<221> NAME/KEY: misc_feature
<222> LOCATION: (21)..(23)
<223> OTHER INFORMATION: n is NapdU
<220> FEATURE:
<221> NAME/KEY: misc_feature
<222> LOCATION: (27)..(29)
<223> OTHER INFORMATION: n is NapdU
<220> FEATURE:
<221> NAME/KEY: misc_feature
<222> LOCATION: (36)..(37)
<223> OTHER INFORMATION: n is NapdU
<220> FEATURE:
<221> NAME/KEY: misc_feature
<222> LOCATION: (40)..(40)
<223> OTHER INFORMATION: n is NapdU
<220> FEATURE:
<221> NAME/KEY: misc_feature
<222> LOCATION: (45)..(45)
<223> OTHER INFORMATION: n is NapdU

<400> SEQUENCE: 18
ccctgggccn ncggacnngc nnnaagnnna gccgcnngcn cacancacaa         50

<210> SEQ ID NO 19
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(11)
<223> OTHER INFORMATION: n is NapdU
<220> FEATURE:
<221> NAME/KEY: misc_feature
<222> LOCATION: (17)..(18)
<223> OTHER INFORMATION: n is NapdU
<220> FEATURE:
<221> NAME/KEY: misc_feature
<222> LOCATION: (21)..(23)
<223> OTHER INFORMATION: n is NapdU
<220> FEATURE:
<221> NAME/KEY: misc_feature
<222> LOCATION: (27)..(29)
<223> OTHER INFORMATION: n is NapdU
<220> FEATURE:
<221> NAME/KEY: misc_feature
<222> LOCATION: (36)..(37)
<223> OTHER INFORMATION: n is NapdU
<220> FEATURE:
<221> NAME/KEY: misc_feature
<222> LOCATION: (40)..(40)
<223> OTHER INFORMATION: n is NapdU
<220> FEATURE:

<221> NAME/KEY: misc_feature
<222> LOCATION: (45)..(45)
<223> OTHER INFORMATION: n is NapdU

<400> SEQUENCE: 19
ccctgcgccn ncggacnngc nnnaagnnna gccgcnngcn cacgncacaa                50

<210> SEQ ID NO 20
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(11)
<223> OTHER INFORMATION: n is NapdU
<220> FEATURE:
<221> NAME/KEY: misc_feature
<222> LOCATION: (17)..(18)
<223> OTHER INFORMATION: n is NapdU
<220> FEATURE:
<221> NAME/KEY: misc_feature
<222> LOCATION: (21)..(23)
<223> OTHER INFORMATION: n is NapdU
<220> FEATURE:
<221> NAME/KEY: misc_feature
<222> LOCATION: (27)..(29)
<223> OTHER INFORMATION: n is NapdU
<220> FEATURE:
<221> NAME/KEY: misc_feature
<222> LOCATION: (36)..(37)
<223> OTHER INFORMATION: n is NapdU
<220> FEATURE:
<221> NAME/KEY: misc_feature
<222> LOCATION: (40)..(41)
<223> OTHER INFORMATION: n is NapdU
<220> FEATURE:
<221> NAME/KEY: misc_feature
<222> LOCATION: (45)..(45)
<223> OTHER INFORMATION: n is NapdU

<400> SEQUENCE: 20
ccctgcgccn ncggacnngc nnnaagnnna gccgcnngcn nacancacaa                50

<210> SEQ ID NO 21
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(11)
<223> OTHER INFORMATION: n is NapdU
<220> FEATURE:
<221> NAME/KEY: misc_feature
<222> LOCATION: (17)..(18)
<223> OTHER INFORMATION: n is NapdU
<220> FEATURE:
<221> NAME/KEY: misc_feature
<222> LOCATION: (21)..(23)
<223> OTHER INFORMATION: n is NapdU
<220> FEATURE:
<221> NAME/KEY: misc_feature
<222> LOCATION: (27)..(29)
<223> OTHER INFORMATION: n is NapdU
<220> FEATURE:
<221> NAME/KEY: misc_feature
<222> LOCATION: (36)..(37)
<223> OTHER INFORMATION: n is NapdU
<220> FEATURE:
<221> NAME/KEY: misc_feature
<222> LOCATION: (40)..(40)
<223> OTHER INFORMATION: n is NapdU

```
<220> FEATURE:
<221> NAME/KEY: misc_feature
<222> LOCATION: (45)..(45)
<223> OTHER INFORMATION: n is NapdU

<400> SEQUENCE: 21
ccctgcgccn ncggacnngc nnnacgnnna gccgcnngcn cacancacaa              50

<210> SEQ ID NO 22
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(11)
<223> OTHER INFORMATION: n is NapdU
<220> FEATURE:
<221> NAME/KEY: misc_feature
<222> LOCATION: (17)..(18)
<223> OTHER INFORMATION: n is NapdU
<220> FEATURE:
<221> NAME/KEY: misc_feature
<222> LOCATION: (21)..(23)
<223> OTHER INFORMATION: n is NapdU
<220> FEATURE:
<221> NAME/KEY: misc_feature
<222> LOCATION: (27)..(29)
<223> OTHER INFORMATION: n is NapdU
<220> FEATURE:
<221> NAME/KEY: misc_feature
<222> LOCATION: (36)..(36)
<223> OTHER INFORMATION: n is NapdU
<220> FEATURE:
<221> NAME/KEY: misc_feature
<222> LOCATION: (40)..(40)
<223> OTHER INFORMATION: n is NapdU
<220> FEATURE:
<221> NAME/KEY: misc_feature
<222> LOCATION: (45)..(45)
<223> OTHER INFORMATION: n is NapdU

<400> SEQUENCE: 22
ccctgcgccn ncggacnngc nnnaagnnna gccgcncgcn cacancacaa              50

<210> SEQ ID NO 23
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(11)
<223> OTHER INFORMATION: n is NapdU
<220> FEATURE:
<221> NAME/KEY: misc_feature
<222> LOCATION: (17)..(18)
<223> OTHER INFORMATION: n is NapdU
<220> FEATURE:
<221> NAME/KEY: misc_feature
<222> LOCATION: (21)..(23)
<223> OTHER INFORMATION: n is NapdU
<220> FEATURE:
<221> NAME/KEY: misc_feature
<222> LOCATION: (27)..(29)
<223> OTHER INFORMATION: n is NapdU
<220> FEATURE:
<221> NAME/KEY: misc_feature
<222> LOCATION: (36)..(37)
<223> OTHER INFORMATION: n is NapdU
<220> FEATURE:
<221> NAME/KEY: misc_feature
<222> LOCATION: (39)..(40)
```

<223> OTHER INFORMATION: n is NapdU
<220> FEATURE:
<221> NAME/KEY: misc_feature
<222> LOCATION: (45)..(45)
<223> OTHER INFORMATION: n is NapdU

<400> SEQUENCE: 23
ccctgcgccn ncggacnngc nnnaagnnna gccgcnngnn cacancacaa    50

<210> SEQ ID NO 24
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(8)
<223> OTHER INFORMATION: n is NapdU
<220> FEATURE:
<221> NAME/KEY: misc_feature
<222> LOCATION: (16)..(16)
<223> OTHER INFORMATION: n is NapdU
<220> FEATURE:
<221> NAME/KEY: misc_feature
<222> LOCATION: (19)..(19)
<223> OTHER INFORMATION: n is NapdU
<220> FEATURE:
<221> NAME/KEY: misc_feature
<222> LOCATION: (24)..(25)
<223> OTHER INFORMATION: n is NapdU
<220> FEATURE:
<221> NAME/KEY: misc_feature
<222> LOCATION: (28)..(30)
<223> OTHER INFORMATION: n is NapdU
<220> FEATURE:
<221> NAME/KEY: misc_feature
<222> LOCATION: (34)..(36)
<223> OTHER INFORMATION: n is NapdU
<220> FEATURE:
<221> NAME/KEY: misc_feature
<222> LOCATION: (41)..(41)
<223> OTHER INFORMATION: n is NapdU

<400> SEQUENCE: 24
ccctggnnga caaggnacng gacnngannn acgnnnagcc ncaagcacaa    50

<210> SEQ ID NO 25
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: n is NapdU
<220> FEATURE:
<221> NAME/KEY: misc_feature
<222> LOCATION: (12)..(12)
<223> OTHER INFORMATION: n is NapdU
<220> FEATURE:
<221> NAME/KEY: misc_feature
<222> LOCATION: (18)..(19)
<223> OTHER INFORMATION: n is NapdU
<220> FEATURE:
<221> NAME/KEY: misc_feature
<222> LOCATION: (22)..(24)
<223> OTHER INFORMATION: n is NapdU
<220> FEATURE:
<221> NAME/KEY: misc_feature
<222> LOCATION: (28)..(30)
<223> OTHER INFORMATION: n is NapdU
<220> FEATURE:
<221> NAME/KEY: misc_feature

```
<222> LOCATION: (37)..(37)
<223> OTHER INFORMATION: n is NapdU

<400> SEQUENCE: 25
ccctgangac cnaggacnng cnnnacgnnn agcacgncga acaggcacaa         50

<210> SEQ ID NO 26
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: n is NapdU
<220> FEATURE:
<221> NAME/KEY: misc_feature
<222> LOCATION: (7)..(7)
<223> OTHER INFORMATION: n is a or c
<220> FEATURE:
<221> NAME/KEY: misc_feature
<222> LOCATION: (8)..(10)
<223> OTHER INFORMATION: n is NapdU
<220> FEATURE:
<221> NAME/KEY: misc_feature
<222> LOCATION: (12)..(12)
<223> OTHER INFORMATION: n is a or c
<220> FEATURE:
<221> NAME/KEY: misc_feature
<222> LOCATION: (14)..(16)
<223> OTHER INFORMATION: n is NapdU

<400> SEQUENCE: 26
gacnngnnnn angnnnagc                                          19

<210> SEQ ID NO 27
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: n is NapdU
<220> FEATURE:
<221> NAME/KEY: misc_feature
<222> LOCATION: (12)..(13)
<223> OTHER INFORMATION: n is NapdU
<220> FEATURE:
<221> NAME/KEY: misc_feature
<222> LOCATION: (16)..(18)
<223> OTHER INFORMATION: n is NapdU
<220> FEATURE:
<221> NAME/KEY: misc_feature
<222> LOCATION: (22)..(24)
<223> OTHER INFORMATION: n is NapdU
<220> FEATURE:
<221> NAME/KEY: misc_feature
<222> LOCATION: (31)..(32)
<223> OTHER INFORMATION: n is NapdU
<220> FEATURE:
<221> NAME/KEY: misc_feature
<222> LOCATION: (35)..(35)
<223> OTHER INFORMATION: n is NapdU
<220> FEATURE:
<221> NAME/KEY: misc_feature
<222> LOCATION: (40)..(40)
<223> OTHER INFORMATION: n is NapdU

<400> SEQUENCE: 27
cgccnncgga cnngcnnnaa gnnnagccgc nngcncacan                   40
```

```
<210> SEQ ID NO 28
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: n is NapdU
<220> FEATURE:
<221> NAME/KEY: misc_feature
<222> LOCATION: (12)..(13)
<223> OTHER INFORMATION: n is NapdU
<220> FEATURE:
<221> NAME/KEY: misc_feature
<222> LOCATION: (16)..(17)
<223> OTHER INFORMATION: n is NapdU
<220> FEATURE:
<221> NAME/KEY: misc_feature
<222> LOCATION: (22)..(24)
<223> OTHER INFORMATION: n is NapdU
<220> FEATURE:
<221> NAME/KEY: misc_feature
<222> LOCATION: (31)..(32)
<223> OTHER INFORMATION: n is NapdU
<220> FEATURE:
<221> NAME/KEY: misc_feature
<222> LOCATION: (35)..(35)
<223> OTHER INFORMATION: n is NapdU
<220> FEATURE:
<221> NAME/KEY: misc_feature
<222> LOCATION: (40)..(40)
<223> OTHER INFORMATION: n is NapdU

<400> SEQUENCE: 28
cgccnncgga cnngcnncaa gnnnagccgc nngcncacan                              40

<210> SEQ ID NO 29
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: n is NapdU
<220> FEATURE:
<221> NAME/KEY: misc_feature
<222> LOCATION: (12)..(13)
<223> OTHER INFORMATION: n is NapdU
<220> FEATURE:
<221> NAME/KEY: misc_feature
<222> LOCATION: (16)..(18)
<223> OTHER INFORMATION: n is NapdU
<220> FEATURE:
<221> NAME/KEY: misc_feature
<222> LOCATION: (22)..(24)
<223> OTHER INFORMATION: n is NapdU
<220> FEATURE:
<221> NAME/KEY: misc_feature
<222> LOCATION: (31)..(32)
<223> OTHER INFORMATION: n is NapdU
<220> FEATURE:
<221> NAME/KEY: misc_feature
<222> LOCATION: (34)..(35)
<223> OTHER INFORMATION: n is NapdU
<220> FEATURE:
<221> NAME/KEY: misc_feature
<222> LOCATION: (40)..(40)
<223> OTHER INFORMATION: n is NapdU

<400> SEQUENCE: 29
cgccnncgga cnngcnnnaa gnnnagccgc nngnncacan                              40
```

<210> SEQ ID NO 30
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: n is NapdU
<220> FEATURE:
<221> NAME/KEY: misc_feature
<222> LOCATION: (12)..(13)
<223> OTHER INFORMATION: n is NapdU
<220> FEATURE:
<221> NAME/KEY: misc_feature
<222> LOCATION: (16)..(18)
<223> OTHER INFORMATION: n is NapdU
<220> FEATURE:
<221> NAME/KEY: misc_feature
<222> LOCATION: (22)..(24)
<223> OTHER INFORMATION: n is NapdU
<220> FEATURE:
<221> NAME/KEY: misc_feature
<222> LOCATION: (31)..(32)
<223> OTHER INFORMATION: n is NapdU
<220> FEATURE:
<221> NAME/KEY: misc_feature
<222> LOCATION: (35)..(35)
<223> OTHER INFORMATION: n is NapdU
<220> FEATURE:
<221> NAME/KEY: misc_feature
<222> LOCATION: (40)..(40)
<223> OTHER INFORMATION: n is NapdU

<400> SEQUENCE: 30
cgccnncgga cnngcnnnaa gnnnagccgc nngcncacgn                            40

<210> SEQ ID NO 31
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: n is NapdU
<220> FEATURE:
<221> NAME/KEY: misc_feature
<222> LOCATION: (12)..(13)
<223> OTHER INFORMATION: n is NapdU
<220> FEATURE:
<221> NAME/KEY: misc_feature
<222> LOCATION: (16)..(18)
<223> OTHER INFORMATION: n is NapdU
<220> FEATURE:
<221> NAME/KEY: misc_feature
<222> LOCATION: (22)..(24)
<223> OTHER INFORMATION: n is NapdU
<220> FEATURE:
<221> NAME/KEY: misc_feature
<222> LOCATION: (31)..(31)
<223> OTHER INFORMATION: n is NapdU
<220> FEATURE:
<221> NAME/KEY: misc_feature
<222> LOCATION: (35)..(35)
<223> OTHER INFORMATION: n is NapdU
<220> FEATURE:
<221> NAME/KEY: misc_feature
<222> LOCATION: (40)..(40)
<223> OTHER INFORMATION: n is NapdU

<400> SEQUENCE: 31
cgccnncgga cnngcnnnaa gnnnagccgc ncgcncacan        40

<210> SEQ ID NO 32
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: n is NapdU
<220> FEATURE:
<221> NAME/KEY: misc_feature
<222> LOCATION: (12)..(13)
<223> OTHER INFORMATION: n is NapdU
<220> FEATURE:
<221> NAME/KEY: misc_feature
<222> LOCATION: (16)..(18)
<223> OTHER INFORMATION: n is NapdU
<220> FEATURE:
<221> NAME/KEY: misc_feature
<222> LOCATION: (22)..(24)
<223> OTHER INFORMATION: n is NapdU
<220> FEATURE:
<221> NAME/KEY: misc_feature
<222> LOCATION: (31)..(32)
<223> OTHER INFORMATION: n is NapdU
<220> FEATURE:
<221> NAME/KEY: misc_feature
<222> LOCATION: (35)..(36)
<223> OTHER INFORMATION: n is NapdU
<220> FEATURE:
<221> NAME/KEY: misc_feature
<222> LOCATION: (40)..(40)
<223> OTHER INFORMATION: n is NapdU

<400> SEQUENCE: 32
cgccnncgga cnngcnnnaa gnnnagccgc nngcnnacan        40

<210> SEQ ID NO 33
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: n is NapdU
<220> FEATURE:
<221> NAME/KEY: misc_feature
<222> LOCATION: (12)..(13)
<223> OTHER INFORMATION: n is NapdU
<220> FEATURE:
<221> NAME/KEY: misc_feature
<222> LOCATION: (16)..(18)
<223> OTHER INFORMATION: n is NapdU
<220> FEATURE:
<221> NAME/KEY: misc_feature
<222> LOCATION: (22)..(24)
<223> OTHER INFORMATION: n is NapdU
<220> FEATURE:
<221> NAME/KEY: misc_feature
<222> LOCATION: (31)..(32)
<223> OTHER INFORMATION: n is NapdU
<220> FEATURE:
<221> NAME/KEY: misc_feature
<222> LOCATION: (35)..(35)
<223> OTHER INFORMATION: n is NapdU

<400> SEQUENCE: 33
cgccnncgga cnngcnnnaa gnnnagccgc nngcncacaa        40

```
<210> SEQ ID NO 34
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is NapdU
<220> FEATURE:
<221> NAME/KEY: misc_feature
<222> LOCATION: (5)..(6)
<223> OTHER INFORMATION: n is NapdU
<220> FEATURE:
<221> NAME/KEY: misc_feature
<222> LOCATION: (12)..(13)
<223> OTHER INFORMATION: n is NapdU
<220> FEATURE:
<221> NAME/KEY: misc_feature
<222> LOCATION: (16)..(18)
<223> OTHER INFORMATION: n is NapdU
<220> FEATURE:
<221> NAME/KEY: misc_feature
<222> LOCATION: (22)..(24)
<223> OTHER INFORMATION: n is NapdU
<220> FEATURE:
<221> NAME/KEY: misc_feature
<222> LOCATION: (31)..(32)
<223> OTHER INFORMATION: n is NapdU
<220> FEATURE:
<221> NAME/KEY: misc_feature
<222> LOCATION: (35)..(35)
<223> OTHER INFORMATION: n is NapdU
<220> FEATURE:
<221> NAME/KEY: misc_feature
<222> LOCATION: (40)..(40)
<223> OTHER INFORMATION: n is NapdU

<400> SEQUENCE: 34
ngccnncgga cnngcnnnaa gnnnagccgc nngcncacan                40

<210> SEQ ID NO 35
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: n is NapdU
<220> FEATURE:
<221> NAME/KEY: misc_feature
<222> LOCATION: (12)..(13)
<223> OTHER INFORMATION: n is NapdU
<220> FEATURE:
<221> NAME/KEY: misc_feature
<222> LOCATION: (16)..(18)
<223> OTHER INFORMATION: n is NapdU
<220> FEATURE:
<221> NAME/KEY: misc_feature
<222> LOCATION: (22)..(24)
<223> OTHER INFORMATION: n is NapdU
<220> FEATURE:
<221> NAME/KEY: misc_feature
<222> LOCATION: (31)..(32)
<223> OTHER INFORMATION: n is NapdU
<220> FEATURE:
<221> NAME/KEY: misc_feature
<222> LOCATION: (35)..(35)
<223> OTHER INFORMATION: n is NapdU
<220> FEATURE:
<221> NAME/KEY: misc_feature
<222> LOCATION: (40)..(40)
<223> OTHER INFORMATION: n is NapdU
```

<400> SEQUENCE: 35
ggccnncgga cnngcnnnaa gnnnagccgc nngcncacan    40

<210> SEQ ID NO 36
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is NapdU
<220> FEATURE:
<221> NAME/KEY: misc_feature
<222> LOCATION: (5)..(6)
<223> OTHER INFORMATION: n is NapdU
<220> FEATURE:
<221> NAME/KEY: misc_feature
<222> LOCATION: (12)..(13)
<223> OTHER INFORMATION: n is NapdU
<220> FEATURE:
<221> NAME/KEY: misc_feature
<222> LOCATION: (16)..(18)
<223> OTHER INFORMATION: n is NapdU
<220> FEATURE:
<221> NAME/KEY: misc_feature
<222> LOCATION: (22)..(24)
<223> OTHER INFORMATION: n is NapdU
<220> FEATURE:
<221> NAME/KEY: misc_feature
<222> LOCATION: (31)..(32)
<223> OTHER INFORMATION: n is NapdU
<220> FEATURE:
<221> NAME/KEY: misc_feature
<222> LOCATION: (35)..(35)
<223> OTHER INFORMATION: n is NapdU
<220> FEATURE:
<221> NAME/KEY: misc_feature
<222> LOCATION: (40)..(40)
<223> OTHER INFORMATION: n is NapdU

<400> SEQUENCE: 36
ngccnncaga cnngcnnnaa gnnnagccgc nngcncacan    40

<210> SEQ ID NO 37
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: n is NapdU
<220> FEATURE:
<221> NAME/KEY: misc_feature
<222> LOCATION: (12)..(13)
<223> OTHER INFORMATION: n is NapdU
<220> FEATURE:
<221> NAME/KEY: misc_feature
<222> LOCATION: (16)..(18)
<223> OTHER INFORMATION: n is NapdU
<220> FEATURE:
<221> NAME/KEY: misc_feature
<222> LOCATION: (22)..(24)
<223> OTHER INFORMATION: n is NapdU
<220> FEATURE:
<221> NAME/KEY: misc_feature
<222> LOCATION: (31)..(32)
<223> OTHER INFORMATION: n is NapdU
<220> FEATURE:
<221> NAME/KEY: misc_feature
<222> LOCATION: (35)..(35)
<223> OTHER INFORMATION: n is NapdU

```
<220> FEATURE:
<221> NAME/KEY: misc_feature
<222> LOCATION: (40)..(40)
<223> OTHER INFORMATION: n is NapdU

<400> SEQUENCE: 37
cgccnncgga cnngcnnnac gnnnagccgc nngcncacan                    40

<210> SEQ ID NO 38
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is NapdU
<220> FEATURE:
<221> NAME/KEY: misc_feature
<222> LOCATION: (7)..(7)
<223> OTHER INFORMATION: n is NapdU
<220> FEATURE:
<221> NAME/KEY: misc_feature
<222> LOCATION: (13)..(14)
<223> OTHER INFORMATION: n is NapdU
<220> FEATURE:
<221> NAME/KEY: misc_feature
<222> LOCATION: (17)..(19)
<223> OTHER INFORMATION: n is NapdU
<220> FEATURE:
<221> NAME/KEY: misc_feature
<222> LOCATION: (23)..(25)
<223> OTHER INFORMATION: n is NapdU
<220> FEATURE:
<221> NAME/KEY: misc_feature
<222> LOCATION: (32)..(32)
<223> OTHER INFORMATION: n is NapdU

<400> SEQUENCE: 38
nngaccnagg acnngcnnna cgnnnagcac gncgaacagg                    40

<210> SEQ ID NO 39
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: n is NapdU
<220> FEATURE:
<221> NAME/KEY: misc_feature
<222> LOCATION: (7)..(7)
<223> OTHER INFORMATION: n is NapdU
<220> FEATURE:
<221> NAME/KEY: misc_feature
<222> LOCATION: (13)..(14)
<223> OTHER INFORMATION: n is NapdU
<220> FEATURE:
<221> NAME/KEY: misc_feature
<222> LOCATION: (17)..(19)
<223> OTHER INFORMATION: n is NapdU
<220> FEATURE:
<221> NAME/KEY: misc_feature
<222> LOCATION: (23)..(25)
<223> OTHER INFORMATION: n is NapdU
<220> FEATURE:
<221> NAME/KEY: misc_feature
<222> LOCATION: (32)..(32)
<223> OTHER INFORMATION: n is NapdU

<400> SEQUENCE: 39
```
angaccnagg acnngcnnna cgnnnagcac gncgaacagg        40

<210> SEQ ID NO 40
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: n is NapdU
<220> FEATURE:
<221> NAME/KEY: misc_feature
<222> LOCATION: (7)..(7)
<223> OTHER INFORMATION: n is NapdU
<220> FEATURE:
<221> NAME/KEY: misc_feature
<222> LOCATION: (12)..(14)
<223> OTHER INFORMATION: n is NapdU
<220> FEATURE:
<221> NAME/KEY: misc_feature
<222> LOCATION: (17)..(19)
<223> OTHER INFORMATION: n is NapdU
<220> FEATURE:
<221> NAME/KEY: misc_feature
<222> LOCATION: (23)..(24)
<223> OTHER INFORMATION: n is NapdU
<220> FEATURE:
<221> NAME/KEY: misc_feature
<222> LOCATION: (32)..(32)
<223> OTHER INFORMATION: n is NapdU
<220> FEATURE:
<221> NAME/KEY: misc_feature
<222> LOCATION: (35)..(35)
<223> OTHER INFORMATION: n is NapdU

<400> SEQUENCE: 40
angaccnagg annngcnnna cgnncagcac gncgnacagg        40

<210> SEQ ID NO 41
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: n is NapdU
<220> FEATURE:
<221> NAME/KEY: misc_feature
<222> LOCATION: (7)..(7)
<223> OTHER INFORMATION: n is NapdU
<220> FEATURE:
<221> NAME/KEY: misc_feature
<222> LOCATION: (13)..(14)
<223> OTHER INFORMATION: n is NapdU
<220> FEATURE:
<221> NAME/KEY: misc_feature
<222> LOCATION: (17)..(19)
<223> OTHER INFORMATION: n is NapdU
<220> FEATURE:
<221> NAME/KEY: misc_feature
<222> LOCATION: (23)..(25)
<223> OTHER INFORMATION: n is NapdU
<220> FEATURE:
<221> NAME/KEY: misc_feature
<222> LOCATION: (32)..(32)
<223> OTHER INFORMATION: n is NapdU
<220> FEATURE:
<221> NAME/KEY: misc_feature
<222> LOCATION: (37)..(37)
<223> OTHER INFORMATION: n is NapdU

<400> SEQUENCE: 41

```
angaccnagg acnngcnnna cgnnnagcac gncgaancgg                            40
```

<210> SEQ ID NO 42
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: n is NapdU
<220> FEATURE:
<221> NAME/KEY: misc_feature
<222> LOCATION: (7)..(7)
<223> OTHER INFORMATION: n is NapdU
<220> FEATURE:
<221> NAME/KEY: misc_feature
<222> LOCATION: (13)..(14)
<223> OTHER INFORMATION: n is NapdU
<220> FEATURE:
<221> NAME/KEY: misc_feature
<222> LOCATION: (17)..(19)
<223> OTHER INFORMATION: n is NapdU
<220> FEATURE:
<221> NAME/KEY: misc_feature
<222> LOCATION: (23)..(25)
<223> OTHER INFORMATION: n is NapdU
<220> FEATURE:
<221> NAME/KEY: misc_feature
<222> LOCATION: (32)..(32)
<223> OTHER INFORMATION: n is NapdU

<400> SEQUENCE: 42

```
angaccnggg acnngcnnna cgnnnagcac gncgaacagg                            40
```

<210> SEQ ID NO 43
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: n is NapdU
<220> FEATURE:
<221> NAME/KEY: misc_feature
<222> LOCATION: (5)..(5)
<223> OTHER INFORMATION: n is NapdU
<220> FEATURE:
<221> NAME/KEY: misc_feature
<222> LOCATION: (7)..(7)
<223> OTHER INFORMATION: n is NapdU
<220> FEATURE:
<221> NAME/KEY: misc_feature
<222> LOCATION: (13)..(14)
<223> OTHER INFORMATION: n is NapdU
<220> FEATURE:
<221> NAME/KEY: misc_feature
<222> LOCATION: (17)..(19)
<223> OTHER INFORMATION: n is NapdU
<220> FEATURE:
<221> NAME/KEY: misc_feature
<222> LOCATION: (23)..(25)
<223> OTHER INFORMATION: n is NapdU
<220> FEATURE:
<221> NAME/KEY: misc_feature
<222> LOCATION: (32)..(32)
<223> OTHER INFORMATION: n is NapdU

<400> SEQUENCE: 43

```
angancnggg acnngcnnna cgnnnagcac gncgaacagg                            40
```

```
<210> SEQ ID NO 44
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is NapdU
<220> FEATURE:
<221> NAME/KEY: misc_feature
<222> LOCATION: (7)..(7)
<223> OTHER INFORMATION: n is NapdU
<220> FEATURE:
<221> NAME/KEY: misc_feature
<222> LOCATION: (13)..(14)
<223> OTHER INFORMATION: n is NapdU
<220> FEATURE:
<221> NAME/KEY: misc_feature
<222> LOCATION: (17)..(19)
<223> OTHER INFORMATION: n is NapdU
<220> FEATURE:
<221> NAME/KEY: misc_feature
<222> LOCATION: (23)..(25)
<223> OTHER INFORMATION: n is NapdU
<220> FEATURE:
<221> NAME/KEY: misc_feature
<222> LOCATION: (30)..(30)
<223> OTHER INFORMATION: n is NapdU
<220> FEATURE:
<221> NAME/KEY: misc_feature
<222> LOCATION: (32)..(32)
<223> OTHER INFORMATION: n is NapdU

<400> SEQUENCE: 44
nngaccnagg acnngcnnna cgnnnagcan gnggaacagg                              40

<210> SEQ ID NO 45
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: n is NapdU
<220> FEATURE:
<221> NAME/KEY: misc_feature
<222> LOCATION: (7)..(7)
<223> OTHER INFORMATION: n is NapdU
<220> FEATURE:
<221> NAME/KEY: misc_feature
<222> LOCATION: (13)..(14)
<223> OTHER INFORMATION: n is NapdU
<220> FEATURE:
<221> NAME/KEY: misc_feature
<222> LOCATION: (17)..(19)
<223> OTHER INFORMATION: n is NapdU
<220> FEATURE:
<221> NAME/KEY: misc_feature
<222> LOCATION: (23)..(25)
<223> OTHER INFORMATION: n is NapdU
<220> FEATURE:
<221> NAME/KEY: misc_feature
<222> LOCATION: (32)..(32)
<223> OTHER INFORMATION: n is NapdU

<400> SEQUENCE: 45
angaccnagg acnngcnnna cgnnnagcag gncgaacagg                              40

<210> SEQ ID NO 46
<211> LENGTH: 40
```

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is NapdU
<220> FEATURE:
<221> NAME/KEY: misc_feature
<222> LOCATION: (7)..(8)
<223> OTHER INFORMATION: n is NapdU
<220> FEATURE:
<221> NAME/KEY: misc_feature
<222> LOCATION: (12)..(13)
<223> OTHER INFORMATION: n is NapdU
<220> FEATURE:
<221> NAME/KEY: misc_feature
<222> LOCATION: (17)..(19)
<223> OTHER INFORMATION: n is NapdU
<220> FEATURE:
<221> NAME/KEY: misc_feature
<222> LOCATION: (23)..(23)
<223> OTHER INFORMATION: n is NapdU
<220> FEATURE:
<221> NAME/KEY: misc_feature
<222> LOCATION: (26)..(26)
<223> OTHER INFORMATION: n is NapdU
<220> FEATURE:
<221> NAME/KEY: misc_feature
<222> LOCATION: (31)..(31)
<223> OTHER INFORMATION: n is NapdU

<400> SEQUENCE: 46
ngagacnnga cnnacgnnna gcngcnaaca nggggaacca         40

<210> SEQ ID NO 47
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is NapdU
<220> FEATURE:
<221> NAME/KEY: misc_feature
<222> LOCATION: (7)..(8)
<223> OTHER INFORMATION: n is NapdU
<220> FEATURE:
<221> NAME/KEY: misc_feature
<222> LOCATION: (11)..(13)
<223> OTHER INFORMATION: n is NapdU
<220> FEATURE:
<221> NAME/KEY: misc_feature
<222> LOCATION: (17)..(19)
<223> OTHER INFORMATION: n is NapdU
<220> FEATURE:
<221> NAME/KEY: misc_feature
<222> LOCATION: (23)..(23)
<223> OTHER INFORMATION: n is NapdU
<220> FEATURE:
<221> NAME/KEY: misc_feature
<222> LOCATION: (26)..(26)
<223> OTHER INFORMATION: n is NapdU
<220> FEATURE:
<221> NAME/KEY: misc_feature
<222> LOCATION: (31)..(31)
<223> OTHER INFORMATION: n is NapdU

<400> SEQUENCE: 47
ngagacnnga nnnacgnnna gcngcnaaca nggggaacca         40

<210> SEQ ID NO 48
```

```
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is NapdU
<220> FEATURE:
<221> NAME/KEY: misc_feature
<222> LOCATION: (7)..(8)
<223> OTHER INFORMATION: n is NapdU
<220> FEATURE:
<221> NAME/KEY: misc_feature
<222> LOCATION: (11)..(13)
<223> OTHER INFORMATION: n is NapdU
<220> FEATURE:
<221> NAME/KEY: misc_feature
<222> LOCATION: (17)..(19)
<223> OTHER INFORMATION: n is NapdU
<220> FEATURE:
<221> NAME/KEY: misc_feature
<222> LOCATION: (23)..(23)
<223> OTHER INFORMATION: n is NapdU
<220> FEATURE:
<221> NAME/KEY: misc_feature
<222> LOCATION: (26)..(26)
<223> OTHER INFORMATION: n is NapdU
<220> FEATURE:
<221> NAME/KEY: misc_feature
<222> LOCATION: (31)..(31)
<223> OTHER INFORMATION: n is NapdU
<220> FEATURE:
<221> NAME/KEY: misc_feature
<222> LOCATION: (36)..(36)
<223> OTHER INFORMATION: n is NapdU

<400> SEQUENCE: 48
ngagacnnga nnnacgnnna gcngcnaaca nggggnacca                40

<210> SEQ ID NO 49
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is NapdU
<220> FEATURE:
<221> NAME/KEY: misc_feature
<222> LOCATION: (7)..(8)
<223> OTHER INFORMATION: n is NapdU
<220> FEATURE:
<221> NAME/KEY: misc_feature
<222> LOCATION: (11)..(13)
<223> OTHER INFORMATION: n is NapdU
<220> FEATURE:
<221> NAME/KEY: misc_feature
<222> LOCATION: (17)..(19)
<223> OTHER INFORMATION: n is NapdU
<220> FEATURE:
<221> NAME/KEY: misc_feature
<222> LOCATION: (23)..(23)
<223> OTHER INFORMATION: n is NapdU
<220> FEATURE:
<221> NAME/KEY: misc_feature
<222> LOCATION: (26)..(26)
<223> OTHER INFORMATION: n is NapdU
<220> FEATURE:
<221> NAME/KEY: misc_feature
<222> LOCATION: (30)..(30)
<223> OTHER INFORMATION: n is NapdU

<400> SEQUENCE: 49
```
ngagacnnga nnnacgnnna gcngcnacan ggggaacca          39

<210> SEQ ID NO 50
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is NapdU
<220> FEATURE:
<221> NAME/KEY: misc_feature
<222> LOCATION: (7)..(8)
<223> OTHER INFORMATION: n is NapdU
<220> FEATURE:
<221> NAME/KEY: misc_feature
<222> LOCATION: (11)..(13)
<223> OTHER INFORMATION: n is NapdU
<220> FEATURE:
<221> NAME/KEY: misc_feature
<222> LOCATION: (17)..(19)
<223> OTHER INFORMATION: n is NapdU
<220> FEATURE:
<221> NAME/KEY: misc_feature
<222> LOCATION: (23)..(23)
<223> OTHER INFORMATION: n is NapdU
<220> FEATURE:
<221> NAME/KEY: misc_feature
<222> LOCATION: (26)..(26)
<223> OTHER INFORMATION: n is NapdU
<220> FEATURE:
<221> NAME/KEY: misc_feature
<222> LOCATION: (31)..(31)
<223> OTHER INFORMATION: n is NapdU
<220> FEATURE:
<221> NAME/KEY: misc_feature
<222> LOCATION: (35)..(35)
<223> OTHER INFORMATION: n is NapdU

<400> SEQUENCE: 50
ngagacnnga nnnacgnnna gcngcnaaca ngggnaacca          40

<210> SEQ ID NO 51
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is NapdU
<220> FEATURE:
<221> NAME/KEY: misc_feature
<222> LOCATION: (7)..(8)
<223> OTHER INFORMATION: n is NapdU
<220> FEATURE:
<221> NAME/KEY: misc_feature
<222> LOCATION: (11)..(13)
<223> OTHER INFORMATION: n is NapdU
<220> FEATURE:
<221> NAME/KEY: misc_feature
<222> LOCATION: (17)..(19)
<223> OTHER INFORMATION: n is NapdU
<220> FEATURE:
<221> NAME/KEY: misc_feature
<222> LOCATION: (23)..(23)
<223> OTHER INFORMATION: n is NapdU
<220> FEATURE:
<221> NAME/KEY: misc_feature
<222> LOCATION: (26)..(26)
<223> OTHER INFORMATION: n is NapdU
<220> FEATURE:

<221> NAME/KEY: misc_feature
<222> LOCATION: (31)..(31)
<223> OTHER INFORMATION: n is NapdU

<400> SEQUENCE: 51
ngagacnnga nnnacgnnna gcngcnaaca ngggaaacca                40

<210> SEQ ID NO 52
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is NapdU
<220> FEATURE:
<221> NAME/KEY: misc_feature
<222> LOCATION: (7)..(8)
<223> OTHER INFORMATION: n is NapdU
<220> FEATURE:
<221> NAME/KEY: misc_feature
<222> LOCATION: (11)..(13)
<223> OTHER INFORMATION: n is NapdU
<220> FEATURE:
<221> NAME/KEY: misc_feature
<222> LOCATION: (17)..(19)
<223> OTHER INFORMATION: n is NapdU
<220> FEATURE:
<221> NAME/KEY: misc_feature
<222> LOCATION: (23)..(23)
<223> OTHER INFORMATION: n is NapdU
<220> FEATURE:
<221> NAME/KEY: misc_feature
<222> LOCATION: (26)..(26)
<223> OTHER INFORMATION: n is NapdU
<220> FEATURE:
<221> NAME/KEY: misc_feature
<222> LOCATION: (31)..(31)
<223> OTHER INFORMATION: n is NapdU

<400> SEQUENCE: 52
ngagacnnga nnnacgnnna gcnacnaaca ngggaaccc                39

<210> SEQ ID NO 53
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is NapdU
<220> FEATURE:
<221> NAME/KEY: misc_feature
<222> LOCATION: (7)..(8)
<223> OTHER INFORMATION: n is NapdU
<220> FEATURE:
<221> NAME/KEY: misc_feature
<222> LOCATION: (11)..(13)
<223> OTHER INFORMATION: n is NapdU
<220> FEATURE:
<221> NAME/KEY: misc_feature
<222> LOCATION: (17)..(19)
<223> OTHER INFORMATION: n is NapdU
<220> FEATURE:
<221> NAME/KEY: misc_feature
<222> LOCATION: (23)..(23)
<223> OTHER INFORMATION: n is NapdU
<220> FEATURE:
<221> NAME/KEY: misc_feature
<222> LOCATION: (26)..(26)
<223> OTHER INFORMATION: n is NapdU

```
<220> FEATURE:
<221> NAME/KEY: misc_feature
<222> LOCATION: (31)..(31)
<223> OTHER INFORMATION: n is NapdU

<400> SEQUENCE: 53
ngagacnnga nnnacgnnna gcngcaaaca ngggaaccc                              39

<210> SEQ ID NO 54
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is NapdU
<220> FEATURE:
<221> NAME/KEY: misc_feature
<222> LOCATION: (7)..(8)
<223> OTHER INFORMATION: n is NapdU
<220> FEATURE:
<221> NAME/KEY: misc_feature
<222> LOCATION: (11)..(13)
<223> OTHER INFORMATION: n is NapdU
<220> FEATURE:
<221> NAME/KEY: misc_feature
<222> LOCATION: (17)..(19)
<223> OTHER INFORMATION: n is NapdU
<220> FEATURE:
<221> NAME/KEY: misc_feature
<222> LOCATION: (23)..(23)
<223> OTHER INFORMATION: n is NapdU
<220> FEATURE:
<221> NAME/KEY: misc_feature
<222> LOCATION: (26)..(26)
<223> OTHER INFORMATION: n is NapdU
<220> FEATURE:
<221> NAME/KEY: misc_feature
<222> LOCATION: (31)..(31)
<223> OTHER INFORMATION: n is NapdU

<400> SEQUENCE: 54
ngcgacnnga nnnacgnnna gcngcaaaca ngggaaccc                              39

<210> SEQ ID NO 55
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is NapdU
<220> FEATURE:
<221> NAME/KEY: misc_feature
<222> LOCATION: (7)..(8)
<223> OTHER INFORMATION: n is NapdU
<220> FEATURE:
<221> NAME/KEY: misc_feature
<222> LOCATION: (11)..(13)
<223> OTHER INFORMATION: n is NapdU
<220> FEATURE:
<221> NAME/KEY: misc_feature
<222> LOCATION: (17)..(19)
<223> OTHER INFORMATION: n is NapdU
<220> FEATURE:
<221> NAME/KEY: misc_feature
<222> LOCATION: (23)..(23)
<223> OTHER INFORMATION: n is NapdU
<220> FEATURE:
<221> NAME/KEY: misc_feature
<222> LOCATION: (26)..(26)
```

<223> OTHER INFORMATION: n is NapdU
<220> FEATURE:
<221> NAME/KEY: misc_feature
<222> LOCATION: (31)..(31)
<223> OTHER INFORMATION: n is NapdU

<400> SEQUENCE: 55
ngagacnnga nnnacgnnna gcngcnaaca ngggggaaccc          40

<210> SEQ ID NO 56
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is NapdU
<220> FEATURE:
<221> NAME/KEY: misc_feature
<222> LOCATION: (7)..(8)
<223> OTHER INFORMATION: n is NapdU
<220> FEATURE:
<221> NAME/KEY: misc_feature
<222> LOCATION: (11)..(13)
<223> OTHER INFORMATION: n is NapdU
<220> FEATURE:
<221> NAME/KEY: misc_feature
<222> LOCATION: (17)..(19)
<223> OTHER INFORMATION: n is NapdU
<220> FEATURE:
<221> NAME/KEY: misc_feature
<222> LOCATION: (23)..(23)
<223> OTHER INFORMATION: n is NapdU
<220> FEATURE:
<221> NAME/KEY: misc_feature
<222> LOCATION: (26)..(26)
<223> OTHER INFORMATION: n is NapdU
<220> FEATURE:
<221> NAME/KEY: misc_feature
<222> LOCATION: (31)..(31)
<223> OTHER INFORMATION: n is NapdU
<220> FEATURE:
<221> NAME/KEY: misc_feature
<222> LOCATION: (37)..(37)
<223> OTHER INFORMATION: n is NapdU

<400> SEQUENCE: 56
ngagacnnga nnnacgnnna gcngcnaaca nggggancccc          40

<210> SEQ ID NO 57
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is NapdU
<220> FEATURE:
<221> NAME/KEY: misc_feature
<222> LOCATION: (7)..(8)
<223> OTHER INFORMATION: n is NapdU
<220> FEATURE:
<221> NAME/KEY: misc_feature
<222> LOCATION: (11)..(13)
<223> OTHER INFORMATION: n is NapdU
<220> FEATURE:
<221> NAME/KEY: misc_feature
<222> LOCATION: (17)..(19)
<223> OTHER INFORMATION: n is NapdU
<220> FEATURE:
<221> NAME/KEY: misc_feature

```
<222> LOCATION: (23)..(23)
<223> OTHER INFORMATION: n is NapdU
<220> FEATURE:
<221> NAME/KEY: misc_feature
<222> LOCATION: (26)..(26)
<223> OTHER INFORMATION: n is NapdU
<220> FEATURE:
<221> NAME/KEY: misc_feature
<222> LOCATION: (31)..(31)
<223> OTHER INFORMATION: n is NapdU
<220> FEATURE:
<221> NAME/KEY: misc_feature
<222> LOCATION: (34)..(34)
<223> OTHER INFORMATION: n is NapdU
<220> FEATURE:
<221> NAME/KEY: misc_feature
<222> LOCATION: (39)..(39)
<223> OTHER INFORMATION: n is NapdU

<400> SEQUENCE: 57
ngagacnnga nnnacgnnna gcngcnaaca nggngaacna                           40

<210> SEQ ID NO 58
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is NapdU
<220> FEATURE:
<221> NAME/KEY: misc_feature
<222> LOCATION: (7)..(8)
<223> OTHER INFORMATION: n is NapdU
<220> FEATURE:
<221> NAME/KEY: misc_feature
<222> LOCATION: (11)..(13)
<223> OTHER INFORMATION: n is NapdU
<220> FEATURE:
<221> NAME/KEY: misc_feature
<222> LOCATION: (17)..(19)
<223> OTHER INFORMATION: n is NapdU
<220> FEATURE:
<221> NAME/KEY: misc_feature
<222> LOCATION: (23)..(23)
<223> OTHER INFORMATION: n is NapdU
<220> FEATURE:
<221> NAME/KEY: misc_feature
<222> LOCATION: (26)..(26)
<223> OTHER INFORMATION: n is NapdU
<220> FEATURE:
<221> NAME/KEY: misc_feature
<222> LOCATION: (31)..(31)
<223> OTHER INFORMATION: n is NapdU
<220> FEATURE:
<221> NAME/KEY: misc_feature
<222> LOCATION: (39)..(39)
<223> OTHER INFORMATION: n is NapdU

<400> SEQUENCE: 58
ngagacnnga nnnacgnnna gcngcnaaca ngggaacnc                            40

<210> SEQ ID NO 59
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is NapdU
<220> FEATURE:
```

```
<221> NAME/KEY: misc_feature
<222> LOCATION: (7)..(8)
<223> OTHER INFORMATION: n is NapdU
<220> FEATURE:
<221> NAME/KEY: misc_feature
<222> LOCATION: (11)..(13)
<223> OTHER INFORMATION: n is NapdU
<220> FEATURE:
<221> NAME/KEY: misc_feature
<222> LOCATION: (17)..(19)
<223> OTHER INFORMATION: n is NapdU
<220> FEATURE:
<221> NAME/KEY: misc_feature
<222> LOCATION: (22)..(23)
<223> OTHER INFORMATION: n is NapdU
<220> FEATURE:
<221> NAME/KEY: misc_feature
<222> LOCATION: (26)..(26)
<223> OTHER INFORMATION: n is NapdU
<220> FEATURE:
<221> NAME/KEY: misc_feature
<222> LOCATION: (31)..(31)
<223> OTHER INFORMATION: n is NapdU

<400> SEQUENCE: 59
ngagacnnga nnnacgnnna gnngcnaaca ngggaacca                40

<210> SEQ ID NO 60
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: n is NapdU
<220> FEATURE:
<221> NAME/KEY: misc_feature
<222> LOCATION: (7)..(7)
<223> OTHER INFORMATION: n is NapdU
<220> FEATURE:
<221> NAME/KEY: misc_feature
<222> LOCATION: (13)..(13)
<223> OTHER INFORMATION: n is NapdU
<220> FEATURE:
<221> NAME/KEY: misc_feature
<222> LOCATION: (16)..(18)
<223> OTHER INFORMATION: n is NapdU
<220> FEATURE:
<221> NAME/KEY: misc_feature
<222> LOCATION: (22)..(23)
<223> OTHER INFORMATION: n is NapdU
<220> FEATURE:
<221> NAME/KEY: misc_feature
<222> LOCATION: (29)..(29)
<223> OTHER INFORMATION: n is NapdU
<220> FEATURE:
<221> NAME/KEY: misc_feature
<222> LOCATION: (32)..(32)
<223> OTHER INFORMATION: n is NapdU
<220> FEATURE:
<221> NAME/KEY: misc_feature
<222> LOCATION: (35)..(35)
<223> OTHER INFORMATION: n is NapdU

<400> SEQUENCE: 60
gncgccncgg acngcnnnaa gnnagccgnc cnacnacca                39

<210> SEQ ID NO 61
<211> LENGTH: 50
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (7)..(9)
<223> OTHER INFORMATION: n is NapdU
<220> FEATURE:
<221> NAME/KEY: misc_feature
<222> LOCATION: (15)..(16)
<223> OTHER INFORMATION: n is NapdU
<220> FEATURE:
<221> NAME/KEY: misc_feature
<222> LOCATION: (20)..(22)
<223> OTHER INFORMATION: n is NapdU
<220> FEATURE:
<221> NAME/KEY: misc_feature
<222> LOCATION: (26)..(28)
<223> OTHER INFORMATION: n is NapdU
<220> FEATURE:
<221> NAME/KEY: misc_feature
<222> LOCATION: (33)..(33)
<223> OTHER INFORMATION: n is NapdU
<220> FEATURE:
<221> NAME/KEY: misc_feature
<222> LOCATION: (38)..(39)
<223> OTHER INFORMATION: n is NapdU
<220> FEATURE:
<221> NAME/KEY: misc_feature
<222> LOCATION: (43)..(43)
<223> OTHER INFORMATION: n is NapdU
<220> FEATURE:
<221> NAME/KEY: misc_feature
<222> LOCATION: (47)..(47)
<223> OTHER INFORMATION: n is NapdU
<220> FEATURE:
<221> NAME/KEY: misc_feature
<222> LOCATION: (50)..(50)
<223> OTHER INFORMATION: n is NapdU

<400> SEQUENCE: 61
gccgccnnnc ggacnngacn nnaagnnnac gcncgacnng acnccancan                50

<210> SEQ ID NO 62
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: n is NapdU
<220> FEATURE:
<221> NAME/KEY: misc_feature
<222> LOCATION: (6)..(6)
<223> OTHER INFORMATION: n is NapdU
<220> FEATURE:
<221> NAME/KEY: misc_feature
<222> LOCATION: (10)..(11)
<223> OTHER INFORMATION: n is NapdU
<220> FEATURE:
<221> NAME/KEY: misc_feature
<222> LOCATION: (17)..(17)
<223> OTHER INFORMATION: n is NapdU
<220> FEATURE:
<221> NAME/KEY: misc_feature
<222> LOCATION: (21)..(22)
<223> OTHER INFORMATION: n is NapdU
<220> FEATURE:
<221> NAME/KEY: misc_feature
<222> LOCATION: (25)..(27)
<223> OTHER INFORMATION: n is NapdU
<220> FEATURE:
<221> NAME/KEY: misc_feature
<222> LOCATION: (31)..(33)
<223> OTHER INFORMATION: n is NapdU

<400> SEQUENCE: 62
```

```
gngcanaagn nccgggngac nngannnaag nnnagccccc a            41
```

<210> SEQ ID NO 63
<211> LENGTH: 46
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: n is NapdU
<220> FEATURE:
<221> NAME/KEY: misc_feature
<222> LOCATION: (6)..(7)
<223> OTHER INFORMATION: n is NapdU
<220> FEATURE:
<221> NAME/KEY: misc_feature
<222> LOCATION: (14)..(15)
<223> OTHER INFORMATION: n is NapdU
<220> FEATURE:
<221> NAME/KEY: misc_feature
<222> LOCATION: (19)..(21)
<223> OTHER INFORMATION: n is NapdU
<220> FEATURE:
<221> NAME/KEY: misc_feature
<222> LOCATION: (26)..(28)
<223> OTHER INFORMATION: n is NapdU
<220> FEATURE:
<221> NAME/KEY: misc_feature
<222> LOCATION: (33)..(33)
<223> OTHER INFORMATION: n is NapdU
<220> FEATURE:
<221> NAME/KEY: misc_feature
<222> LOCATION: (37)..(38)
<223> OTHER INFORMATION: n is NapdU
<220> FEATURE:
<221> NAME/KEY: misc_feature
<222> LOCATION: (41)..(41)
<223> OTHER INFORMATION: n is NapdU
<220> FEATURE:
<221> NAME/KEY: misc_feature
<222> LOCATION: (46)..(46)
<223> OTHER INFORMATION: n is NapdU

<400> SEQUENCE: 63

```
gngccnnccg gacnngccnn naacgnnnag ccnagcnngc ncacan       46
```

<210> SEQ ID NO 64
<211> LENGTH: 49
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(8)
<223> OTHER INFORMATION: n is NapdU
<220> FEATURE:
<221> NAME/KEY: misc_feature
<222> LOCATION: (12)..(12)
<223> OTHER INFORMATION: n is NapdU
<220> FEATURE:
<221> NAME/KEY: misc_feature
<222> LOCATION: (15)..(16)
<223> OTHER INFORMATION: n is NapdU
<220> FEATURE:
<221> NAME/KEY: misc_feature
<222> LOCATION: (20)..(22)
<223> OTHER INFORMATION: n is NapdU
<220> FEATURE:
<221> NAME/KEY: misc_feature
<222> LOCATION: (26)..(28)
<223> OTHER INFORMATION: n is NapdU
<220> FEATURE:
<221> NAME/KEY: misc_feature
<222> LOCATION: (30)..(30)
<223> OTHER INFORMATION: n is NapdU
<220> FEATURE:
<221> NAME/KEY: misc_feature
<222> LOCATION: (40)..(41)
<223> OTHER INFORMATION: n is NapdU
<220> FEATURE:
<221> NAME/KEY: misc_feature
<222> LOCATION: (44)..(44)
<223> OTHER INFORMATION: n is NapdU
<220> FEATURE:
<221> NAME/KEY: misc_feature
<222> LOCATION: (49)..(49)
<223> OTHER INFORMATION: n is NapdU

<400> SEQUENCE: 64
gccgccnncg gnacnngacn nnaagnnngn aggccagcgn ngcncacan            49

<210> SEQ ID NO 65
<211> LENGTH: 36
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: n is NapdU
<220> FEATURE:
<221> NAME/KEY: misc_feature
<222> LOCATION: (8)..(9)
<223> OTHER INFORMATION: n is NapdU
<220> FEATURE:
<221> NAME/KEY: misc_feature
<222> LOCATION: (12)..(14)
<223> OTHER INFORMATION: n is NapdU
<220> FEATURE:
<221> NAME/KEY: misc_feature
<222> LOCATION: (18)..(20)
<223> OTHER INFORMATION: n is NapdU
<220> FEATURE:
<221> NAME/KEY: misc_feature
<222> LOCATION: (27)..(28)
<223> OTHER INFORMATION: n is NapdU
<220> FEATURE:
<221> NAME/KEY: misc_feature
<222> LOCATION: (31)..(31)
<223> OTHER INFORMATION: n is NapdU
<220> FEATURE:
<221> NAME/KEY: misc_feature
<222> LOCATION: (34)..(34)
<223> OTHER INFORMATION: n is NapdU
<220> FEATURE:
<221> NAME/KEY: misc_feature
<222> LOCATION: (36)..(36)
<223> OTHER INFORMATION: n is NapdU

<400> SEQUENCE: 65
gngagacnng cnnnaagnnn agccgcnngc ncanan                         36

<210> SEQ ID NO 66
<211> LENGTH: 44
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(7)
<223> OTHER INFORMATION: n is NapdU
<220> FEATURE:
<221> NAME/KEY: misc_feature
<222> LOCATION: (13)..(14)
<223> OTHER INFORMATION: n is NapdU
<220> FEATURE:

```
<221> NAME/KEY: misc_feature
<222> LOCATION: (17)..(19)
<223> OTHER INFORMATION: n is NapdU
<220> FEATURE:
<221> NAME/KEY: misc_feature
<222> LOCATION: (23)..(25)
<223> OTHER INFORMATION: n is NapdU
<220> FEATURE:
<221> NAME/KEY: misc_feature
<222> LOCATION: (32)..(33)
<223> OTHER INFORMATION: n is NapdU
<220> FEATURE:
<221> NAME/KEY: misc_feature
<222> LOCATION: (36)..(36)
<223> OTHER INFORMATION: n is NapdU
<220> FEATURE:
<221> NAME/KEY: misc_feature
<222> LOCATION: (39)..(39)
<223> OTHER INFORMATION: n is NapdU
<220> FEATURE:
<221> NAME/KEY: misc_feature
<222> LOCATION: (41)..(41)
<223> OTHER INFORMATION: n is NapdU

<400> SEQUENCE: 66
gcgccnncgg acnngcnnna agnnnagccg cnngancanc ngca          44

<210> SEQ ID NO 67
<211> LENGTH: 47
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: n is NapdU
<220> FEATURE:
<221> NAME/KEY: misc_feature
<222> LOCATION: (6)..(6)
<223> OTHER INFORMATION: n is NapdU
<220> FEATURE:
<221> NAME/KEY: misc_feature
<222> LOCATION: (13)..(14)
<223> OTHER INFORMATION: n is NapdU
<220> FEATURE:
<221> NAME/KEY: misc_feature
<222> LOCATION: (17)..(19)
<223> OTHER INFORMATION: n is NapdU
<220> FEATURE:
<221> NAME/KEY: misc_feature
<222> LOCATION: (24)..(27)
<223> OTHER INFORMATION: n is NapdU
<220> FEATURE:
<221> NAME/KEY: misc_feature
<222> LOCATION: (34)..(35)
<223> OTHER INFORMATION: n is NapdU
<220> FEATURE:
<221> NAME/KEY: misc_feature
<222> LOCATION: (39)..(39)
<223> OTHER INFORMATION: n is NapdU

<400> SEQUENCE: 67
gncgcnacgg acnngannna acgnnnnagc cgcnnacang ggaacca          47

<210> SEQ ID NO 68
<211> LENGTH: 37
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: n is NapdU
```

```
<220> FEATURE:
<221> NAME/KEY: misc_feature
<222> LOCATION: (4)..(4)
<223> OTHER INFORMATION: n is NapdU
<220> FEATURE:
<221> NAME/KEY: misc_feature
<222> LOCATION: (9)..(10)
<223> OTHER INFORMATION: n is NapdU
<220> FEATURE:
<221> NAME/KEY: misc_feature
<222> LOCATION: (13)..(15)
<223> OTHER INFORMATION: n is NapdU
<220> FEATURE:
<221> NAME/KEY: misc_feature
<222> LOCATION: (19)..(21)
<223> OTHER INFORMATION: n is NapdU
<220> FEATURE:
<221> NAME/KEY: misc_feature
<222> LOCATION: (27)..(27)
<223> OTHER INFORMATION: n is NapdU
<220> FEATURE:
<221> NAME/KEY: misc_feature
<222> LOCATION: (29)..(29)
<223> OTHER INFORMATION: n is NapdU
<220> FEATURE:
<221> NAME/KEY: misc_feature
<222> LOCATION: (32)..(32)
<223> OTHER INFORMATION: n is NapdU
<220> FEATURE:
<221> NAME/KEY: misc_feature
<222> LOCATION: (37)..(37)
<223> OTHER INFORMATION: n is NapdU

<400> SEQUENCE: 68
gngnagacnn gannnacgnn nagccgnang cncacan                                    37

<210> SEQ ID NO 69
<211> LENGTH: 36
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(7)
<223> OTHER INFORMATION: n is NapdU
<220> FEATURE:
<221> NAME/KEY: misc_feature
<222> LOCATION: (13)..(14)
<223> OTHER INFORMATION: n is NapdU
<220> FEATURE:
<221> NAME/KEY: misc_feature
<222> LOCATION: (17)..(18)
<223> OTHER INFORMATION: n is NapdU
<220> FEATURE:
<221> NAME/KEY: misc_feature
<222> LOCATION: (23)..(25)
<223> OTHER INFORMATION: n is NapdU
<220> FEATURE:
<221> NAME/KEY: misc_feature
<222> LOCATION: (32)..(33)
<223> OTHER INFORMATION: n is NapdU
<220> FEATURE:
<221> NAME/KEY: misc_feature
<222> LOCATION: (35)..(36)
<223> OTHER INFORMATION: n is NapdU

<400> SEQUENCE: 69
gcgccnncgg acnngcnnaa agnnnagccg cnngnn                                     36

<210> SEQ ID NO 70
<211> LENGTH: 45
<212> TYPE: DNA
<213> ORGANISM: Artificial Sequence
<220> FEATURE:
```

```
<223> OTHER INFORMATION: Synthetic
<220> FEATURE:
<221> NAME/KEY: misc_feature
<222> LOCATION: (2)..(2)
<223> OTHER INFORMATION: n is NapdU
<220> FEATURE:
<221> NAME/KEY: misc_feature
<222> LOCATION: (7)..(8)
<223> OTHER INFORMATION: n is NapdU
<220> FEATURE:
<221> NAME/KEY: misc_feature
<222> LOCATION: (12)..(12)
<223> OTHER INFORMATION: n is NapdU
<220> FEATURE:
<221> NAME/KEY: misc_feature
<222> LOCATION: (15)..(16)
<223> OTHER INFORMATION: n is NapdU
<220> FEATURE:
<221> NAME/KEY: misc_feature
<222> LOCATION: (19)..(21)
<223> OTHER INFORMATION: n is NapdU
<220> FEATURE:
<221> NAME/KEY: misc_feature
<222> LOCATION: (26)..(28)
<223> OTHER INFORMATION: n is NapdU
<220> FEATURE:
<221> NAME/KEY: misc_feature
<222> LOCATION: (35)..(36)
<223> OTHER INFORMATION: n is NapdU
<220> FEATURE:
<221> NAME/KEY: misc_feature
<222> LOCATION: (40)..(40)
<223> OTHER INFORMATION: n is NapdU
<220> FEATURE:
<221> NAME/KEY: misc_feature
<222> LOCATION: (45)..(45)
<223> OTHER INFORMATION: n is NapdU

<400> SEQUENCE: 70
gncgccnncg gnacnngcnn naccgnnnag ccacnnaacn cacan            45

<210> SEQ ID NO 71
<211> LENGTH: 45
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(9)
<223> OTHER INFORMATION: n is NapdU
<220> FEATURE:
<221> NAME/KEY: misc_feature
<222> LOCATION: (16)..(17)
<223> OTHER INFORMATION: n is NapdU
<220> FEATURE:
<221> NAME/KEY: misc_feature
<222> LOCATION: (21)..(23)
<223> OTHER INFORMATION: n is NapdU
<220> FEATURE:
<221> NAME/KEY: misc_feature
<222> LOCATION: (27)..(29)
<223> OTHER INFORMATION: n is NapdU
<220> FEATURE:
<221> NAME/KEY: misc_feature
<222> LOCATION: (37)..(37)
<223> OTHER INFORMATION: n is NapdU
<220> FEATURE:
<221> NAME/KEY: misc_feature
<222> LOCATION: (40)..(40)
<223> OTHER INFORMATION: n is NapdU
<220> FEATURE:
<221> NAME/KEY: misc_feature
<222> LOCATION: (45)..(45)
<223> OTHER INFORMATION: n is NapdU

<400> SEQUENCE: 71
```

```
gacggccnnc cggacnngac nnnacgnnna gccgccngcn cacan         45
```

<210> SEQ ID NO 72
<211> LENGTH: 44
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: n is NapdU
<220> FEATURE:
<221> NAME/KEY: misc_feature
<222> LOCATION: (5)..(5)
<223> OTHER INFORMATION: n is NapdU
<220> FEATURE:
<221> NAME/KEY: misc_feature
<222> LOCATION: (11)..(12)
<223> OTHER INFORMATION: n is NapdU
<220> FEATURE:
<221> NAME/KEY: misc_feature
<222> LOCATION: (16)..(18)
<223> OTHER INFORMATION: n is NapdU
<220> FEATURE:
<221> NAME/KEY: misc_feature
<222> LOCATION: (23)..(25)
<223> OTHER INFORMATION: n is NapdU
<220> FEATURE:
<221> NAME/KEY: misc_feature
<222> LOCATION: (29)..(29)
<223> OTHER INFORMATION: n is NapdU
<220> FEATURE:
<221> NAME/KEY: misc_feature
<222> LOCATION: (32)..(33)
<223> OTHER INFORMATION: n is NapdU
<220> FEATURE:
<221> NAME/KEY: misc_feature
<222> LOCATION: (37)..(37)
<223> OTHER INFORMATION: n is NapdU
<220> FEATURE:
<221> NAME/KEY: misc_feature
<222> LOCATION: (43)..(43)
<223> OTHER INFORMATION: n is NapdU

<400> SEQUENCE: 72

```
gngcnaggac nngacnnnaa cgnnnagcng cnnacangga acnc          44
```

<210> SEQ ID NO 73
<211> LENGTH: 43
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: n is NapdU
<220> FEATURE:
<221> NAME/KEY: misc_feature
<222> LOCATION: (14)..(15)
<223> OTHER INFORMATION: n is NapdU
<220> FEATURE:
<221> NAME/KEY: misc_feature
<222> LOCATION: (18)..(20)
<223> OTHER INFORMATION: n is NapdU
<220> FEATURE:
<221> NAME/KEY: misc_feature
<222> LOCATION: (24)..(26)
<223> OTHER INFORMATION: n is NapdU
<220> FEATURE:
<221> NAME/KEY: misc_feature
<222> LOCATION: (33)..(33)
<223> OTHER INFORMATION: n is NapdU
<220> FEATURE:

-continued

```
<221> NAME/KEY: misc_feature
<222> LOCATION: (36)..(37)
<223> OTHER INFORMATION: n is NapdU
<220> FEATURE:
<221> NAME/KEY: misc_feature
<222> LOCATION: (42)..(42)
<223> OTHER INFORMATION: n is NapdU

<400> SEQUENCE: 73
gcgccncgga accnngcnnn aagnnnagcc gcngcnncac ana           43

<210> SEQ ID NO 74
<211> LENGTH: 43
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: n is NapdU
<220> FEATURE:
<221> NAME/KEY: misc_feature
<222> LOCATION: (7)..(7)
<223> OTHER INFORMATION: n is NapdU
<220> FEATURE:
<221> NAME/KEY: misc_feature
<222> LOCATION: (13)..(14)
<223> OTHER INFORMATION: n is NapdU
<220> FEATURE:
<221> NAME/KEY: misc_feature
<222> LOCATION: (17)..(19)
<223> OTHER INFORMATION: n is NapdU
<220> FEATURE:
<221> NAME/KEY: misc_feature
<222> LOCATION: (24)..(26)
<223> OTHER INFORMATION: n is NapdU
<220> FEATURE:
<221> NAME/KEY: misc_feature
<222> LOCATION: (31)..(31)
<223> OTHER INFORMATION: n is NapdU
<220> FEATURE:
<221> NAME/KEY: misc_feature
<222> LOCATION: (34)..(34)
<223> OTHER INFORMATION: n is NapdU
<220> FEATURE:
<221> NAME/KEY: misc_feature
<222> LOCATION: (43)..(43)
<223> OTHER INFORMATION: n is NapdU

<400> SEQUENCE: 74
gncgccncgg acnngcnnna agannnagcc ngcngcaaca can           43

<210> SEQ ID NO 75
<211> LENGTH: 43
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: n is NapdU
<220> FEATURE:
<221> NAME/KEY: misc_feature
<222> LOCATION: (13)..(14)
<223> OTHER INFORMATION: n is NapdU
<220> FEATURE:
<221> NAME/KEY: misc_feature
<222> LOCATION: (18)..(20)
<223> OTHER INFORMATION: n is NapdU
<220> FEATURE:
<221> NAME/KEY: misc_feature
<222> LOCATION: (25)..(26)
<223> OTHER INFORMATION: n is NapdU
```

```
<220> FEATURE:
<221> NAME/KEY: misc_feature
<222> LOCATION: (33)..(34)
<223> OTHER INFORMATION: n is NapdU
<220> FEATURE:
<221> NAME/KEY: misc_feature
<222> LOCATION: (37)..(37)
<223> OTHER INFORMATION: n is NapdU
<220> FEATURE:
<221> NAME/KEY: misc_feature
<222> LOCATION: (43)..(43)
<223> OTHER INFORMATION: n is NapdU

<400> SEQUENCE: 75
gcgcnnacgg acnngacnnn aaagnnagcc gcnngcncac can                43

<210> SEQ ID NO 76
<211> LENGTH: 48
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(9)
<223> OTHER INFORMATION: n is NapdU
<220> FEATURE:
<221> NAME/KEY: misc_feature
<222> LOCATION: (15)..(16)
<223> OTHER INFORMATION: n is NapdU
<220> FEATURE:
<221> NAME/KEY: misc_feature
<222> LOCATION: (19)..(21)
<223> OTHER INFORMATION: n is NapdU
<220> FEATURE:
<221> NAME/KEY: misc_feature
<222> LOCATION: (25)..(27)
<223> OTHER INFORMATION: n is NapdU
<220> FEATURE:
<221> NAME/KEY: misc_feature
<222> LOCATION: (34)..(35)
<223> OTHER INFORMATION: n is NapdU
<220> FEATURE:
<221> NAME/KEY: misc_feature
<222> LOCATION: (38)..(38)
<223> OTHER INFORMATION: n is NapdU
<220> FEATURE:
<221> NAME/KEY: misc_feature
<222> LOCATION: (43)..(43)
<223> OTHER INFORMATION: n is NapdU

<400> SEQUENCE: 76
ctgcgccnnc ggacnngcnn naagnnnagc cgcnngcnca cancacaa            48

<210> SEQ ID NO 77
<211> LENGTH: 46
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(7)
<223> OTHER INFORMATION: n is NapdU
<220> FEATURE:
<221> NAME/KEY: misc_feature
<222> LOCATION: (13)..(14)
<223> OTHER INFORMATION: n is NapdU
<220> FEATURE:
<221> NAME/KEY: misc_feature
<222> LOCATION: (17)..(19)
<223> OTHER INFORMATION: n is NapdU
<220> FEATURE:
<221> NAME/KEY: misc_feature
<222> LOCATION: (23)..(25)
```

<223> OTHER INFORMATION: n is NapdU
<220> FEATURE:
<221> NAME/KEY: misc_feature
<222> LOCATION: (32)..(33)
<223> OTHER INFORMATION: n is NapdU
<220> FEATURE:
<221> NAME/KEY: misc_feature
<222> LOCATION: (36)..(36)
<223> OTHER INFORMATION: n is NapdU
<220> FEATURE:
<221> NAME/KEY: misc_feature
<222> LOCATION: (41)..(41)
<223> OTHER INFORMATION: n is NapdU

<400> SEQUENCE: 77
gcgccnncgg acnngcnnna agnnnagccg cnngcncaca ncacaa                 46

<210> SEQ ID NO 78
<211> LENGTH: 44
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: n is NapdU
<220> FEATURE:
<221> NAME/KEY: misc_feature
<222> LOCATION: (11)..(12)
<223> OTHER INFORMATION: n is NapdU
<220> FEATURE:
<221> NAME/KEY: misc_feature
<222> LOCATION: (15)..(17)
<223> OTHER INFORMATION: n is NapdU
<220> FEATURE:
<221> NAME/KEY: misc_feature
<222> LOCATION: (21)..(23)
<223> OTHER INFORMATION: n is NapdU
<220> FEATURE:
<221> NAME/KEY: misc_feature
<222> LOCATION: (30)..(31)
<223> OTHER INFORMATION: n is NapdU
<220> FEATURE:
<221> NAME/KEY: misc_feature
<222> LOCATION: (34)..(34)
<223> OTHER INFORMATION: n is NapdU
<220> FEATURE:
<221> NAME/KEY: misc_feature
<222> LOCATION: (39)..(39)
<223> OTHER INFORMATION: n is NapdU

<400> SEQUENCE: 78
gccnncggac nngcnnnaag nnnagccgcn ngcncacanc acaa                   44

<210> SEQ ID NO 79
<211> LENGTH: 42
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: n is NapdU
<220> FEATURE:
<221> NAME/KEY: misc_feature
<222> LOCATION: (9)..(10)
<223> OTHER INFORMATION: n is NapdU
<220> FEATURE:
<221> NAME/KEY: misc_feature
<222> LOCATION: (13)..(15)
<223> OTHER INFORMATION: n is NapdU
<220> FEATURE:
<221> NAME/KEY: misc_feature

```
<222> LOCATION: (19)..(21)
<223> OTHER INFORMATION: n is NapdU
<220> FEATURE:
<221> NAME/KEY: misc_feature
<222> LOCATION: (28)..(29)
<223> OTHER INFORMATION: n is NapdU
<220> FEATURE:
<221> NAME/KEY: misc_feature
<222> LOCATION: (32)..(32)
<223> OTHER INFORMATION: n is NapdU
<220> FEATURE:
<221> NAME/KEY: misc_feature
<222> LOCATION: (37)..(37)
<223> OTHER INFORMATION: n is NapdU

<400> SEQUENCE: 79
cnncggacnn gcnnaagnn nagccgcnng cncacancac aa                42

<210> SEQ ID NO 80
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is NapdU
<220> FEATURE:
<221> NAME/KEY: misc_feature
<222> LOCATION: (7)..(8)
<223> OTHER INFORMATION: n is NapdU
<220> FEATURE:
<221> NAME/KEY: misc_feature
<222> LOCATION: (11)..(13)
<223> OTHER INFORMATION: n is NapdU
<220> FEATURE:
<221> NAME/KEY: misc_feature
<222> LOCATION: (17)..(19)
<223> OTHER INFORMATION: n is NapdU
<220> FEATURE:
<221> NAME/KEY: misc_feature
<222> LOCATION: (26)..(27)
<223> OTHER INFORMATION: n is NapdU
<220> FEATURE:
<221> NAME/KEY: misc_feature
<222> LOCATION: (30)..(30)
<223> OTHER INFORMATION: n is NapdU
<220> FEATURE:
<221> NAME/KEY: misc_feature
<222> LOCATION: (35)..(35)
<223> OTHER INFORMATION: n is NapdU

<400> SEQUENCE: 80
ncggacnngc nnnaagnnna gccgcnngcn cacancacaa                  40

<210> SEQ ID NO 81
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: n is NapdU
<220> FEATURE:
<221> NAME/KEY: misc_feature
<222> LOCATION: (9)..(11)
<223> OTHER INFORMATION: n is NapdU
<220> FEATURE:
<221> NAME/KEY: misc_feature
<222> LOCATION: (15)..(17)
<223> OTHER INFORMATION: n is NapdU
<220> FEATURE:
```

<220> FEATURE:
<221> NAME/KEY: misc_feature
<222> LOCATION: (24)..(25)
<223> OTHER INFORMATION: n is NapdU
<220> FEATURE:
<221> NAME/KEY: misc_feature
<222> LOCATION: (28)..(28)
<223> OTHER INFORMATION: n is NapdU
<220> FEATURE:
<221> NAME/KEY: misc_feature
<222> LOCATION: (33)..(33)
<223> OTHER INFORMATION: n is NapdU

<400> SEQUENCE: 81
ggacnngcnn naagnnnagc cgcnngcnca cancacaa         38

<210> SEQ ID NO 82
<211> LENGTH: 36
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(4)
<223> OTHER INFORMATION: n is NapdU
<220> FEATURE:
<221> NAME/KEY: misc_feature
<222> LOCATION: (7)..(9)
<223> OTHER INFORMATION: n is NapdU
<220> FEATURE:
<221> NAME/KEY: misc_feature
<222> LOCATION: (13)..(15)
<223> OTHER INFORMATION: n is NapdU
<220> FEATURE:
<221> NAME/KEY: misc_feature
<222> LOCATION: (22)..(23)
<223> OTHER INFORMATION: n is NapdU
<220> FEATURE:
<221> NAME/KEY: misc_feature
<222> LOCATION: (26)..(26)
<223> OTHER INFORMATION: n is NapdU
<220> FEATURE:
<221> NAME/KEY: misc_feature
<222> LOCATION: (31)..(31)
<223> OTHER INFORMATION: n is NapdU

<400> SEQUENCE: 82
acnngcnnna agnnnagccg cnngcncaca ncacaa         36

<210> SEQ ID NO 83
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is NapdU
<220> FEATURE:
<221> NAME/KEY: misc_feature
<222> LOCATION: (5)..(7)
<223> OTHER INFORMATION: n is NapdU
<220> FEATURE:
<221> NAME/KEY: misc_feature
<222> LOCATION: (11)..(13)
<223> OTHER INFORMATION: n is NapdU
<220> FEATURE:
<221> NAME/KEY: misc_feature
<222> LOCATION: (20)..(21)
<223> OTHER INFORMATION: n is NapdU
<220> FEATURE:
<221> NAME/KEY: misc_feature
<222> LOCATION: (24)..(24)
<223> OTHER INFORMATION: n is NapdU

```
<220> FEATURE:
<221> NAME/KEY: misc_feature
<222> LOCATION: (29)..(29)
<223> OTHER INFORMATION: n is NapdU

<400> SEQUENCE: 83
nngcnnnaag nnnagccgcn ngcncacanc acaa                              34

<210> SEQ ID NO 84
<211> LENGTH: 32
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(5)
<223> OTHER INFORMATION: n is NapdU
<220> FEATURE:
<221> NAME/KEY: misc_feature
<222> LOCATION: (9)..(11)
<223> OTHER INFORMATION: n is NapdU
<220> FEATURE:
<221> NAME/KEY: misc_feature
<222> LOCATION: (18)..(19)
<223> OTHER INFORMATION: n is NapdU
<220> FEATURE:
<221> NAME/KEY: misc_feature
<222> LOCATION: (22)..(22)
<223> OTHER INFORMATION: n is NapdU
<220> FEATURE:
<221> NAME/KEY: misc_feature
<222> LOCATION: (27)..(27)
<223> OTHER INFORMATION: n is NapdU

<400> SEQUENCE: 84
gcnnnaagnn nagccgcnng cncacancac aa                                32

<210> SEQ ID NO 85
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: n is NapdU
<220> FEATURE:
<221> NAME/KEY: misc_feature
<222> LOCATION: (7)..(9)
<223> OTHER INFORMATION: n is NapdU
<220> FEATURE:
<221> NAME/KEY: misc_feature
<222> LOCATION: (16)..(17)
<223> OTHER INFORMATION: n is NapdU
<220> FEATURE:
<221> NAME/KEY: misc_feature
<222> LOCATION: (20)..(20)
<223> OTHER INFORMATION: n is NapdU
<220> FEATURE:
<221> NAME/KEY: misc_feature
<222> LOCATION: (25)..(25)
<223> OTHER INFORMATION: n is NapdU

<400> SEQUENCE: 85
nnnaagnnna gccgcnngcn cacancacaa                                   30

<210> SEQ ID NO 86
<211> LENGTH: 48
<212> TYPE: DNA
<213> ORGANISM: Artificial Sequence
<220> FEATURE:
```

```
<223> OTHER INFORMATION: Synthetic
<220> FEATURE:
<221> NAME/KEY: misc_feature
<222> LOCATION: (10)..(11)
<223> OTHER INFORMATION: n is NapdU
<220> FEATURE:
<221> NAME/KEY: misc_feature
<222> LOCATION: (17)..(18)
<223> OTHER INFORMATION: n is NapdU
<220> FEATURE:
<221> NAME/KEY: misc_feature
<222> LOCATION: (21)..(23)
<223> OTHER INFORMATION: n is NapdU
<220> FEATURE:
<221> NAME/KEY: misc_feature
<222> LOCATION: (27)..(29)
<223> OTHER INFORMATION: n is NapdU
<220> FEATURE:
<221> NAME/KEY: misc_feature
<222> LOCATION: (36)..(37)
<223> OTHER INFORMATION: n is NapdU
<220> FEATURE:
<221> NAME/KEY: misc_feature
<222> LOCATION: (40)..(40)
<223> OTHER INFORMATION: n is NapdU
<220> FEATURE:
<221> NAME/KEY: misc_feature
<222> LOCATION: (45)..(45)
<223> OTHER INFORMATION: n is NapdU

<400> SEQUENCE: 86
ccctgcgccn ncggacnngc nnnaagnnna gccgcnngcn cacancac         48

<210> SEQ ID NO 87
<211> LENGTH: 46
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(11)
<223> OTHER INFORMATION: n is NapdU
<220> FEATURE:
<221> NAME/KEY: misc_feature
<222> LOCATION: (17)..(18)
<223> OTHER INFORMATION: n is NapdU
<220> FEATURE:
<221> NAME/KEY: misc_feature
<222> LOCATION: (21)..(23)
<223> OTHER INFORMATION: n is NapdU
<220> FEATURE:
<221> NAME/KEY: misc_feature
<222> LOCATION: (27)..(29)
<223> OTHER INFORMATION: n is NapdU
<220> FEATURE:
<221> NAME/KEY: misc_feature
<222> LOCATION: (36)..(37)
<223> OTHER INFORMATION: n is NapdU
<220> FEATURE:
<221> NAME/KEY: misc_feature
<222> LOCATION: (40)..(40)
<223> OTHER INFORMATION: n is NapdU
<220> FEATURE:
<221> NAME/KEY: misc_feature
<222> LOCATION: (45)..(45)
<223> OTHER INFORMATION: n is NapdU

<400> SEQUENCE: 87
ccctgcgccn ncggacnngc nnnaagnnna gccgcnngcn cacanc           46

<210> SEQ ID NO 88
<211> LENGTH: 44
<212> TYPE: DNA
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (10)..(11)
<223> OTHER INFORMATION: n is NapdU
<220> FEATURE:
<221> NAME/KEY: misc_feature
<222> LOCATION: (17)..(18)
<223> OTHER INFORMATION: n is NapdU
<220> FEATURE:
<221> NAME/KEY: misc_feature
<222> LOCATION: (21)..(23)
<223> OTHER INFORMATION: n is NapdU
<220> FEATURE:
<221> NAME/KEY: misc_feature
<222> LOCATION: (27)..(29)
<223> OTHER INFORMATION: n is NapdU
<220> FEATURE:
<221> NAME/KEY: misc_feature
<222> LOCATION: (36)..(37)
<223> OTHER INFORMATION: n is NapdU
<220> FEATURE:
<221> NAME/KEY: misc_feature
<222> LOCATION: (40)..(40)
<223> OTHER INFORMATION: n is NapdU

<400> SEQUENCE: 88
ccctgcgccn ncggacnngc nnnaagnnna gccgcnngcn caca          44

<210> SEQ ID NO 89
<211> LENGTH: 42
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(11)
<223> OTHER INFORMATION: n is NapdU
<220> FEATURE:
<221> NAME/KEY: misc_feature
<222> LOCATION: (17)..(18)
<223> OTHER INFORMATION: n is NapdU
<220> FEATURE:
<221> NAME/KEY: misc_feature
<222> LOCATION: (21)..(23)
<223> OTHER INFORMATION: n is NapdU
<220> FEATURE:
<221> NAME/KEY: misc_feature
<222> LOCATION: (27)..(29)
<223> OTHER INFORMATION: n is NapdU
<220> FEATURE:
<221> NAME/KEY: misc_feature
<222> LOCATION: (36)..(37)
<223> OTHER INFORMATION: n is NapdU
<220> FEATURE:
<221> NAME/KEY: misc_feature
<222> LOCATION: (40)..(40)
<223> OTHER INFORMATION: n is NapdU

<400> SEQUENCE: 89
ccctgcgccn ncggacnngc nnnaagnnna gccgcnngcn ca            42

<210> SEQ ID NO 90
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(11)
<223> OTHER INFORMATION: n is NapdU
<220> FEATURE:
```

```
<221> NAME/KEY: misc_feature
<222> LOCATION: (17)..(18)
<223> OTHER INFORMATION: n is NapdU
<220> FEATURE:
<221> NAME/KEY: misc_feature
<222> LOCATION: (21)..(23)
<223> OTHER INFORMATION: n is NapdU
<220> FEATURE:
<221> NAME/KEY: misc_feature
<222> LOCATION: (27)..(29)
<223> OTHER INFORMATION: n is NapdU
<220> FEATURE:
<221> NAME/KEY: misc_feature
<222> LOCATION: (36)..(37)
<223> OTHER INFORMATION: n is NapdU
<220> FEATURE:
<221> NAME/KEY: misc_feature
<222> LOCATION: (40)..(40)
<223> OTHER INFORMATION: n is NapdU

<400> SEQUENCE: 90
ccctgcgccn ncggacnngc nnnaagnnna gccgcnngcn                40

<210> SEQ ID NO 91
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(11)
<223> OTHER INFORMATION: n is NapdU
<220> FEATURE:
<221> NAME/KEY: misc_feature
<222> LOCATION: (17)..(18)
<223> OTHER INFORMATION: n is NapdU
<220> FEATURE:
<221> NAME/KEY: misc_feature
<222> LOCATION: (21)..(23)
<223> OTHER INFORMATION: n is NapdU
<220> FEATURE:
<221> NAME/KEY: misc_feature
<222> LOCATION: (27)..(29)
<223> OTHER INFORMATION: n is NapdU
<220> FEATURE:
<221> NAME/KEY: misc_feature
<222> LOCATION: (36)..(37)
<223> OTHER INFORMATION: n is NapdU

<400> SEQUENCE: 91
ccctgcgccn ncggacnngc nnnaagnnna gccgcnng                 38

<210> SEQ ID NO 92
<211> LENGTH: 36
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(11)
<223> OTHER INFORMATION: n is NapdU
<220> FEATURE:
<221> NAME/KEY: misc_feature
<222> LOCATION: (17)..(18)
<223> OTHER INFORMATION: n is NapdU
<220> FEATURE:
<221> NAME/KEY: misc_feature
<222> LOCATION: (21)..(23)
<223> OTHER INFORMATION: n is NapdU
<220> FEATURE:
<221> NAME/KEY: misc_feature
<222> LOCATION: (27)..(29)
<223> OTHER INFORMATION: n is NapdU
```

```
<220> FEATURE:
<221> NAME/KEY: misc_feature
<222> LOCATION: (36)..(36)
<223> OTHER INFORMATION: n is NapdU

<400> SEQUENCE: 92
ccctgcgccn ncggacnngc nnnaagnnna gccgcn                                   36

<210> SEQ ID NO 93
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(11)
<223> OTHER INFORMATION: n is NapdU
<220> FEATURE:
<221> NAME/KEY: misc_feature
<222> LOCATION: (17)..(18)
<223> OTHER INFORMATION: n is NapdU
<220> FEATURE:
<221> NAME/KEY: misc_feature
<222> LOCATION: (21)..(23)
<223> OTHER INFORMATION: n is NapdU
<220> FEATURE:
<221> NAME/KEY: misc_feature
<222> LOCATION: (27)..(29)
<223> OTHER INFORMATION: n is NapdU

<400> SEQUENCE: 93
ccctgcgccn ncggacnngc nnnaagnnna gccg                                     34

<210> SEQ ID NO 94
<211> LENGTH: 32
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(11)
<223> OTHER INFORMATION: n is NapdU
<220> FEATURE:
<221> NAME/KEY: misc_feature
<222> LOCATION: (17)..(18)
<223> OTHER INFORMATION: n is NapdU
<220> FEATURE:
<221> NAME/KEY: misc_feature
<222> LOCATION: (21)..(23)
<223> OTHER INFORMATION: n is NapdU
<220> FEATURE:
<221> NAME/KEY: misc_feature
<222> LOCATION: (27)..(29)
<223> OTHER INFORMATION: n is NapdU

<400> SEQUENCE: 94
ccctgcgccn ncggacnngc nnnaagnnna gc                                       32

<210> SEQ ID NO 95
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(11)
<223> OTHER INFORMATION: n is NapdU
<220> FEATURE:
<221> NAME/KEY: misc_feature
<222> LOCATION: (17)..(18)
```

```
<223> OTHER INFORMATION: n is NapdU
<220> FEATURE:
<221> NAME/KEY: misc_feature
<222> LOCATION: (21)..(23)
<223> OTHER INFORMATION: n is NapdU
<220> FEATURE:
<221> NAME/KEY: misc_feature
<222> LOCATION: (27)..(29)
<223> OTHER INFORMATION: n is NapdU

<400> SEQUENCE: 95
ccctgcgccn ncggacnngc nnnaagnnna                                          30

<210> SEQ ID NO 96
<211> LENGTH: 37
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: n is NapdU
<220> FEATURE:
<221> NAME/KEY: misc_feature
<222> LOCATION: (8)..(10)
<223> OTHER INFORMATION: n is NapdU
<220> FEATURE:
<221> NAME/KEY: misc_feature
<222> LOCATION: (14)..(16)
<223> OTHER INFORMATION: n is NapdU
<220> FEATURE:
<221> NAME/KEY: misc_feature
<222> LOCATION: (23)..(24)
<223> OTHER INFORMATION: n is NapdU
<220> FEATURE:
<221> NAME/KEY: misc_feature
<222> LOCATION: (27)..(27)
<223> OTHER INFORMATION: n is NapdU
<220> FEATURE:
<221> NAME/KEY: misc_feature
<222> LOCATION: (32)..(32)
<223> OTHER INFORMATION: n is NapdU

<400> SEQUENCE: 96
gacnngcnnn aagnnnagcc gcnngcncac ancacaa                                  37

<210> SEQ ID NO 97
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(11)
<223> OTHER INFORMATION: n is NapdU
<220> FEATURE:
<221> NAME/KEY: misc_feature
<222> LOCATION: (17)..(18)
<223> OTHER INFORMATION: n is NapdU
<220> FEATURE:
<221> NAME/KEY: misc_feature
<222> LOCATION: (21)..(23)
<223> OTHER INFORMATION: n is NapdU
<220> FEATURE:
<221> NAME/KEY: misc_feature
<222> LOCATION: (27)..(29)
<223> OTHER INFORMATION: n is NapdU

<400> SEQUENCE: 97
ccctgcgccn ncggacnngc nnnaagnnna gcc                                      33
```

```
<210> SEQ ID NO 98
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: n is NapdU
<220> FEATURE:
<221> NAME/KEY: misc_feature
<222> LOCATION: (9)..(10)
<223> OTHER INFORMATION: n is NapdU
<220> FEATURE:
<221> NAME/KEY: misc_feature
<222> LOCATION: (13)..(15)
<223> OTHER INFORMATION: n is NapdU
<220> FEATURE:
<221> NAME/KEY: misc_feature
<222> LOCATION: (19)..(21)
<223> OTHER INFORMATION: n is NapdU

<400> SEQUENCE: 98
cnncggacnn gcnnnaagnn nagccg                                        26

<210> SEQ ID NO 99
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is NapdU
<220> FEATURE:
<221> NAME/KEY: misc_feature
<222> LOCATION: (7)..(8)
<223> OTHER INFORMATION: n is NapdU
<220> FEATURE:
<221> NAME/KEY: misc_feature
<222> LOCATION: (11)..(13)
<223> OTHER INFORMATION: n is NapdU
<220> FEATURE:
<221> NAME/KEY: misc_feature
<222> LOCATION: (17)..(19)
<223> OTHER INFORMATION: n is NapdU

<400> SEQUENCE: 99
ncggacnngc nnnaagnnna gccg                                          24

<210> SEQ ID NO 100
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: n is NapdU
<220> FEATURE:
<221> NAME/KEY: misc_feature
<222> LOCATION: (9)..(11)
<223> OTHER INFORMATION: n is NapdU
<220> FEATURE:
<221> NAME/KEY: misc_feature
<222> LOCATION: (15)..(17)
<223> OTHER INFORMATION: n is NapdU

<400> SEQUENCE: 100
ggacnngcnn naagnnnagc cg                                            22
```

<210> SEQ ID NO 101
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: n is NapdU
<220> FEATURE:
<221> NAME/KEY: misc_feature
<222> LOCATION: (9)..(11)
<223> OTHER INFORMATION: n is NapdU
<220> FEATURE:
<221> NAME/KEY: misc_feature
<222> LOCATION: (15)..(17)
<223> OTHER INFORMATION: n is NapdU
<220> FEATURE:
<221> NAME/KEY: misc_feature
<222> LOCATION: (24)..(25)
<223> OTHER INFORMATION: n is NapdU

<400> SEQUENCE: 101
ggacnngcnn naagnnnagc cgcnng                                      26

<210> SEQ ID NO 102
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: n is NapdU
<220> FEATURE:
<221> NAME/KEY: misc_feature
<222> LOCATION: (9)..(11)
<223> OTHER INFORMATION: n is NapdU
<220> FEATURE:
<221> NAME/KEY: misc_feature
<222> LOCATION: (15)..(17)
<223> OTHER INFORMATION: n is NapdU
<220> FEATURE:
<221> NAME/KEY: misc_feature
<222> LOCATION: (24)..(25)
<223> OTHER INFORMATION: n is NapdU
<220> FEATURE:
<221> NAME/KEY: misc_feature
<222> LOCATION: (28)..(28)
<223> OTHER INFORMATION: n is NapdU

<400> SEQUENCE: 102
ggacnngcnn naagnnnagc cgcnngcnca                                  30

<210> SEQ ID NO 103
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: n is NapdU
<220> FEATURE:
<221> NAME/KEY: misc_feature
<222> LOCATION: (9)..(11)
<223> OTHER INFORMATION: n is NapdU
<220> FEATURE:
<221> NAME/KEY: misc_feature
<222> LOCATION: (15)..(17)
<223> OTHER INFORMATION: n is NapdU

```
<220> FEATURE:
<221> NAME/KEY: misc_feature
<222> LOCATION: (24)..(24)
<223> OTHER INFORMATION: n is NapdU

<400> SEQUENCE: 103
ggacnngcnn naagnnnagc cgcn                                                 24

<210> SEQ ID NO 104
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: n is NapdU
<220> FEATURE:
<221> NAME/KEY: misc_feature
<222> LOCATION: (8)..(10)
<223> OTHER INFORMATION: n is NapdU
<220> FEATURE:
<221> NAME/KEY: misc_feature
<222> LOCATION: (14)..(16)
<223> OTHER INFORMATION: n is NapdU

<400> SEQUENCE: 104
gacnngcnnn aagnnnagcc g                                                    21

<210> SEQ ID NO 105
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: n is NapdU
<220> FEATURE:
<221> NAME/KEY: misc_feature
<222> LOCATION: (6)..(8)
<223> OTHER INFORMATION: n is NapdU
<220> FEATURE:
<221> NAME/KEY: misc_feature
<222> LOCATION: (10)..(10)
<223> OTHER INFORMATION: n is NapdU
<220> FEATURE:
<221> NAME/KEY: misc_feature
<222> LOCATION: (12)..(14)
<223> OTHER INFORMATION: n is NapdU

<400> SEQUENCE: 105
cnngcnnnan gnnnagc                                                         17

<210> SEQ ID NO 106
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: n is NapdU
<220> FEATURE:
<221> NAME/KEY: misc_feature
<222> LOCATION: (8)..(10)
<223> OTHER INFORMATION: n is NapdU
<220> FEATURE:
<221> NAME/KEY: misc_feature
<222> LOCATION: (14)..(16)
```

<223> OTHER INFORMATION: n is NapdU

<400> SEQUENCE: 106
gacnngannn acgnnnagc                                           19

<210> SEQ ID NO 107
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: n is NapdU
<220> FEATURE:
<221> NAME/KEY: misc_feature
<222> LOCATION: (8)..(10)
<223> OTHER INFORMATION: n is NapdU
<220> FEATURE:
<221> NAME/KEY: misc_feature
<222> LOCATION: (14)..(16)
<223> OTHER INFORMATION: n is NapdU

<400> SEQUENCE: 107
gacnngannn aagnnnagc                                           19

<210> SEQ ID NO 108
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: n is NapdU
<220> FEATURE:
<221> NAME/KEY: misc_feature
<222> LOCATION: (8)..(10)
<223> OTHER INFORMATION: n is NapdU
<220> FEATURE:
<221> NAME/KEY: misc_feature
<222> LOCATION: (14)..(16)
<223> OTHER INFORMATION: n is NapdU

<400> SEQUENCE: 108
gacnngcnnn aagnnnagc                                           19

<210> SEQ ID NO 109
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: n is NapdU
<220> FEATURE:
<221> NAME/KEY: misc_feature
<222> LOCATION: (8)..(10)
<223> OTHER INFORMATION: n is NapdU
<220> FEATURE:
<221> NAME/KEY: misc_feature
<222> LOCATION: (14)..(16)
<223> OTHER INFORMATION: n is NapdU

<400> SEQUENCE: 109
gacnngcnnn acgnnnagc                                           19

```
<210> SEQ ID NO 110
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: may or may not be present
<220> FEATURE:
<221> NAME/KEY: misc_feature
<222> LOCATION: (4)..(4)
<223> OTHER INFORMATION: may or may not be present
<220> FEATURE:
<221> NAME/KEY: misc_feature
<222> LOCATION: (6)..(7)
<223> OTHER INFORMATION: n is a C-5 modified pyrimidine
<220> FEATURE:
<221> NAME/KEY: misc_feature
<222> LOCATION: (9)..(9)
<223> OTHER INFORMATION: may or may not be present
<220> FEATURE:
<221> NAME/KEY: misc_feature
<222> LOCATION: (11)..(13)
<223> OTHER INFORMATION: n is a C-5 modified pyrimidine
<220> FEATURE:
<221> NAME/KEY: misc_feature
<222> LOCATION: (14)..(14)
<223> OTHER INFORMATION: may or may not be present
<220> FEATURE:
<221> NAME/KEY: misc_feature
<222> LOCATION: (16)..(16)
<223> OTHER INFORMATION: may or may not be present
<220> FEATURE:
<221> NAME/KEY: misc_feature
<222> LOCATION: (18)..(18)
<223> OTHER INFORMATION: may or may not be present
<220> FEATURE:
<221> NAME/KEY: misc_feature
<222> LOCATION: (20)..(20)
<223> OTHER INFORMATION: may or may not be present
<220> FEATURE:
<221> NAME/KEY: misc_feature
<222> LOCATION: (21)..(22)
<223> OTHER INFORMATION: n is a C-5 modified pyrimidine
<220> FEATURE:
<221> NAME/KEY: misc_feature
<222> LOCATION: (23)..(23)
<223> OTHER INFORMATION: may or may not be present
<220> FEATURE:
<221> NAME/KEY: misc_feature
<222> LOCATION: (24)..(24)
<223> OTHER INFORMATION: n is a C-5 modified pyrimidine
<220> FEATURE:
<221> NAME/KEY: misc_feature
<222> LOCATION: (26)..(26)
<223> OTHER INFORMATION: may or may not be present

<400> SEQUENCE: 110
rwmccnngmm nnnaacmcrw nngnasgc                                          28

<210> SEQ ID NO 111
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: may or may not be present
<220> FEATURE:
<221> NAME/KEY: misc_feature
<222> LOCATION: (4)..(4)
<223> OTHER INFORMATION: may or may not be present
<220> FEATURE:
```

<221> NAME/KEY: misc_feature
<222> LOCATION: (6)..(7)
<223> OTHER INFORMATION: n is a C-5 modified pyrimidine
<220> FEATURE:
<221> NAME/KEY: misc_feature
<222> LOCATION: (9)..(9)
<223> OTHER INFORMATION: may or may not be present
<220> FEATURE:
<221> NAME/KEY: misc_feature
<222> LOCATION: (11)..(13)
<223> OTHER INFORMATION: n is a C-5 modified pyrimidine
<220> FEATURE:
<221> NAME/KEY: misc_feature
<222> LOCATION: (14)..(14)
<223> OTHER INFORMATION: may or may not be present
<220> FEATURE:
<221> NAME/KEY: misc_feature
<222> LOCATION: (16)..(16)
<223> OTHER INFORMATION: may or may not be present
<220> FEATURE:
<221> NAME/KEY: misc_feature
<222> LOCATION: (18)..(18)
<223> OTHER INFORMATION: may or may not be present
<220> FEATURE:
<221> NAME/KEY: misc_feature
<222> LOCATION: (20)..(20)
<223> OTHER INFORMATION: may or may not be present
<220> FEATURE:
<221> NAME/KEY: misc_feature
<222> LOCATION: (21)..(22)
<223> OTHER INFORMATION: n is a C-5 modified pyrimidine
<220> FEATURE:
<221> NAME/KEY: misc_feature
<222> LOCATION: (23)..(23)
<223> OTHER INFORMATION: may or may not be present
<220> FEATURE:
<221> NAME/KEY: misc_feature
<222> LOCATION: (24)..(24)
<223> OTHER INFORMATION: n is a C-5 modified pyrimidine
<220> FEATURE:
<221> NAME/KEY: misc_feature
<222> LOCATION: (26)..(26)
<223> OTHER INFORMATION: may or may not be present

<400> SEQUENCE: 111
rwaccnngmm nnnaacmcrw nngnasgc                                              28

<210> SEQ ID NO 112
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: may or may not be present
<220> FEATURE:
<221> NAME/KEY: misc_feature
<222> LOCATION: (4)..(4)
<223> OTHER INFORMATION: may or may not be present
<220> FEATURE:
<221> NAME/KEY: misc_feature
<222> LOCATION: (6)..(7)
<223> OTHER INFORMATION: n is a C-5 modified pyrimidine
<220> FEATURE:
<221> NAME/KEY: misc_feature
<222> LOCATION: (9)..(9)
<223> OTHER INFORMATION: may or may not be present
<220> FEATURE:
<221> NAME/KEY: misc_feature
<222> LOCATION: (11)..(13)
<223> OTHER INFORMATION: n is a C-5 modified pyrimidine
<220> FEATURE:
<221> NAME/KEY: misc_feature
<222> LOCATION: (14)..(14)
<223> OTHER INFORMATION: may or may not be present

```
<220> FEATURE:
<221> NAME/KEY: misc_feature
<222> LOCATION: (16)..(16)
<223> OTHER INFORMATION: may or may not be present
<220> FEATURE:
<221> NAME/KEY: misc_feature
<222> LOCATION: (18)..(18)
<223> OTHER INFORMATION: may or may not be present
<220> FEATURE:
<221> NAME/KEY: misc_feature
<222> LOCATION: (20)..(20)
<223> OTHER INFORMATION: may or may not be present
<220> FEATURE:
<221> NAME/KEY: misc_feature
<222> LOCATION: (21)..(22)
<223> OTHER INFORMATION: n is a C-5 modified pyrimidine
<220> FEATURE:
<221> NAME/KEY: misc_feature
<222> LOCATION: (23)..(23)
<223> OTHER INFORMATION: may or may not be present
<220> FEATURE:
<221> NAME/KEY: misc_feature
<222> LOCATION: (24)..(24)
<223> OTHER INFORMATION: n is a C-5 modified pyrimidine
<220> FEATURE:
<221> NAME/KEY: misc_feature
<222> LOCATION: (26)..(26)
<223> OTHER INFORMATION: may or may not be present

<400> SEQUENCE: 112
rwmccnngmm nnnaacmcgw nngnasgc                                           28

<210> SEQ ID NO 113
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: n is a C-5 modified pyrimidine
<220> FEATURE:
<221> NAME/KEY: misc_feature
<222> LOCATION: (7)..(7)
<223> OTHER INFORMATION: may or may not be present
<220> FEATURE:
<221> NAME/KEY: misc_feature
<222> LOCATION: (9)..(11)
<223> OTHER INFORMATION: n is a C-5 modified pyrimidine
<220> FEATURE:
<221> NAME/KEY: misc_feature
<222> LOCATION: (12)..(12)
<223> OTHER INFORMATION: may or may not be present
<220> FEATURE:
<221> NAME/KEY: misc_feature
<222> LOCATION: (14)..(14)
<223> OTHER INFORMATION: may or may not be present
<220> FEATURE:
<221> NAME/KEY: misc_feature
<222> LOCATION: (16)..(16)
<223> OTHER INFORMATION: may or may not be present
<220> FEATURE:
<221> NAME/KEY: misc_feature
<222> LOCATION: (18)..(18)
<223> OTHER INFORMATION: may or may not be present
<220> FEATURE:
<221> NAME/KEY: misc_feature
<222> LOCATION: (19)..(21)
<223> OTHER INFORMATION: n is a C-5 modified pyrimidine
<220> FEATURE:
<221> NAME/KEY: misc_feature
<222> LOCATION: (23)..(23)
<223> OTHER INFORMATION: may or may not be present

<400> SEQUENCE: 113
```
rmcnngmmnn naacmcrwnn nasgc                                              25

<210> SEQ ID NO 114
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: n is a C-5 modified pyrimidine
<220> FEATURE:
<221> NAME/KEY: misc_feature
<222> LOCATION: (6)..(8)
<223> OTHER INFORMATION: n is a C-5 modified pyrimidine

<400> SEQUENCE: 114 cnngmnnn                                                                  8

<210> SEQ ID NO 115
<211> LENGTH: 6
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: n is a C-5 modified pyrimidine

<400> SEQUENCE: 115 nnnagc                                                                    6

<210> SEQ ID NO 116
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: n is a C-5 modified pyrimidine
<220> FEATURE:
<221> NAME/KEY: misc_feature
<222> LOCATION: (6)..(8)
<223> OTHER INFORMATION: n is a C-5 modified pyrimidine
<220> FEATURE:
<221> NAME/KEY: misc_feature
<222> LOCATION: (9)..(13)
<223> OTHER INFORMATION: n, if present, is a, c, g, t, or u; up to 3
      nucleotides may be absent
<220> FEATURE:
<221> NAME/KEY: misc_feature
<222> LOCATION: (14)..(16)
<223> OTHER INFORMATION: n is a C-5 modified pyrimidine

<400> SEQUENCE: 116 cnngmnnnn nnnnnnagc                                                      19

<210> SEQ ID NO 117
<211> LENGTH: 45
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: n is NapdU
<220> FEATURE:

```
<221> NAME/KEY: misc_feature
<222> LOCATION: (11)..(11)
<223> OTHER INFORMATION: n is NapdU
<220> FEATURE:
<221> NAME/KEY: misc_feature
<222> LOCATION: (15)..(16)
<223> OTHER INFORMATION: n is NapdU
<220> FEATURE:
<221> NAME/KEY: misc_feature
<222> LOCATION: (19)..(21)
<223> OTHER INFORMATION: n is NapdU
<220> FEATURE:
<221> NAME/KEY: misc_feature
<222> LOCATION: (25)..(27)
<223> OTHER INFORMATION: n is NapdU
<220> FEATURE:
<221> NAME/KEY: misc_feature
<222> LOCATION: (32)..(32)
<223> OTHER INFORMATION: n is NapdU

<400> SEQUENCE: 117
ctgtgcgnac ngacnngann nacgnnnagc gngccgaggc cacaa          45

<210> SEQ ID NO 118
<211> LENGTH: 108
<212> TYPE: PRT
<213> ORGANISM: Homo sapiens
<220> FEATURE:
<221> NAME/KEY: misc_feature
<223> OTHER INFORMATION: exemplary mature human GDF11 protein

<400> SEQUENCE: 118
```

Leu Gly Leu Asp Cys Asp Glu His Ser Glu Ser Arg Cys Cys Arg
1               5                   10                  15

Tyr Pro Leu Thr Val Asp Phe Glu Ala Phe Gly Trp Asp Trp Ile Ile
            20                  25                  30

Ala Pro Lys Arg Tyr Lys Ala Asn Tyr Cys Ser Gly Gln Cys Glu Tyr
        35                  40                  45

Met Phe Met Gln Lys Tyr Pro His Thr His Leu Val Gln Gln Ala Asn
    50                  55                  60

Pro Arg Gly Ser Ala Gly Pro Cys Cys Thr Pro Thr Lys Met Ser Pro
65                  70                  75                  80

Ile Asn Met Leu Tyr Phe Asn Asp Lys Gln Gln Ile Ile Tyr Gly Lys
                85                  90                  95

Ile Pro Gly Met Val Val Asp Arg Cys Gly Cys Ser
            100                 105

```
<210> SEQ ID NO 119
<211> LENGTH: 108
<212> TYPE: PRT
<213> ORGANISM: Homo sapiens
<220> FEATURE:
<221> NAME/KEY: misc_feature
<223> OTHER INFORMATION: exemplary mature human GDF8 protein

<400> SEQUENCE: 119
```

Phe Gly Leu Asp Cys Asp Glu His Ser Thr Glu Ser Arg Cys Cys Arg
1               5                   10                  15

Tyr Pro Leu Thr Val Asp Phe Glu Ala Phe Gly Trp Asp Trp Ile Ile
            20                  25                  30

Ala Pro Lys Arg Tyr Lys Ala Asn Tyr Cys Ser Gly Glu Cys Glu Phe
        35                  40                  45

Val Phe Leu Gln Lys Tyr Pro His Thr His Leu Val His Gln Ala Asn
    50                  55                  60

```
Pro Arg Gly Ser Ala Gly Pro Cys Cys Thr Pro Thr Lys Met Ser Pro
 65                  70                  75                  80

Ile Asn Met Leu Tyr Phe Asn Gly Lys Glu Gln Ile Ile Tyr Gly Lys
                 85                  90                  95

Ile Pro Ala Met Val Val Asp Arg Cys Gly Cys Ser
            100                 105
```

```
<210> SEQ ID NO 120
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: n is NapdU
<220> FEATURE:
<221> NAME/KEY: misc_feature
<222> LOCATION: (11)..(11)
<223> OTHER INFORMATION: n is NapdU
<220> FEATURE:
<221> NAME/KEY: misc_feature
<222> LOCATION: (13)..(13)
<223> OTHER INFORMATION: n is NapdU
<220> FEATURE:
<221> NAME/KEY: misc_feature
<222> LOCATION: (24)..(25)
<223> OTHER INFORMATION: n is NapdU
<220> FEATURE:
<221> NAME/KEY: misc_feature
<222> LOCATION: (28)..(30)
<223> OTHER INFORMATION: n is NapdU
<220> FEATURE:
<221> NAME/KEY: misc_feature
<222> LOCATION: (34)..(36)
<223> OTHER INFORMATION: n is NapdU
<220> FEATURE:
<221> NAME/KEY: misc_feature
<222> LOCATION: (44)..(44)
<223> OTHER INFORMATION: n is NapdU

<400> SEQUENCE: 120
ctgtgacnaa ngngaccgga gacnngcnnn acgnnnagcg accngcacaa            50
```

```
<210> SEQ ID NO 121
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: n is NapdU
<220> FEATURE:
<221> NAME/KEY: misc_feature
<222> LOCATION: (12)..(12)
<223> OTHER INFORMATION: n is NapdU
<220> FEATURE:
<221> NAME/KEY: misc_feature
<222> LOCATION: (17)..(18)
<223> OTHER INFORMATION: n is NapdU
<220> FEATURE:
<221> NAME/KEY: misc_feature
<222> LOCATION: (21)..(23)
<223> OTHER INFORMATION: n is NapdU
<220> FEATURE:
<221> NAME/KEY: misc_feature
<222> LOCATION: (27)..(29)
<223> OTHER INFORMATION: n is NapdU
<220> FEATURE:
<221> NAME/KEY: misc_feature
<222> LOCATION: (34)..(34)
```

<223> OTHER INFORMATION: n is NapdU
<220> FEATURE:
<221> NAME/KEY: misc_feature
<222> LOCATION: (45)..(45)
<223> OTHER INFORMATION: n is NapdU

<400> SEQUENCE: 121
ctgtgangcc gnggacnngc nnnacgnnna gccncgcggg gagcncacaa            50

<210> SEQ ID NO 122
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: n is NapdU
<220> FEATURE:
<221> NAME/KEY: misc_feature
<222> LOCATION: (22)..(23)
<223> OTHER INFORMATION: n is NapdU
<220> FEATURE:
<221> NAME/KEY: misc_feature
<222> LOCATION: (26)..(28)
<223> OTHER INFORMATION: n is NapdU
<220> FEATURE:
<221> NAME/KEY: misc_feature
<222> LOCATION: (32)..(34)
<223> OTHER INFORMATION: n is NapdU
<220> FEATURE:
<221> NAME/KEY: misc_feature
<222> LOCATION: (38)..(38)
<223> OTHER INFORMATION: n is NapdU
<220> FEATURE:
<221> NAME/KEY: misc_feature
<222> LOCATION: (43)..(43)
<223> OTHER INFORMATION: n is NapdU

<400> SEQUENCE: 122
ctgtgagagg aaanacgcgc cnngannnac gnnnagcngc ganaacacaa            50

<210> SEQ ID NO 123
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(10)
<223> OTHER INFORMATION: n is NapdU
<220> FEATURE:
<221> NAME/KEY: misc_feature
<222> LOCATION: (14)..(14)
<223> OTHER INFORMATION: n is NapdU
<220> FEATURE:
<221> NAME/KEY: misc_feature
<222> LOCATION: (20)..(21)
<223> OTHER INFORMATION: n is NapdU
<220> FEATURE:
<221> NAME/KEY: misc_feature
<222> LOCATION: (24)..(26)
<223> OTHER INFORMATION: n is NapdU
<220> FEATURE:
<221> NAME/KEY: misc_feature
<222> LOCATION: (30)..(32)
<223> OTHER INFORMATION: n is NapdU
<220> FEATURE:
<221> NAME/KEY: misc_feature
<222> LOCATION: (37)..(37)
<223> OTHER INFORMATION: n is NapdU

<400> SEQUENCE: 123
ctgtgagcgn accncgcacn ngannnacgn nnagcgngcg gaggccacaa         50

<210> SEQ ID NO 124
<211> LENGTH: 49
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(10)
<223> OTHER INFORMATION: n is NapdU
<220> FEATURE:
<221> NAME/KEY: misc_feature
<222> LOCATION: (17)..(17)
<223> OTHER INFORMATION: n is NapdU
<220> FEATURE:
<221> NAME/KEY: misc_feature
<222> LOCATION: (21)..(22)
<223> OTHER INFORMATION: n is NapdU
<220> FEATURE:
<221> NAME/KEY: misc_feature
<222> LOCATION: (25)..(27)
<223> OTHER INFORMATION: n is NapdU
<220> FEATURE:
<221> NAME/KEY: misc_feature
<222> LOCATION: (31)..(33)
<223> OTHER INFORMATION: n is NapdU
<220> FEATURE:
<221> NAME/KEY: misc_feature
<222> LOCATION: (40)..(40)
<223> OTHER INFORMATION: n is NapdU
<220> FEATURE:
<221> NAME/KEY: misc_feature
<222> LOCATION: (44)..(44)
<223> OTHER INFORMATION: n is NapdU

<400> SEQUENCE: 124
ctgtgaccnn cacccgngac nnggnnnacg nnnagcgggn aggncacaa         49

<210> SEQ ID NO 125
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: n is NapdU
<220> FEATURE:
<221> NAME/KEY: misc_feature
<222> LOCATION: (13)..(14)
<223> OTHER INFORMATION: n is NapdU
<220> FEATURE:
<221> NAME/KEY: misc_feature
<222> LOCATION: (18)..(18)
<223> OTHER INFORMATION: n is NapdU
<220> FEATURE:
<221> NAME/KEY: misc_feature
<222> LOCATION: (24)..(25)
<223> OTHER INFORMATION: n is NapdU
<220> FEATURE:
<221> NAME/KEY: misc_feature
<222> LOCATION: (28)..(30)
<223> OTHER INFORMATION: n is NapdU
<220> FEATURE:
<221> NAME/KEY: misc_feature
<222> LOCATION: (34)..(36)
<223> OTHER INFORMATION: n is NapdU

<400> SEQUENCE: 125
ctgtggacng agnnggangg gacnngannn aagnnnagcc cgcaacacaa         50

<210> SEQ ID NO 126
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: n is NapdU
<220> FEATURE:
<221> NAME/KEY: misc_feature
<222> LOCATION: (16)..(17)
<223> OTHER INFORMATION: n is NapdU
<220> FEATURE:
<221> NAME/KEY: misc_feature
<222> LOCATION: (20)..(22)
<223> OTHER INFORMATION: n is NapdU
<220> FEATURE:
<221> NAME/KEY: misc_feature
<222> LOCATION: (26)..(28)
<223> OTHER INFORMATION: n is NapdU
<220> FEATURE:
<221> NAME/KEY: misc_feature
<222> LOCATION: (34)..(34)
<223> OTHER INFORMATION: n is NapdU
<220> FEATURE:
<221> NAME/KEY: misc_feature
<222> LOCATION: (43)..(44)
<223> OTHER INFORMATION: n is NapdU

<400> SEQUENCE: 126
ctgtggaang gcgacnngan nnaagnnnag cgcnacccccc aanngcacaa    50

<210> SEQ ID NO 127
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(7)
<223> OTHER INFORMATION: n is NapdU
<220> FEATURE:
<221> NAME/KEY: misc_feature
<222> LOCATION: (11)..(11)
<223> OTHER INFORMATION: n is NapdU
<220> FEATURE:
<221> NAME/KEY: misc_feature
<222> LOCATION: (15)..(16)
<223> OTHER INFORMATION: n is NapdU
<220> FEATURE:
<221> NAME/KEY: misc_feature
<222> LOCATION: (19)..(21)
<223> OTHER INFORMATION: n is NapdU
<220> FEATURE:
<221> NAME/KEY: misc_feature
<222> LOCATION: (25)..(27)
<223> OTHER INFORMATION: n is NapdU
<220> FEATURE:
<221> NAME/KEY: misc_feature
<222> LOCATION: (33)..(33)
<223> OTHER INFORMATION: n is NapdU
<220> FEATURE:
<221> NAME/KEY: misc_feature
<222> LOCATION: (44)..(44)
<223> OTHER INFORMATION: n is NapdU

<400> SEQUENCE: 127
ctgtgnnagg ngccnngcnn nacgnnnagc ccnacgaaac gccngcacaa    50

<210> SEQ ID NO 128
<211> LENGTH: 50

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(10)
<223> OTHER INFORMATION: n is NapdU
<220> FEATURE:
<221> NAME/KEY: misc_feature
<222> LOCATION: (14)..(14)
<223> OTHER INFORMATION: n is NapdU
<220> FEATURE:
<221> NAME/KEY: misc_feature
<222> LOCATION: (16)..(16)
<223> OTHER INFORMATION: n is NapdU
<220> FEATURE:
<221> NAME/KEY: misc_feature
<222> LOCATION: (22)..(23)
<223> OTHER INFORMATION: n is NapdU
<220> FEATURE:
<221> NAME/KEY: misc_feature
<222> LOCATION: (26)..(28)
<223> OTHER INFORMATION: n is NapdU
<220> FEATURE:
<221> NAME/KEY: misc_feature
<222> LOCATION: (32)..(34)
<223> OTHER INFORMATION: n is NapdU
<220> FEATURE:
<221> NAME/KEY: misc_feature
<222> LOCATION: (41)..(41)
<223> OTHER INFORMATION: n is NapdU
<220> FEATURE:
<221> NAME/KEY: misc_feature
<222> LOCATION: (43)..(43)
<223> OTHER INFORMATION: n is NapdU

<400> SEQUENCE: 128
ctgtgaacnn cganancgca cnngannnac gnnnaggcgg ngncacacaa         50

<210> SEQ ID NO 129
<211> LENGTH: 52
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(10)
<223> OTHER INFORMATION: n is NapdU
<220> FEATURE:
<221> NAME/KEY: misc_feature
<222> LOCATION: (14)..(14)
<223> OTHER INFORMATION: n is NapdU
<220> FEATURE:
<221> NAME/KEY: misc_feature
<222> LOCATION: (22)..(23)
<223> OTHER INFORMATION: n is NapdU
<220> FEATURE:
<221> NAME/KEY: misc_feature
<222> LOCATION: (26)..(28)
<223> OTHER INFORMATION: n is NapdU
<220> FEATURE:
<221> NAME/KEY: misc_feature
<222> LOCATION: (32)..(34)
<223> OTHER INFORMATION: n is NapdU
<220> FEATURE:
<221> NAME/KEY: misc_feature
<222> LOCATION: (39)..(39)
<223> OTHER INFORMATION: n is NapdU

<400> SEQUENCE: 129
ctgtgagagn aaanacgcgc anngannnac gnnnagcgng cggaggccac aa       52

<210> SEQ ID NO 130
```

```
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: n is NapdU
<220> FEATURE:
<221> NAME/KEY: misc_feature
<222> LOCATION: (8)..(8)
<223> OTHER INFORMATION: n is NapdU
<220> FEATURE:
<221> NAME/KEY: misc_feature
<222> LOCATION: (18)..(19)
<223> OTHER INFORMATION: n is NapdU
<220> FEATURE:
<221> NAME/KEY: misc_feature
<222> LOCATION: (22)..(24)
<223> OTHER INFORMATION: n is NapdU
<220> FEATURE:
<221> NAME/KEY: misc_feature
<222> LOCATION: (28)..(30)
<223> OTHER INFORMATION: n is NapdU

<400> SEQUENCE: 130
ctgtgncnag gagcggcnng cnnnacgnnn agacggaccc cacgacacaa        50

<210> SEQ ID NO 131
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: n is NapdU
<220> FEATURE:
<221> NAME/KEY: misc_feature
<222> LOCATION: (10)..(10)
<223> OTHER INFORMATION: n is NapdU
<220> FEATURE:
<221> NAME/KEY: misc_feature
<222> LOCATION: (14)..(14)
<223> OTHER INFORMATION: n is NapdU
<220> FEATURE:
<221> NAME/KEY: misc_feature
<222> LOCATION: (20)..(21)
<223> OTHER INFORMATION: n is NapdU
<220> FEATURE:
<221> NAME/KEY: misc_feature
<222> LOCATION: (24)..(26)
<223> OTHER INFORMATION: n is NapdU
<220> FEATURE:
<221> NAME/KEY: misc_feature
<222> LOCATION: (30)..(32)
<223> OTHER INFORMATION: n is NapdU

<400> SEQUENCE: 131
ctgtgagngn accncgcgcn ngannnacgn nnaggcgagg caggccacaa        50

<210> SEQ ID NO 132
<211> LENGTH: 45
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(10)
<223> OTHER INFORMATION: n is NapdU
<220> FEATURE:
<221> NAME/KEY: misc_feature
```

<222> LOCATION: (13)..(15)
<223> OTHER INFORMATION: n is NapdU
<220> FEATURE:
<221> NAME/KEY: misc_feature
<222> LOCATION: (19)..(21)
<223> OTHER INFORMATION: n is NapdU
<220> FEATURE:
<221> NAME/KEY: misc_feature
<222> LOCATION: (29)..(29)
<223> OTHER INFORMATION: n is NapdU
<220> FEATURE:
<221> NAME/KEY: misc_feature
<222> LOCATION: (37)..(37)
<223> OTHER INFORMATION: n is NapdU

<400> SEQUENCE: 132
ctgtgaacnn gannnaagnn naggcacana caccacnccg gacga    45

<210> SEQ ID NO 133
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(8)
<223> OTHER INFORMATION: n is NapdU
<220> FEATURE:
<221> NAME/KEY: misc_feature
<222> LOCATION: (18)..(19)
<223> OTHER INFORMATION: n is NapdU
<220> FEATURE:
<221> NAME/KEY: misc_feature
<222> LOCATION: (22)..(24)
<223> OTHER INFORMATION: n is NapdU
<220> FEATURE:
<221> NAME/KEY: misc_feature
<222> LOCATION: (28)..(30)
<223> OTHER INFORMATION: n is NapdU
<220> FEATURE:
<221> NAME/KEY: misc_feature
<222> LOCATION: (40)..(41)
<223> OTHER INFORMATION: n is NapdU

<400> SEQUENCE: 133
ctgtggnnaa cgacgacnng annnacgnnn agcggcaccn nacaccacaa    50

<210> SEQ ID NO 134
<211> LENGTH: 52
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: n is NapdU
<220> FEATURE:
<221> NAME/KEY: misc_feature
<222> LOCATION: (11)..(11)
<223> OTHER INFORMATION: n is NapdU
<220> FEATURE:
<221> NAME/KEY: misc_feature
<222> LOCATION: (20)..(21)
<223> OTHER INFORMATION: n is NapdU
<220> FEATURE:
<221> NAME/KEY: misc_feature
<222> LOCATION: (24)..(26)
<223> OTHER INFORMATION: n is NapdU
<220> FEATURE:
<221> NAME/KEY: misc_feature
<222> LOCATION: (30)..(32)
<223> OTHER INFORMATION: n is NapdU
<220> FEATURE:

```
<221> NAME/KEY: misc_feature
<222> LOCATION: (42)..(43)
<223> OTHER INFORMATION: n is NapdU

<400> SEQUENCE: 134
ctgtgnccac ncagccgacn ngannnacgn nnagcggcac cnnacaccac aa            52

<210> SEQ ID NO 135
<211> LENGTH: 47
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: n is NapdU
<220> FEATURE:
<221> NAME/KEY: misc_feature
<222> LOCATION: (11)..(11)
<223> OTHER INFORMATION: n is NapdU
<220> FEATURE:
<221> NAME/KEY: misc_feature
<222> LOCATION: (15)..(16)
<223> OTHER INFORMATION: n is NapdU
<220> FEATURE:
<221> NAME/KEY: misc_feature
<222> LOCATION: (19)..(21)
<223> OTHER INFORMATION: n is NapdU
<220> FEATURE:
<221> NAME/KEY: misc_feature
<222> LOCATION: (25)..(27)
<223> OTHER INFORMATION: n is NapdU
<220> FEATURE:
<221> NAME/KEY: misc_feature
<222> LOCATION: (37)..(38)
<223> OTHER INFORMATION: n is NapdU

<400> SEQUENCE: 135
ctgtgcgnac ngacnngann nacgnnnagc ggcaccnnac accacaa                  47

<210> SEQ ID NO 136
<211> LENGTH: 51
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: n is NapdU
<220> FEATURE:
<221> NAME/KEY: misc_feature
<222> LOCATION: (11)..(11)
<223> OTHER INFORMATION: n is NapdU
<220> FEATURE:
<221> NAME/KEY: misc_feature
<222> LOCATION: (15)..(16)
<223> OTHER INFORMATION: n is NapdU
<220> FEATURE:
<221> NAME/KEY: misc_feature
<222> LOCATION: (19)..(21)
<223> OTHER INFORMATION: n is NapdU
<220> FEATURE:
<221> NAME/KEY: misc_feature
<222> LOCATION: (25)..(28)
<223> OTHER INFORMATION: n is NapdU
<220> FEATURE:
<221> NAME/KEY: misc_feature
<222> LOCATION: (34)..(34)
<223> OTHER INFORMATION: n is NapdU
<220> FEATURE:
<221> NAME/KEY: misc_feature
<222> LOCATION: (38)..(38)
<223> OTHER INFORMATION: n is NapdU
```

<220> FEATURE:
<221> NAME/KEY: misc_feature
<222> LOCATION: (41)..(42)
<223> OTHER INFORMATION: n is NapdU

<400> SEQUENCE: 136
ctgtgcgnac ngacnngann nacgnnnnag cgangcangc nngagccaca a    51

<210> SEQ ID NO 137
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: n is NapdU
<220> FEATURE:
<221> NAME/KEY: misc_feature
<222> LOCATION: (13)..(13)
<223> OTHER INFORMATION: n is NapdU
<220> FEATURE:
<221> NAME/KEY: misc_feature
<222> LOCATION: (20)..(21)
<223> OTHER INFORMATION: n is NapdU
<220> FEATURE:
<221> NAME/KEY: misc_feature
<222> LOCATION: (24)..(26)
<223> OTHER INFORMATION: n is NapdU
<220> FEATURE:
<221> NAME/KEY: misc_feature
<222> LOCATION: (30)..(32)
<223> OTHER INFORMATION: n is NapdU
<220> FEATURE:
<221> NAME/KEY: misc_feature
<222> LOCATION: (45)..(45)
<223> OTHER INFORMATION: n is NapdU

<400> SEQUENCE: 137
ctgtgcnaag acngcggacn ngannnaggn nnagccgcaa gaagncacaa    50

<210> SEQ ID NO 138
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(11)
<223> OTHER INFORMATION: n is NapdU
<220> FEATURE:
<221> NAME/KEY: misc_feature
<222> LOCATION: (17)..(18)
<223> OTHER INFORMATION: n is NapdU
<220> FEATURE:
<221> NAME/KEY: misc_feature
<222> LOCATION: (21)..(23)
<223> OTHER INFORMATION: n is NapdU
<220> FEATURE:
<221> NAME/KEY: misc_feature
<222> LOCATION: (27)..(29)
<223> OTHER INFORMATION: n is NapdU
<220> FEATURE:
<221> NAME/KEY: misc_feature
<222> LOCATION: (36)..(37)
<223> OTHER INFORMATION: n is NapdU
<220> FEATURE:
<221> NAME/KEY: misc_feature
<222> LOCATION: (40)..(40)
<223> OTHER INFORMATION: n is NapdU
<220> FEATURE:
<221> NAME/KEY: misc_feature
<222> LOCATION: (45)..(45)

<223> OTHER INFORMATION: n is NapdU

<400> SEQUENCE: 138
ccctgcgccn ncggacnnga nnnaagnnna gccgcnngcn cacancacaa    50

<210> SEQ ID NO 139
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(11)
<223> OTHER INFORMATION: n is NapdU
<220> FEATURE:
<221> NAME/KEY: misc_feature
<222> LOCATION: (17)..(18)
<223> OTHER INFORMATION: n is NapdU
<220> FEATURE:
<221> NAME/KEY: misc_feature
<222> LOCATION: (21)..(23)
<223> OTHER INFORMATION: n is NapdU
<220> FEATURE:
<221> NAME/KEY: misc_feature
<222> LOCATION: (27)..(29)
<223> OTHER INFORMATION: n is NapdU
<220> FEATURE:
<221> NAME/KEY: misc_feature
<222> LOCATION: (36)..(37)
<223> OTHER INFORMATION: n is NapdU
<220> FEATURE:
<221> NAME/KEY: misc_feature
<222> LOCATION: (40)..(40)
<223> OTHER INFORMATION: n is NapdU
<220> FEATURE:
<221> NAME/KEY: misc_feature
<222> LOCATION: (45)..(45)
<223> OTHER INFORMATION: n is NapdU

<400> SEQUENCE: 139
ccctgcgccn ncggacnngg nnnaagnnna gccgcnngcn cacancacaa    50

<210> SEQ ID NO 140
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(11)
<223> OTHER INFORMATION: n is NapdU
<220> FEATURE:
<221> NAME/KEY: misc_feature
<222> LOCATION: (17)..(18)
<223> OTHER INFORMATION: n is NapdU
<220> FEATURE:
<221> NAME/KEY: misc_feature
<222> LOCATION: (21)..(23)
<223> OTHER INFORMATION: n is NapdU
<220> FEATURE:
<221> NAME/KEY: misc_feature
<222> LOCATION: (27)..(29)
<223> OTHER INFORMATION: n is NapdU
<220> FEATURE:
<221> NAME/KEY: misc_feature
<222> LOCATION: (36)..(37)
<223> OTHER INFORMATION: n is NapdU
<220> FEATURE:
<221> NAME/KEY: misc_feature
<222> LOCATION: (40)..(40)
<223> OTHER INFORMATION: n is NapdU
<220> FEATURE:
<221> NAME/KEY: misc_feature
<222> LOCATION: (45)..(45)
<223> OTHER INFORMATION: n is NapdU

<400> SEQUENCE: 140
ccctgcgccn ncggacnngc nnnaggnnna gccgcnngcn cacancacaa        50

<210> SEQ ID NO 141
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a, g, or c
<220> FEATURE:
<221> NAME/KEY: misc_feature
<222> LOCATION: (4)..(5)
<223> OTHER INFORMATION: n is a C-5 modified pyrimidine
<220> FEATURE:
<221> NAME/KEY: misc_feature
<222> LOCATION: (8)..(10)
<223> OTHER INFORMATION: n is a C-5 modified pyrimidine
<220> FEATURE:
<221> NAME/KEY: misc_feature
<222> LOCATION: (14)..(16)
<223> OTHER INFORMATION: n is a C-5 modified pyrimidine

<400> SEQUENCE: 141
nncnngrnnn amgnnnags        19

<210> SEQ ID NO 142
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: n is NapdU
<220> FEATURE:
<221> NAME/KEY: misc_feature
<222> LOCATION: (8)..(10)
<223> OTHER INFORMATION: n is NapdU
<220> FEATURE:
<221> NAME/KEY: misc_feature
<222> LOCATION: (14)..(16)
<223> OTHER INFORMATION: n is NapdU

<400> SEQUENCE: 142
gccnngannn acgnnnagc        19

<210> SEQ ID NO 143
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: n is NapdU
<220> FEATURE:
<221> NAME/KEY: misc_feature
<222> LOCATION: (8)..(10)
<223> OTHER INFORMATION: n is NapdU
<220> FEATURE:
<221> NAME/KEY: misc_feature
<222> LOCATION: (14)..(16)
<223> OTHER INFORMATION: n is NapdU

```
<400> SEQUENCE: 143
cacnngannn acgnnnagg                                                  19

<210> SEQ ID NO 144
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: n is NapdU
<220> FEATURE:
<221> NAME/KEY: misc_feature
<222> LOCATION: (8)..(10)
<223> OTHER INFORMATION: n is NapdU
<220> FEATURE:
<221> NAME/KEY: misc_feature
<222> LOCATION: (14)..(16)
<223> OTHER INFORMATION: n is NapdU

<400> SEQUENCE: 144
gacnnggnnn acgnnnagc                                                  19

<210> SEQ ID NO 145
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: n is NapdU
<220> FEATURE:
<221> NAME/KEY: misc_feature
<222> LOCATION: (8)..(10)
<223> OTHER INFORMATION: n is NapdU
<220> FEATURE:
<221> NAME/KEY: misc_feature
<222> LOCATION: (14)..(16)
<223> OTHER INFORMATION: n is NapdU

<400> SEQUENCE: 145
gccnngcnnn acgnnnagc                                                  19

<210> SEQ ID NO 146
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: n is NapdU
<220> FEATURE:
<221> NAME/KEY: misc_feature
<222> LOCATION: (8)..(10)
<223> OTHER INFORMATION: n is NapdU
<220> FEATURE:
<221> NAME/KEY: misc_feature
<222> LOCATION: (14)..(16)
<223> OTHER INFORMATION: n is NapdU

<400> SEQUENCE: 146
gcanngannn acgnnnagc                                                  19

<210> SEQ ID NO 147
<211> LENGTH: 19
```

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: n is NapdU
<220> FEATURE:
<221> NAME/KEY: misc_feature
<222> LOCATION: (8)..(10)
<223> OTHER INFORMATION: n is NapdU
<220> FEATURE:
<221> NAME/KEY: misc_feature
<222> LOCATION: (14)..(16)
<223> OTHER INFORMATION: n is NapdU

<400> SEQUENCE: 147
ggcnngcnnn acgnnnaga                                               19

<210> SEQ ID NO 148
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: n is NapdU
<220> FEATURE:
<221> NAME/KEY: misc_feature
<222> LOCATION: (8)..(10)
<223> OTHER INFORMATION: n is NapdU
<220> FEATURE:
<221> NAME/KEY: misc_feature
<222> LOCATION: (14)..(16)
<223> OTHER INFORMATION: n is NapdU

<400> SEQUENCE: 148
cgcnngannn aagnnnagg                                               19

<210> SEQ ID NO 149
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: n is NapdU
<220> FEATURE:
<221> NAME/KEY: misc_feature
<222> LOCATION: (8)..(10)
<223> OTHER INFORMATION: n is NapdU
<220> FEATURE:
<221> NAME/KEY: misc_feature
<222> LOCATION: (14)..(16)
<223> OTHER INFORMATION: n is NapdU

<400> SEQUENCE: 149
aacnngannn aagnnnagg                                               19

<210> SEQ ID NO 150
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
```

```
<223> OTHER INFORMATION: n is NapdU
<220> FEATURE:
<221> NAME/KEY: misc_feature
<222> LOCATION: (8)..(10)
<223> OTHER INFORMATION: n is NapdU
<220> FEATURE:
<221> NAME/KEY: misc_feature
<222> LOCATION: (14)..(16)
<223> OTHER INFORMATION: n is NapdU

<400> SEQUENCE: 150
gacnngannn aggnnnagc                                                   19

<210> SEQ ID NO 151
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: may or may not be present
<220> FEATURE:
<221> NAME/KEY: misc_feature
<222> LOCATION: (4)..(4)
<223> OTHER INFORMATION: may or may not be present
<220> FEATURE:
<221> NAME/KEY: misc_feature
<222> LOCATION: (6)..(7)
<223> OTHER INFORMATION: n is a C-5 modified pyrimidine
<220> FEATURE:
<221> NAME/KEY: misc_feature
<222> LOCATION: (9)..(9)
<223> OTHER INFORMATION: may or may not be present
<220> FEATURE:
<221> NAME/KEY: misc_feature
<222> LOCATION: (11)..(13)
<223> OTHER INFORMATION: n is a C-5 modified pyrimidine
<220> FEATURE:
<221> NAME/KEY: misc_feature
<222> LOCATION: (14)..(14)
<223> OTHER INFORMATION: may or may not be present
<220> FEATURE:
<221> NAME/KEY: misc_feature
<222> LOCATION: (16)..(16)
<223> OTHER INFORMATION: may or may not be present
<220> FEATURE:
<221> NAME/KEY: misc_feature
<222> LOCATION: (18)..(18)
<223> OTHER INFORMATION: may or may not be present
<220> FEATURE:
<221> NAME/KEY: misc_feature
<222> LOCATION: (20)..(20)
<223> OTHER INFORMATION: may or may not be present
<220> FEATURE:
<221> NAME/KEY: misc_feature
<222> LOCATION: (21)..(22)
<223> OTHER INFORMATION: n is a C-5 modified pyrimidine
<220> FEATURE:
<221> NAME/KEY: misc_feature
<222> LOCATION: (23)..(23)
<223> OTHER INFORMATION: may or may not be present
<220> FEATURE:
<221> NAME/KEY: misc_feature
<222> LOCATION: (24)..(24)
<223> OTHER INFORMATION: n is a C-5 modified pyrimidine
<220> FEATURE:
<221> NAME/KEY: misc_feature
<222> LOCATION: (26)..(26)
<223> OTHER INFORMATION: may or may not be present

<400> SEQUENCE: 151
rwmccnngmm nnnaacmcrw nngnasgs                                         28
```

```
<210> SEQ ID NO 152
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: may or may not be present
<220> FEATURE:
<221> NAME/KEY: misc_feature
<222> LOCATION: (4)..(4)
<223> OTHER INFORMATION: may or may not be present
<220> FEATURE:
<221> NAME/KEY: misc_feature
<222> LOCATION: (6)..(7)
<223> OTHER INFORMATION: n is a C-5 modified pyrimidine
<220> FEATURE:
<221> NAME/KEY: misc_feature
<222> LOCATION: (9)..(9)
<223> OTHER INFORMATION: may or may not be present
<220> FEATURE:
<221> NAME/KEY: misc_feature
<222> LOCATION: (11)..(13)
<223> OTHER INFORMATION: n is a C-5 modified pyrimidine
<220> FEATURE:
<221> NAME/KEY: misc_feature
<222> LOCATION: (14)..(14)
<223> OTHER INFORMATION: may or may not be present
<220> FEATURE:
<221> NAME/KEY: misc_feature
<222> LOCATION: (16)..(16)
<223> OTHER INFORMATION: may or may not be present
<220> FEATURE:
<221> NAME/KEY: misc_feature
<222> LOCATION: (18)..(18)
<223> OTHER INFORMATION: may or may not be present
<220> FEATURE:
<221> NAME/KEY: misc_feature
<222> LOCATION: (20)..(20)
<223> OTHER INFORMATION: may or may not be present
<220> FEATURE:
<221> NAME/KEY: misc_feature
<222> LOCATION: (21)..(22)
<223> OTHER INFORMATION: n is a C-5 modified pyrimidine
<220> FEATURE:
<221> NAME/KEY: misc_feature
<222> LOCATION: (23)..(23)
<223> OTHER INFORMATION: may or may not be present
<220> FEATURE:
<221> NAME/KEY: misc_feature
<222> LOCATION: (24)..(24)
<223> OTHER INFORMATION: n is a C-5 modified pyrimidine
<220> FEATURE:
<221> NAME/KEY: misc_feature
<222> LOCATION: (26)..(26)
<223> OTHER INFORMATION: may or may not be present

<400> SEQUENCE: 152
rwaccnngmm nnnaacmcrw nngnasgs                                              28

<210> SEQ ID NO 153
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: may or may not be present
<220> FEATURE:
<221> NAME/KEY: misc_feature
<222> LOCATION: (4)..(4)
<223> OTHER INFORMATION: may or may not be present
<220> FEATURE:
```

<221> NAME/KEY: misc_feature
<222> LOCATION: (6)..(7)
<223> OTHER INFORMATION: n is a C-5 modified pyrimidine
<220> FEATURE:
<221> NAME/KEY: misc_feature
<222> LOCATION: (9)..(9)
<223> OTHER INFORMATION: may or may not be present
<220> FEATURE:
<221> NAME/KEY: misc_feature
<222> LOCATION: (11)..(13)
<223> OTHER INFORMATION: n is a C-5 modified pyrimidine
<220> FEATURE:
<221> NAME/KEY: misc_feature
<222> LOCATION: (14)..(14)
<223> OTHER INFORMATION: may or may not be present
<220> FEATURE:
<221> NAME/KEY: misc_feature
<222> LOCATION: (16)..(16)
<223> OTHER INFORMATION: may or may not be present
<220> FEATURE:
<221> NAME/KEY: misc_feature
<222> LOCATION: (18)..(18)
<223> OTHER INFORMATION: may or may not be present
<220> FEATURE:
<221> NAME/KEY: misc_feature
<222> LOCATION: (20)..(20)
<223> OTHER INFORMATION: may or may not be present
<220> FEATURE:
<221> NAME/KEY: misc_feature
<222> LOCATION: (21)..(22)
<223> OTHER INFORMATION: n is a C-5 modified pyrimidine
<220> FEATURE:
<221> NAME/KEY: misc_feature
<222> LOCATION: (23)..(23)
<223> OTHER INFORMATION: may or may not be present
<220> FEATURE:
<221> NAME/KEY: misc_feature
<222> LOCATION: (24)..(24)
<223> OTHER INFORMATION: n is a C-5 modified pyrimidine
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (26)..(26)
<223> OTHER INFORMATION: may or may not be present

<400> SEQUENCE: 153
rwmccnngmm nnnaacmcgw nngnasgs                                      28

<210> SEQ ID NO 154
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: n is a C-5 modified pyrimidine
<220> FEATURE:
<221> NAME/KEY: misc_feature
<222> LOCATION: (7)..(7)
<223> OTHER INFORMATION: may or may not be present
<220> FEATURE:
<221> NAME/KEY: misc_feature
<222> LOCATION: (9)..(11)
<223> OTHER INFORMATION: n is a C-5 modified pyrimidine
<220> FEATURE:
<221> NAME/KEY: misc_feature
<222> LOCATION: (12)..(12)
<223> OTHER INFORMATION: may or may not be present
<220> FEATURE:
<221> NAME/KEY: misc_feature
<222> LOCATION: (14)..(14)
<223> OTHER INFORMATION: may or may not be present

```
<220> FEATURE:
<221> NAME/KEY: misc_feature
<222> LOCATION: (16)..(16)
<223> OTHER INFORMATION: may or may not be present
<220> FEATURE:
<221> NAME/KEY: misc_feature
<222> LOCATION: (18)..(18)
<223> OTHER INFORMATION: may or may not be present
<220> FEATURE:
<221> NAME/KEY: misc_feature
<222> LOCATION: (19)..(21)
<223> OTHER INFORMATION: n is a C-5 modified pyrimidine
<220> FEATURE:
<221> NAME/KEY: misc_feature
<222> LOCATION: (23)..(23)
<223> OTHER INFORMATION: may or may not be present

<400> SEQUENCE: 154
rmcnngmmnn naacmcrwnn nasgs                                   25

<210> SEQ ID NO 155
<211> LENGTH: 6
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: n is a C-5 modified pyrimidine

<400> SEQUENCE: 155 nnnagg                                                         6

<210> SEQ ID NO 156
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: n is NapdU
<220> FEATURE:
<221> NAME/KEY: misc_feature
<222> LOCATION: (8)..(10)
<223> OTHER INFORMATION: n is NapdU
<220> FEATURE:
<221> NAME/KEY: misc_feature
<222> LOCATION: (14)..(16)
<223> OTHER INFORMATION: n is NapdU

<400> SEQUENCE: 156
gacnngcnnn aagnnnagcc                                         20

<210> SEQ ID NO 157
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: n is NapdU
<220> FEATURE:
<221> NAME/KEY: misc_feature
<222> LOCATION: (9)..(11)
<223> OTHER INFORMATION: n is NapdU
<220> FEATURE:
<221> NAME/KEY: misc_feature
<222> LOCATION: (15)..(17)
```

<223> OTHER INFORMATION: n is NapdU

<400> SEQUENCE: 157
ggacnngcnn naagnnnagc c                                              21

<210> SEQ ID NO 158
<211> LENGTH: 48
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: n is NapdU
<220> FEATURE:
<221> NAME/KEY: misc_feature
<222> LOCATION: (11)..(11)
<223> OTHER INFORMATION: n is NapdU
<220> FEATURE:
<221> NAME/KEY: misc_feature
<222> LOCATION: (18)..(19)
<223> OTHER INFORMATION: n is NapdU
<220> FEATURE:
<221> NAME/KEY: misc_feature
<222> LOCATION: (22)..(24)
<223> OTHER INFORMATION: n is NapdU
<220> FEATURE:
<221> NAME/KEY: misc_feature
<222> LOCATION: (28)..(30)
<223> OTHER INFORMATION: n is NapdU
<220> FEATURE:
<221> NAME/KEY: misc_feature
<222> LOCATION: (35)..(35)
<223> OTHER INFORMATION: n is NapdU

<400> SEQUENCE: 158
ctgtggagnc ncccgacnng annnacgnnn agcgngcgga ggccacaa                 48

<210> SEQ ID NO 159
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: n is NapdU
<220> FEATURE:
<221> NAME/KEY: misc_feature
<222> LOCATION: (11)..(11)
<223> OTHER INFORMATION: n is NapdU
<220> FEATURE:
<221> NAME/KEY: misc_feature
<222> LOCATION: (20)..(21)
<223> OTHER INFORMATION: n is NapdU
<220> FEATURE:
<221> NAME/KEY: misc_feature
<222> LOCATION: (24)..(26)
<223> OTHER INFORMATION: n is NapdU
<220> FEATURE:
<221> NAME/KEY: misc_feature
<222> LOCATION: (30)..(32)
<223> OTHER INFORMATION: n is NapdU
<220> FEATURE:

```
<221> NAME/KEY: misc_feature
<222> LOCATION: (37)..(37)
<223> OTHER INFORMATION: n is NapdU

<400> SEQUENCE: 159
ctgtgnccac ncagccgacn ngannnacgn nnagcgngcg gaggccacaa            50

<210> SEQ ID NO 160
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: n is a C-5 modified pyrimidine
<220> FEATURE:
<221> NAME/KEY: misc_feature
<222> LOCATION: (6)..(8)
<223> OTHER INFORMATION: n is a C-5 modified pyrimidine
<220> FEATURE:
<221> NAME/KEY: misc_feature
<222> LOCATION: (9)..(13)
<223> OTHER INFORMATION: n, if present, is a, c, g, t, or u; up to 3
      nucleotides may be absent
<220> FEATURE:
<221> NAME/KEY: misc_feature
<222> LOCATION: (14)..(16)
<223> OTHER INFORMATION: n is a C-5 modified pyrimidine

<400> SEQUENCE: 160
cnngmnnnnn nnnnnnagg                                              19
```